(12) United States Patent
Gilmore et al.

(10) Patent No.: US 11,990,229 B2
(45) Date of Patent: May 21, 2024

(54) HEALTHCARE PROVIDER CLAIMS DENIALS PREVENTION SYSTEMS AND METHODS

(71) Applicant: Ayasdi AI LLC, Menlo Park, CA (US)

(72) Inventors: Allison Gilmore, Redwood City, CA (US); Tzu-Wei Powers, Mountain View, CA (US); Alan Lehman, Palo Alto, CA (US); Cindy Zhang, San Jose, CA (US)

(73) Assignee: SymphonyAI Sensa LLC, Palo Alto, CA (US)

( * ) Notice: Subject to any disclaimer, the term of this patent is extended or adjusted under 35 U.S.C. 154(b) by 0 days.

(21) Appl. No.: 15/909,974

(22) Filed: Mar. 1, 2018

(65) Prior Publication Data

US 2018/0254101 A1    Sep. 6, 2018

Related U.S. Application Data

(60) Provisional application No. 62/465,719, filed on Mar. 1, 2017.

(51) Int. Cl.
*G16H 40/20* (2018.01)
*G06T 11/20* (2006.01)
*G16H 15/00* (2018.01)

(52) U.S. Cl.
CPC ........... *G16H 40/20* (2018.01); *G06T 11/206* (2013.01); *G16H 15/00* (2018.01)

(58) Field of Classification Search
CPC ..... G06F 19/328; G06T 11/206; G16H 40/20; G16H 10/60; G16H 15/00; G06Q 40/08; G06Q 20/405; G06Q 30/04

USPC .......................................................... 705/2, 3
See application file for complete search history.

(56) References Cited

U.S. PATENT DOCUMENTS

| | | | |
|---|---|---|---|
| 8,447,627 B1 | 5/2013 | Cruise | |
| 8,612,255 B1 * | 12/2013 | Kirsh | G06Q 10/10 705/2 |
| 8,972,899 B2 | 3/2015 | Carlsson | |
| 2013/0054259 A1 | 2/2013 | Wojtusiak | |
| 2013/0144916 A1 | 6/2013 | Lum | |

(Continued)

OTHER PUBLICATIONS

International Application No. PCT/US2018/020552, International Search Report and Written Opinion dated May 4, 2018.

*Primary Examiner* — Mamon Obeid
*Assistant Examiner* — Teresa S Williams
(74) *Attorney, Agent, or Firm* — Ahmann Kloke LLP

(57) ABSTRACT

An example system includes a memory, processor, and instructions to receive a set of multidimensional adjudicated claims data, receive metric and lens functions, perform the metric and lens functions on a set of dimensions of the claims data to map claims to a reference space, generate cover of overlapping sets of the reference space, cluster the mapped claims in the reference space using the cover to identify nodes and edges, identify groups of nodes in a graph based on known improperly denied, for each group, identify differentiating drivers, and generate a denials application user interface depicting different cards for each of at least a subset of the identified groups in the graph that includes the known improperly denied claims, each card indicating a set of primary statistics of the claims in the nodes of that group, for each card depicting the differentiating drivers of that group.

22 Claims, 51 Drawing Sheets

(56) References Cited

U.S. PATENT DOCUMENTS

| | | | |
|---|---|---|---|
| 2015/0039333 A1* | 2/2015 | de Traversay | G06Q 10/06395 |
| | | | 705/2 |
| 2015/0127370 A1* | 5/2015 | Cornelis | G06Q 10/10 |
| | | | 705/2 |
| 2015/0317337 A1* | 11/2015 | Edgar | G06F 17/30 |
| | | | 707/751 |
| 2016/0342750 A1* | 11/2016 | Alstad | G06F 19/328 |
| 2016/0350389 A1 | 12/2016 | Kloke | |
| 2017/0017760 A1* | 1/2017 | Freese | G06F 19/328 |

* cited by examiner

| Patient ID | Gene 1 Expression | Gene 2 Expression | ... | Gene y Expression | Clinical Outcome |
|---|---|---|---|---|---|
| P1 | G1a | G2a | | Gya | Outcome P1 |
| P2 | G1b | G2b | | Gyb | Outcome P2 |
| P3 | G1c | G2c | | Gyc | Outcome P3 |
| ⋮ | ⋮ | ⋮ | | ⋮ | ⋮ |
| Pn | G1n | G2n | | Gyn | Outcome Pn |

Sample Report of Hotspot Analysis showing categorization and statistics

HEALTHCARE PROVIDER CLAIMS DENIALS PREVENTION SYSTEMS AND METHODS

CROSS-REFERENCE TO RELATED APPLICATION

The present application claims the benefit of U.S. Provisional Patent Application Ser. No. 62/465,719 filed Mar. 1, 2017 and entitled "Healthcare Provider Claims Denials Prevention Systems and Methods," which is incorporated herein by reference.

BACKGROUND

1. Field of the Invention

Embodiments of the present invention(s) are directed to grouping of data points for data analysis and more particularly to generating a graph utilizing improved groupings of data points based on scores of the groupings.

2. Related Art

Denials are among the most persistent problems in the healthcare revenue cycle, with the potential to cost a leading U.S. hospital well over $100 million annually. Although the problem did not double or triple with the arrival of ICD-10, as some feared it might, the challenges brought on by the new ICD-10 codes were bound to exacerbate the problem, primarily because they add complexity where the problem was already persisting because of complexity.

According to the not-for-profit HealthCare Administrative Solutions, Inc., about 25 percent of all claims are rejected by payers at least once. Although this percentage does not reflect the ultimate figure experienced by top hospitals-which is closer to 3.8 percent, according the Medical Group Management Association, it does provide a significant data foundation on which to evaluate the problem.

One might expect the Pareto principle, also known as the 80/20 rule, to apply here, and to some extent it does. Many of those denied claims are due to clerical errors, missed codes, and incomplete fields. Technology exists to quarantine many of the claims that exhibit such deficiencies so they can be corrected before they enter the denial phase.

These types of errors, however, are not what pose the real challenge in managing denials. The real challenge with denied claims is to find a way to go beyond identifying mistakes and evaluating denied claims one-by-one to be able to identify meaningful patterns of denials so that processes can be put into place to address whole groups of claims at once.

Further complicating matters is the fact that the labyrinth of payer rules has proven an ineffective guide to providers. Payer application of their own rules is often uneven. Providers can and do adapt. As a result, pockets of knowledge are created about which claims are likely to be denied, despite rules that explicitly state otherwise. Such knowledge has limited utility, however, because it is subject to changing payer behavior, employee attrition, and new regulation-like ICD-10.

Consider, for example, that a hospital's most successful coding team may have been intimately familiar with just 35 percent of the more than 14,000 codes under ICD-9 (i.e., approximately 4,900 codes). The number of possible combinations within those codes is too big to fit on the page.

Under ICD-10, with the same 35 percent threshold, the team would have to have a grasp of 23,800 codes, creating a staggering combinatorial complexity, given that the number of possible combinations for that number far exceeds the estimated number of atoms in the universe.

It will take time for both providers and payers to respond to ICD-10, but the problem is more suited to data science and machines. Highly skilled and productive coding teams will still be valuable, but their value will lie in helping to develop the new processes and workflows based on the data and their knowledge of the payers.

In an example of increasing complexity, consider the following scenario involving screening colonoscopy claims, which are notorious for being rejected on grounds of lack of medical necessity. Providers regularly run afoul of the complex coding guidelines.

A provider typically is faced with a variety of coding scenarios, each of which can be susceptible to the adjudicator's inconsistent interpretation of the guidelines:

Screening colonoscopy for Medicare patients
 Screening colonoscopy for non-Medicare patients
 Screening colonoscopy for Medicare patients that becomes diagnostic or therapeutic
 Screening colonoscopy for non-Medicare patients that becomes diagnostic or therapeutic Success in this case depends on the ordering of the diagnoses codes in the claim and the selection of the appropriate "G" code or HCPCS code for the appropriate scenario above. Properly sequencing the codes triggers the screening colonoscopy as "diagnostic," thereby affecting how much of the payment is covered or deferred to the patient's out-of-pocket expense.

It has taken those providers that understand this principle time to obtain this knowledge and make appropriate adjustments, and the very fact that this knowledge is inherently local explains why this known problem claim persists to the extent that it does.

Moreover, there also is considerable variation from payer to payer regarding specific reporting preferences. Within a specific payer, there is the additional variability of individual adjudicator preferences.

Traditionally, providers have employed two ways of categorizing claims into actionable batches. The macro approach, usually performed by the finance team or the denials core team, generally involves the use of Excel or other tools to make pivot tables that break down payer type, facility type, or denial type. This approach helps to characterize problems and identify areas of interest, but is not specific enough to be actionable. It is possible to get a broad view of where denials are occurring, but there is little or no insight into why. In other words, this approach is scalable but not actionable.

By contrast, the micro approach can produce results that are sufficiently actionable but not scalable. In this approach, a person studies actual claims (e.g., usually tens of claims) to ascertain whether these claims might have been miscoded in the same way. Although actionability is high, this process is labor-intensive, and knowledge often does not travel beyond the facility. Therefore, its scalability is limited.

SUMMARY OF THE INVENTION(S)

An example non-transitory computer readable medium includes executable instructions. The instructions are executable by a processor to perform a method. The method may comprise receiving a set of multidimensional adjudicated claims data, the multidimensional adjudicated claims data including information regarding claim denials for health services, a subset of the multidimensional adjudicated claims data including known claim denials that were improperly denied, receiving at least one metric function and at least one lens function selection, performing the metric and lens functions on a set of dimensions of the set of multidimensional adjudicated claims data to map claims from the multidimensional adjudicated claims data to a reference space, generating cover of overlapping sets of the reference space based on a resolution, clustering the mapped claims in the reference space using the cover to identify nodes in a graph, each node including one or more claims from the multidimensional adjudicated claims data as members, each node being connected to another node if they share at least one common claim as members, generating a graph of the nodes and edges, identifying groups of nodes in the graph based on known improperly denied claims that are members of the nodes, for each group, identifying differentiating drivers based on dimensions of the claims in the nodes of that group, the differentiating drivers being particular to that group relative to other groups in the graph, and generating a denials application user interface depicting a card for each of at least a subset of the identified groups in the graph that includes the known improperly denied claims that are the members of the nodes, each card indicating a set of primary statistics based on at least one dimension of each of the claims in the nodes of that group, for each card, the denials application user interface further depicting the differentiating drivers based on the dimensions of the claims in the nodes of that group.

The multidimensional adjudicated claims data may include at least one claim for precertification for medical services and/or at least one claim for medical services already rendered.

In some embodiments, the set of dimensions of the set of multidimensional adjudicated claims data is filtered to a reduced set of dimensions prior to performing the metric and lens functions on the set of dimensions. Identifying the groups of nodes in the graph based on the known improper claims that are the members of the nodes may include identifying nodes containing claims with similar dimensions and similar claim denials. The multidimensional adjudicated claims data may include at least one dimension regarding reasons for claim denial.

In various embodiments, the method may further comprise ranking the groups of the nodes in the graph based on cost of claim denials relative to the other groups of the nodes in the graph. The denials application user interface may be configured to display on each depicted card the cost of claim denials. In some embodiments, the denials application user interface is configured to order the cost based on the cost of claim denials.

The method may further comprise receiving a new adjudicated claim, comparing dimensions of the new adjudicated claim to the groups and predicting a likelihood that the new adjudicated claim is improperly denied. In some embodiments, comparing the dimensions of the new adjudicated claim to the groups includes comparing the dimensions of the new adjudicated claim to the differentiating drivers of each group.

An example system may comprise at least one processor and memory containing instructions. The instructions may configure the at least one processor to receive a set of multidimensional adjudicated claims data, the multidimensional adjudicated claims data including information regarding claim denials for health services, a subset of the multidimensional adjudicated claims data including known claim denials that were improperly denied, receive at least one metric function and at least one lens function selection, perform the metric and lens functions on a set of dimensions of the set of multidimensional adjudicated claims data to map claims from the multidimensional adjudicated claims data to a reference space, generate a cover of overlapping sets of the reference space based on a resolution, cluster the mapped claims in the reference space using the cover to identify nodes in a graph, each node including one or more claims from the multidimensional adjudicated claims data as members, each node being connected to another node if they share at least one common claim as members, generate a graph of the nodes and edges, identify groups of nodes in the graph based on known improperly denied claims that are members of the nodes, for each group, identify differentiating drivers based on dimensions of the claims in the nodes of that group, the differentiating drivers being particular to that group relative to other groups in the graph, and generate a denials application user interface depicting a card for each of at least a subset of the identified groups in the graph that includes the known improperly denied claims that are the members of the nodes, each card indicating a set of primary statistics based on at least one dimension of each of the claims in the nodes of that group, for each card, the denials application user interface further depicting the differentiating drivers based on the dimensions of the claims in the nodes of that group.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 13 is an example data structure including biological data for a number of patients that may be used to generate the cancer map visualization in some embodiments.

FIG. 24 is an example report of an autogrouped graph of data points that depicts the grouped data in some embodiments.

FIG. 29B depicts an example report of hotspot analysis showing categorization and statistics to further review hotspots or groups.

DETAILED DESCRIPTION OF THE DRAWINGS

Some embodiments described herein may be a part of the subject of Topological Data Analysis (TDA). TDA is an area of research which has produced methods for studying point cloud data sets from a geometric point of view. Other data analysis techniques use "approximation by models" of various types. For example, regression methods model the data as the graph of a function in one or more variables. Unfortunately, certain qualitative properties (which one can readily observe when the data is two-dimensional) may be of a great deal of importance for understanding, and these features may not be readily represented within such models.

Figure 1A:
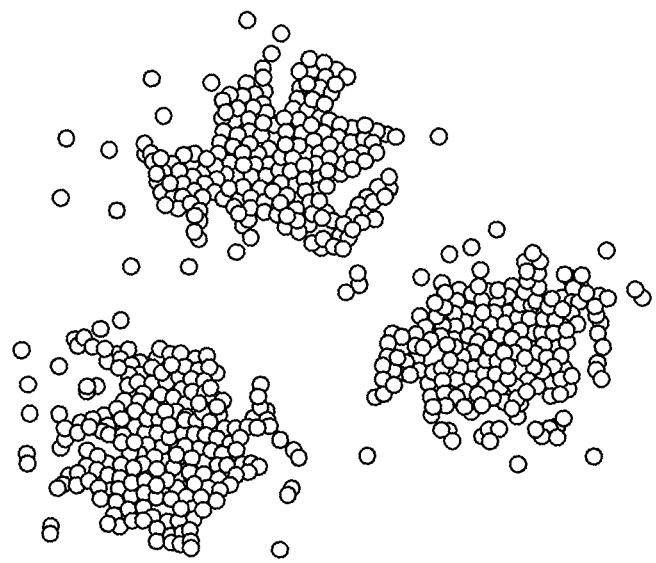
FIG. 1A is an example graph representing data that appears to be divided into three disconnected groups.

FIG. 1A is an example graph representing data that appears to be divided into three disconnected groups. In this example, the data for this graph may be associated with various physical characteristics related to different population groups or biomedical data related to different forms of a disease. Seeing that the data breaks into groups in this fashion can give insight into the data, once one understands what characterizes the groups.

Figure 1B:
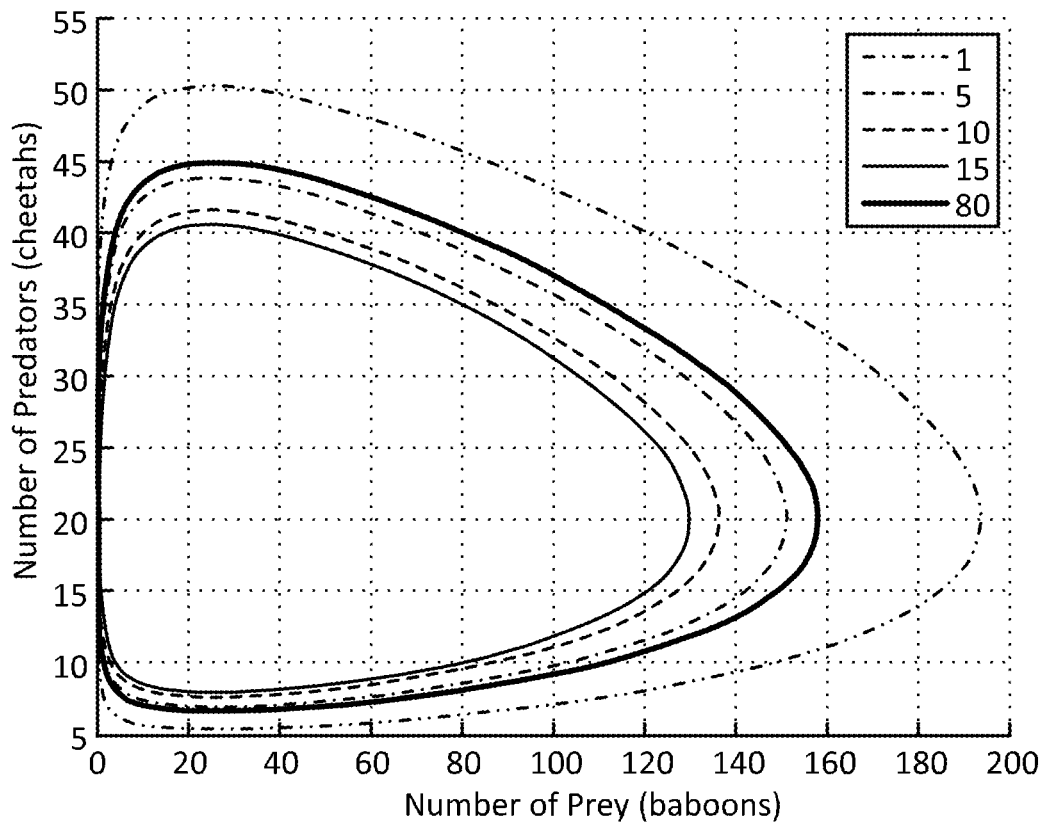
FIG. 1B is an example graph representing data set obtained from a Lotka-Volterra equation modeling the populations of predators and prey over time.

FIG. 1B is an example graph representing data set obtained from a Lotka-Volterra equation modeling the populations of predators and prey over time. From FIG. 1B, one observation about this data is that it is arranged in a loop. The loop is not exactly circular, but it is topologically a circle. The exact form of the equations, while interesting, may not be of as much importance as this qualitative observation which reflects the fact that the underlying phenomenon is recurrent or periodic. When looking for periodic or recurrent phenomena, methods may be developed which can detect the presence of loops without defining explicit models. For example, periodicity may be detectable without having to first develop a fully accurate model of the dynamics.

Figure 1C:
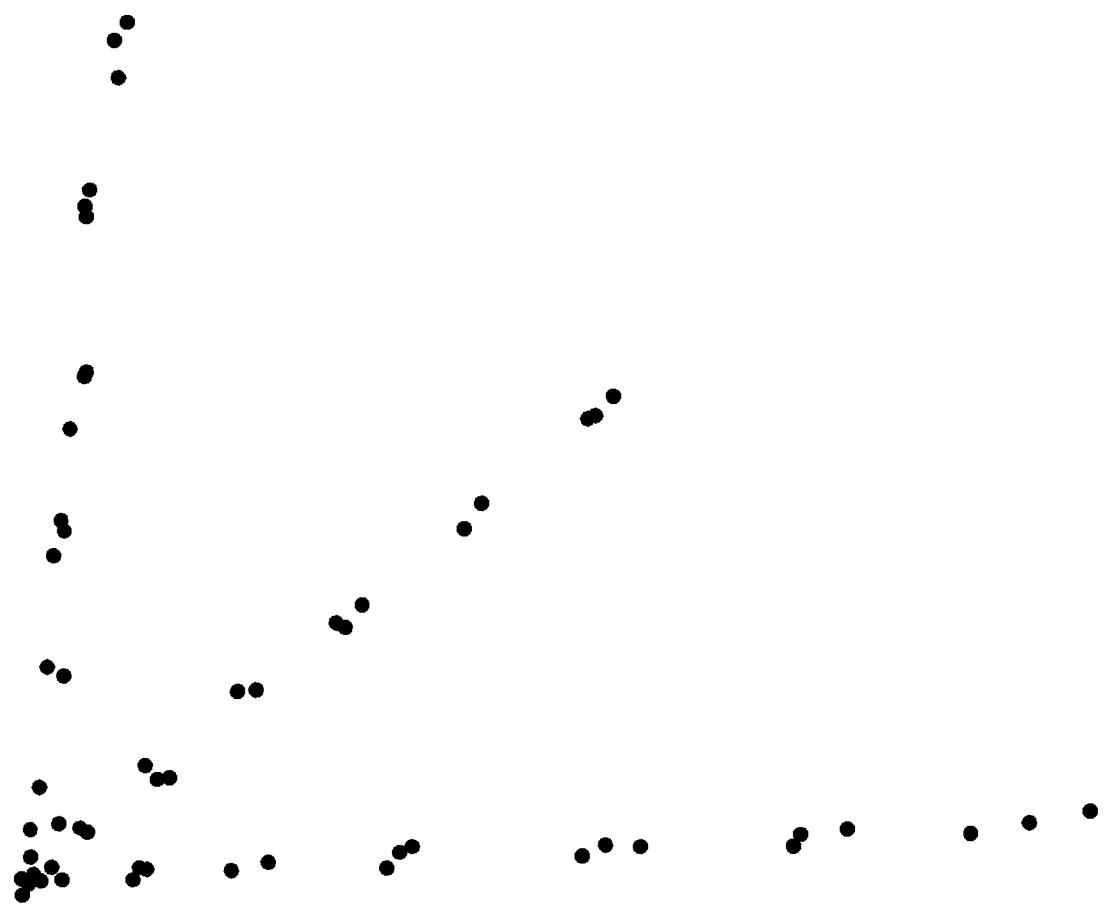
FIG. 1C is an example graph of data sets whereby the data does not break up into disconnected groups, but instead has a structure in which there are lines (or flares) emanating from a central group.

FIG. 1C is an example graph of data sets whereby the data does not break up into disconnected groups, but instead has a structure in which there are lines (or flares) emanating from a central group. In this case, the data also suggests the presence of three distinct groups, but the connectedness of the data does not reflect this. This particular data that is the basis for the example graph in FIG. 1C arises from a study of single nucleotide polymorphisms (SNPs).

In each of the examples above, aspects of the shape of the data are relevant in reflecting information about the data. Connectedness (the simplest property of shape) reflects the presence of a discrete classification of the data into disparate groups. The presence of loops, another simple aspect of shape, often reflect periodic or recurrent behavior. Finally, in the third example, the shape containing flares suggests a classification of the data descriptive of ways in which phenomena can deviate from the norm, which would typically be represented by the central core. These examples support the idea that the shape of data (suitably defined) is an important aspect of its structure, and that it is therefore important to develop methods for analyzing and understanding its shape. The part of mathematics which concerns itself with the study of shape is called topology, and topological data analysis attempts to adapt methods for studying shape which have been developed in pure mathematics to the study of the shape of data, suitably defined.

One question is how notions of geometry or shape are translated into information about point clouds, which are, after all, finite sets? What we mean by shape or geometry can come from a dissimilarity function or metric (e.g., a non-negative, symmetric, real-valued function d on the set of pairs of points in the data set which may also satisfy the triangle inequality, and d(x; y)=0 if and only if x=y). Such functions exist in profusion for many data sets. For example, when the data comes in the form of a numerical matrix, where the rows correspond to the data points and the columns are the fields describing the data, the n-dimensional Euclidean distance function is natural when there are n fields. Similarly, in this example, there are Pearson correlation distances, cosine distances, and other choices.

When the data is not Euclidean, for example if one is considering genomic sequences, various notions of distance may be defined using measures of similarity based on Basic Local Alignment Search Tool (BLAST) type similarity scores. Further, a measure of similarity can come in non-numeric forms, such as social networks of friends or similarities of hobbies, buying patterns, tweeting, and/or professional interests. In any of these ways the notion of shape may be formulated via the establishment of a useful notion of similarity of data points.

One of the advantages of TDA is that it may depend on nothing more than such a notion, which is a very primitive or low-level model. It may rely on many fewer assumptions than standard linear or algebraic models, for example. Further, the methodology may provide new ways of visualizing and compressing data sets, which facilitate understanding and monitoring data. The methodology may enable study of interrelationships among disparate data sets and/or multiscale/multiresolution study of data sets. Moreover, the methodology may enable interactivity in the analysis of data, using point and click methods.

TDA may be a very useful complement to more traditional methods, such as Principal Component Analysis (PCA), multidimensional scaling, and hierarchical clustering. These existing methods are often quite useful, but suffer from significant limitations. PCA, for example, is an essentially linear procedure and there are therefore limits to its utility in highly non-linear situations. Multidimensional scaling is a method which is not intrinsically linear, but can in many situations wash out detail, since it may overweight large distances. In addition, when metrics do not satisfy an intrinsic flatness condition, it may have difficulty in faithfully representing the data. Hierarchical clustering does exhibit multiscale behavior, but represents data only as disjoint clusters, rather than retaining any of the geometry of the data set. In all four cases, these limitations matter for many varied kinds of data.

We now summarize example properties of an example construction, in some embodiments, which may be used for representing the shape of data sets in a useful, understandable fashion as a finite graph:

The input may be a collection of data points equipped in some way with a distance or dissimilarity function, or other description. This can be given implicitly when the data is in the form of a matrix, or explicitly as a matrix of distances or even the generating edges of a mathematical network.

One construction may also use one or more lens functions (i.e. real valued functions on the data). Lens function(s) may depend directly on the metric. For example, lens function(s) might be the result of a density estimator or a measure of centrality or data depth. Lens function(s) may, in some embodiments, depend on a particular representation of the data, as when one uses the first one or two coordinates of a principal component or multidimensional scaling analysis. In some embodiments, the lens function(s) may be columns which expert knowledge identifies as being intrinsically interesting, as in cholesterol levels and BMI in a study of heart disease.

In some embodiments, the construction may depend on a choice of two or more processing parameters, resolution, and gain. Increase in resolution typically results in more nodes and an increase in the gain increases the number of edges in a visualization and/or graph in a reference space as further described herein.

The output may be, for example, a visualization (e.g., a display of connected nodes or "network") or simplicial complex. One specific combinatorial formulation in one embodiment may be that the vertices form a finite set, and then the additional structure may be a collection of edges (unordered pairs of vertices) which are pictured as connections in this network.

In various embodiments, a system for handling, analyzing, and visualizing data using drag and drop methods as opposed to text based methods is described herein. Philosophically, data analytic tools are not necessarily regarded as "solvers," but rather as tools for interacting with data. For example, data analysis may consist of several iterations of a process in which computational tools point to regions of interest in a data set. The data set may then be examined by people with domain expertise concerning the data, and the data set may then be subjected to further computational analysis. In some embodiments, methods described herein provide for going back and forth between mathematical constructs, including interactive visualizations (e.g., graphs), on the one hand and data on the other.

In one example of data analysis in some embodiments described herein, an example clustering tool is discussed which may be more powerful than existing technology, in that one can find structure within clusters and study how clusters change over a period of time or over a change of scale or resolution.

An example interactive visualization tool (e.g., a visualization module which is further described herein) may produce combinatorial output in the form of a graph which can be readily visualized. In some embodiments, the example interactive visualization tool may be less sensitive to changes in notions of distance than current methods, such as multidimensional scaling.

Some embodiments described herein permit manipulation of the data from a visualization. For example, portions of the data which are deemed to be interesting from the visualization can be selected and converted into database objects, which can then be further analyzed. Some embodiments described herein permit the location of data points of interest within the visualization, so that the connection between a given visualization and the information the visualization represents may be readily understood.

Figure 2:
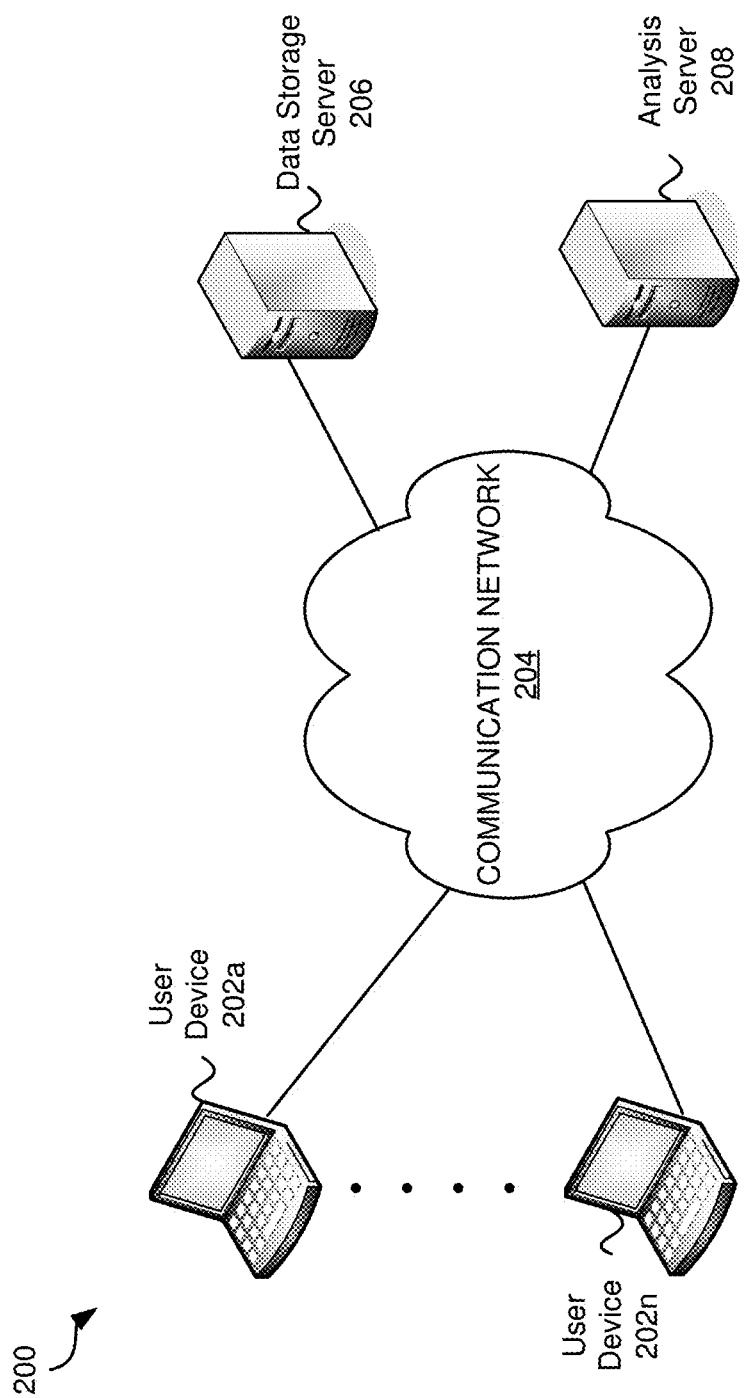
FIG. 2 is an example environment in which embodiments may be practiced.

FIG. 2 is an example environment 200 in which embodiments may be practiced. In various embodiments, data analysis and interactive visualization may be performed locally (e.g., with software and/or hardware on a local digital device), across a network (e.g., via cloud computing), or a combination of both. In many of these embodiments, a data structure is accessed to obtain the data for the analysis, the analysis is performed based on properties and parameters selected by a user, and an interactive visualization is generated and displayed. There are many advantages between performing all or some activities locally and many advantages of performing all or some activities over a network.

Environment 200 comprises user devices 202a-202n, a communication network 204, data storage server 206, and analysis server 208. Environment 200 depicts an embodiment wherein functions are performed across a network. In this example, the user(s) may take advantage of cloud computing by storing data in a data storage server 206 over a communication network 204. The analysis server 208 may perform analysis and generation of an interactive visualization.

User devices 202a-202n may be any digital devices. A digital device is any device that comprises memory and a processor. Digital devices are further described in FIG. 2. The user devices 202a-202n may be any kind of digital device that may be used to access, analyze and/or view data including, but not limited to a desktop computer, laptop, notebook, or other computing device.

In various embodiments, a user, such as a data analyst, may generate a database or other data structure with the user device 202a to be saved to the data storage server 206. The user device 202a may communicate with the analysis server 208 via the communication network 204 to perform analysis, examination, and visualization of data within the database.

The user device 202a may comprise a client program for interacting with one or more applications on the analysis server 208. In other embodiments, the user device 202a may communicate with the analysis server 208 using a browser or other standard program. In various embodiments, the user device 202a communicates with the analysis server 208 via a virtual private network. It will be appreciated that that communication between the user device 202a, the data storage server 206, and/or the analysis server 208 may be encrypted or otherwise secured.

The communication network 204 may be any network that allows digital devices to communicate. The communication network 204 may be the Internet and/or include LAN and WANs. The communication network 204 may support wireless and/or wired communication.

The data storage server 206 is a digital device that is configured to store data. In various embodiments, the data storage server 206 stores databases and/or other data structures. The data storage server 206 may be a single server or a combination of servers. In one example the data storage server 206 may be a secure server wherein a user may store data over a secured connection (e.g., via https). The data may be encrypted and backed-up. In some embodiments, the data storage server 206 is operated by a third-party such as Amazon's S3 service.

The database or other data structure may comprise large high-dimensional datasets. These datasets are traditionally very difficult to analyze and, as a result, relationships within the data may not be identifiable using previous methods. Further, previous methods may be computationally inefficient.

The analysis server 208 is a digital device that may be configured to analyze data. In various embodiments, the analysis server may perform many functions to interpret, examine, analyze, and display data and/or relationships within data. In some embodiments, the analysis server 208 performs, at least in part, topological analysis of large datasets applying metrics, filters, and resolution parameters chosen by the user. The analysis is further discussed in FIG. 8 herein.

The analysis server 208 may generate an interactive visualization of the output of the analysis. The interactive visualization allows the user to observe and explore relationships in the data. In various embodiments, the interactive visualization allows the user to select nodes comprising data that has been clustered. The user may then access the underlying data, perform further analysis (e.g., statistical analysis) on the underlying data, and manually reorient the graph(s) (e.g., structures of nodes and edges described herein) within the interactive visualization. The analysis server 208 may also allow for the user to interact with the data, see the graphic result. The interactive visualization is further discussed in FIGS. 9-11.

In some embodiments, the analysis server 208 interacts with the user device(s) 202a-202n over a private and/or secure communication network. The user device 202a may comprise a client program that allows the user to interact with the data storage server 206, the analysis server 208, another user device (e.g., user device 202n), a database, and/or an analysis application executed on the analysis server 208.

Those skilled in the art will appreciate that all or part of the data analysis may occur at the user device 202a. Further, all or part of the interaction with the visualization (e.g., graphic) may be performed on the user device 202a.

Although two user devices 202a and 202n are depicted, those skilled in the art will appreciate that there may be any number of user devices in any location (e.g., remote from each other). Similarly, there may be any number of communication networks, data storage servers, and analysis servers.

Cloud computing may allow for greater access to large datasets (e.g., via a commercial storage service) over a faster connection. Further, it will be appreciated that services and computing resources offered to the user(s) may be scalable.

Figure 3:
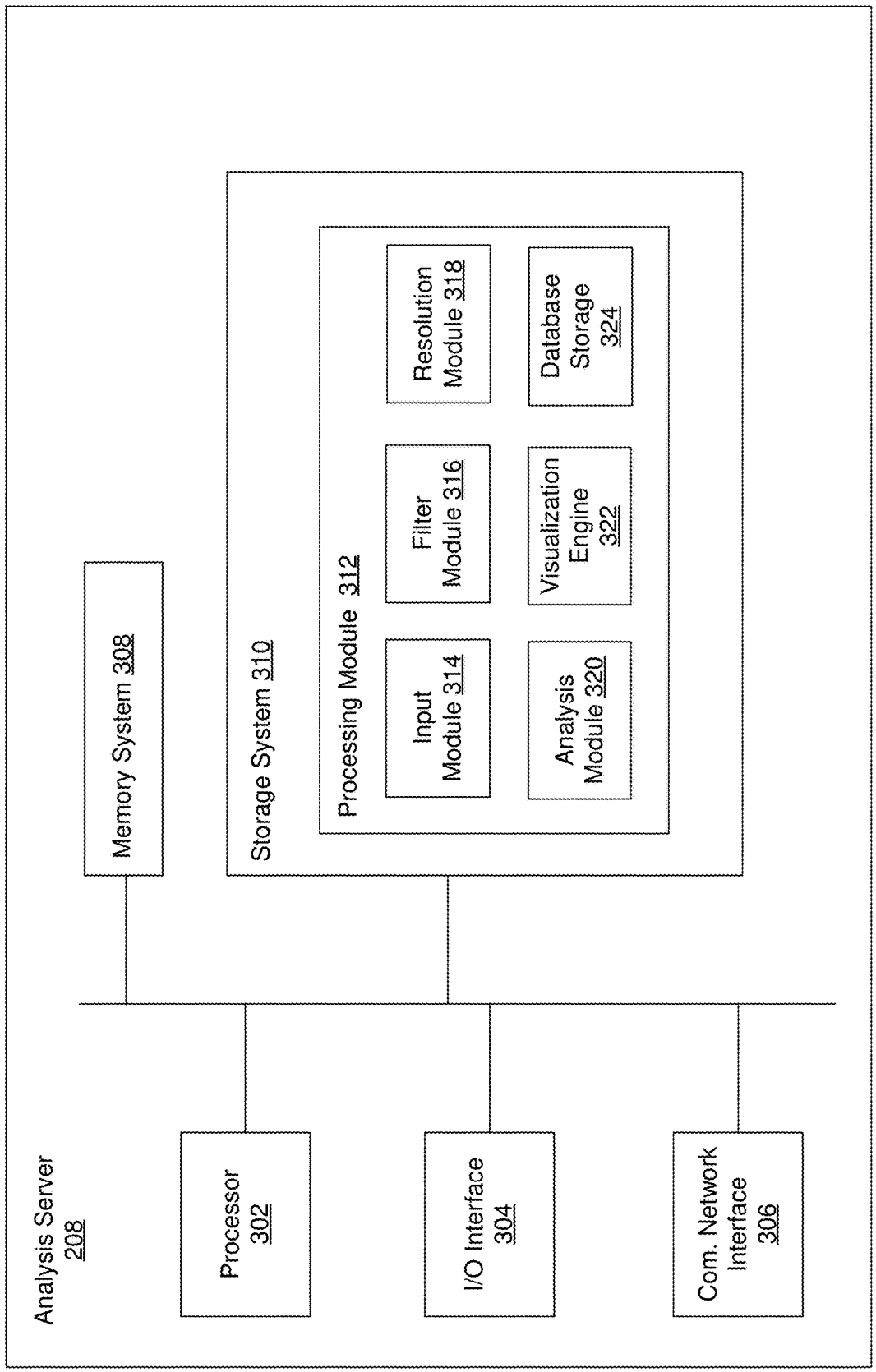
FIG. 3 is a block diagram of an example analysis server.

FIG. 3 is a block diagram of an example analysis server 208. In example embodiments, the analysis server 208 comprises a processor 302, input/output (I/O) interface 304, a communication network interface 306, a memory system 308, a storage system 310, and a processing module 312. The processor 302 may comprise any processor or combination of processors with one or more cores.

The input/output (I/O) interface 304 may comprise interfaces for various I/O devices such as, for example, a keyboard, mouse, and display device. The example communication network interface 306 is configured to allow the analysis server 208 to communication with the communication network 204 (see FIG. 2). The communication network interface 306 may support communication over an Ethernet connection, a serial connection, a parallel connection, and/or an ATA connection. The communication network interface 306 may also support wireless communication (e.g., 802.11 a/b/g/n, WiMax, LTE, WiFi). It will be apparent to those skilled in the art that the communication network interface 306 can support many wired and wireless standards.

The memory system 308 may be any kind of memory including RAM, ROM, or flash, cache, virtual memory, etc. In various embodiments, working data is stored within the memory system 308. The data within the memory system 308 may be cleared or ultimately transferred to the storage system 310.

The storage system 310 includes any storage configured to retrieve and store data. Some examples of the storage system 310 include flash drives, hard drives, optical drives, and/or magnetic tape. Each of the memory system 308 and the storage system 310 comprises a computer-readable medium, which stores instructions (e.g., software programs) executable by processor 302.

The storage system 310 comprises a plurality of modules utilized by embodiments of discussed herein. A module may be hardware, software (e.g., including instructions executable by a processor), or a combination of both. In one embodiment, the storage system 310 comprises a processing module 312 which comprises an input module 314, a filter module 316, a resolution module 318, an analysis module 320, a visualization engine 322, and database storage 324. Alternative embodiments of the analysis server 208 and/or the storage system 310 may comprise more, less, or functionally equivalent components and modules.

The input module 314 may be configured to receive commands and preferences from the user device 202a. In various examples, the input module 314 receives selections from the user which will be used to perform the analysis. The output of the analysis may be an interactive visualization.

The input module 314 may provide the user a variety of interface windows allowing the user to select and access a database, choose fields associated with the database, choose a metric, choose one or more filters, and identify resolution parameters for the analysis. In one example, the input module 314 receives a database identifier and accesses a large multidimensional database. The input module 314 may scan the database and provide the user with an interface window allowing the user to identify an ID field. An ID field is an identifier for each data point. In one example, the identifier is unique. The same column name may be present in the table from which filters are selected. After the ID field is selected, the input module 314 may then provide the user with another interface window to allow the user to choose one or more data fields from a table of the database.

Although interactive windows may be described herein, it will be appreciated that any window, graphical user interface, and/or command line may be used to receive or prompt a user or user device 202a for information.

The filter module 316 may subsequently provide the user with an interface window to allow the user to select a metric to be used in analysis of the data within the chosen data fields. The filter module 316 may also allow the user to select and/or define one or more filters.

The resolution module 218 may allow the user to select a resolution, including filter parameters. In one example, the user enters a number of intervals and a percentage overlap for a filter.

The analysis module 320 may perform data analysis based on the database and the information provided by the user. In various embodiments, the analysis module 320 performs an algebraic topological analysis to identify structures and relationships within data and clusters of data. It will be appreciated that the analysis module 320 may use parallel algorithms or use generalizations of various statistical techniques (e.g., generalizing the bootstrap to zig-zag methods) to increase the size of data sets that can be processed. The analysis is further discussed in FIG. 8. It will be appreciated that the analysis module 320 is not limited to algebraic topological analysis but may perform any analysis.

The visualization engine 322 generates an interactive visualization including the output from the analysis module 320. The interactive visualization allows the user to see all or part of the analysis graphically. The interactive visualization also allows the user to interact with the visualization. For example, the user may select portions of a graph from within the visualization to see and/or interact with the underlying data and/or underlying analysis. The user may then change the parameters of the analysis (e.g., change the metric, filter(s), or resolution(s)) which allows the user to visually identify relationships in the data that may be otherwise undetectable using prior means. The interactive visualization is further described in FIGS. 9-11.

The database storage 324 is configured to store all or part of the database that is being accessed. In some embodiments, the database storage 324 may store saved portions of the database. Further, the database storage 324 may be used to store user preferences, parameters, and analysis output thereby allowing the user to perform many different functions on the database without losing previous work.

It will be appreciated that that all or part of the processing module 312 may be at the user device 202a or the database storage server 206. In some embodiments, all or some of the functionality of the processing module 312 may be performed by the user device 202a.

In various embodiments, systems and methods discussed herein may be implemented with one or more digital devices. In some examples, some embodiments discussed herein may be implemented by a computer program (instructions) executed by a processor. The computer program may provide a graphical user interface. Although such a computer program is discussed, it will be appreciated that embodiments may be performed using any of the following, either alone or in combination, including, but not limited to, a computer program, multiple computer programs, firmware, and/or hardware.

A module and/or engine may include any processor or combination of processors. In some examples, a module and/or engine may include or be a part of a processor, digital signal processor (DSP), application specific integrated circuit (ASIC), an integrated circuit, and/or the like. In various embodiments, the module and/or engine may be software or firmware.

Figure 4:
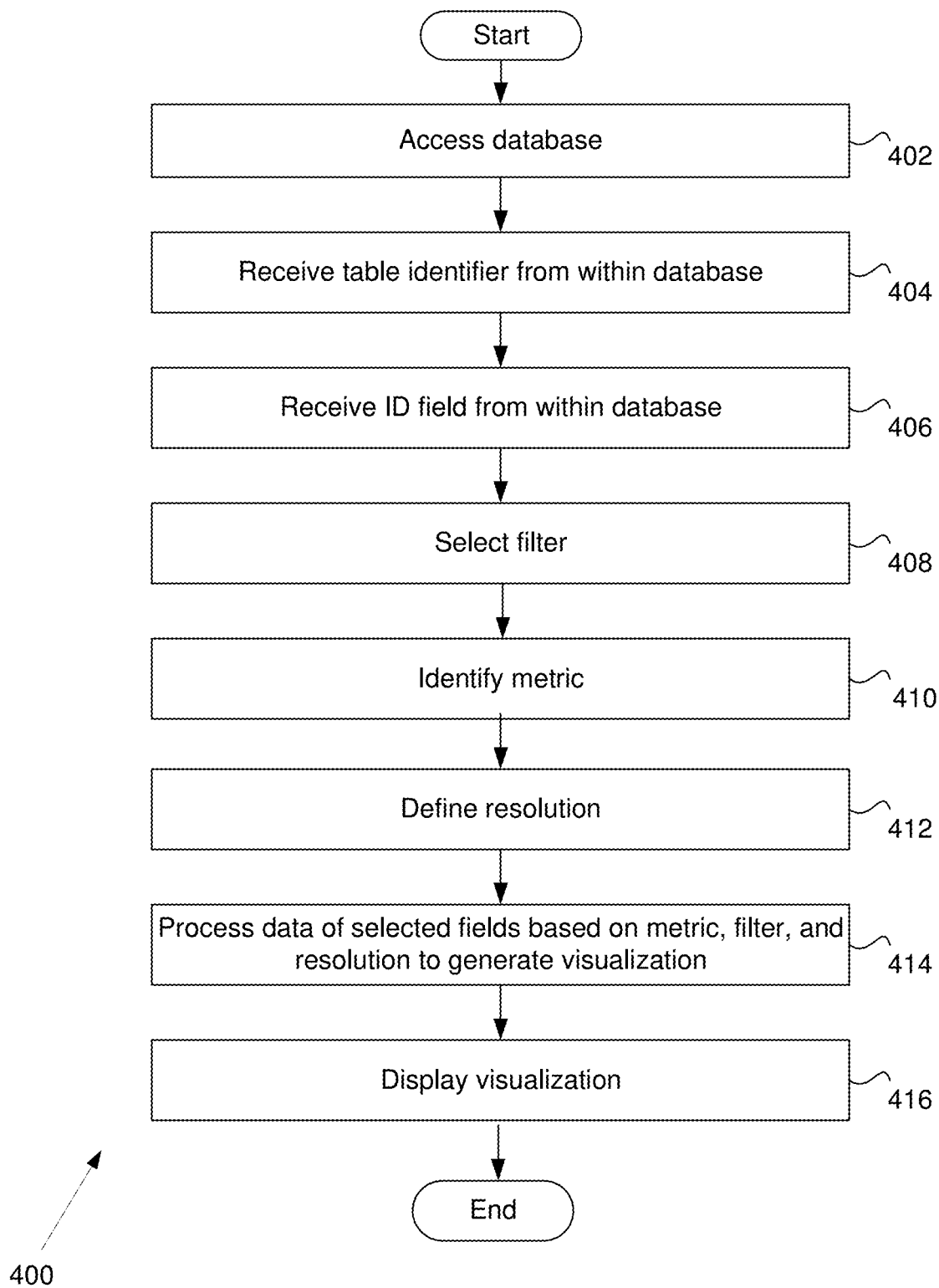
FIG. 4 is a flow chart depicting an example method of dataset analysis and visualization in some embodiments.

FIG. 4 is a flow chart 400 depicting an example method of dataset analysis and visualization in some embodiments. In step 402, the input module 314 accesses a database. The database may be any data structure containing data (e.g., a very large dataset of multidimensional data). In some embodiments, the database may be a relational database. In some examples, the relational database may be used with MySQL, Oracle, Micosoft SQL Server, Aster nCluster, Teradata, and/or Vertica. It will be appreciated that the database may not be a relational database.

In some embodiments, the input module 314 receives a database identifier and a location of the database (e.g., the data storage server 206) from the user device 202a (see FIG. 2). The input module 314 may then access the identified database. In various embodiments, the input module 314 may read data from many different sources, including, but not limited to MS Excel files, text files (e.g., delimited or CSV), Matlab .mat format, or any other file.

In some embodiments, the input module 314 receives an IP address or hostname of a server hosting the database, a username, password, and the database identifier. This information (herein referred to as "connection information") may be cached for later use. It will be appreciated that the database may be locally accessed and that all, some, or none of the connection information may be required. In one example, the user device 202a may have full access to the database stored locally on the user device 202a so the IP address is unnecessary. In another example, the user device 202a may already have loaded the database and the input module 314 merely begins by accessing the loaded database.

In various embodiments, the identified database stores data within tables. A table may have a "column specification" which stores the names of the columns and their data types. A "row" in a table, may be a tuple with one entry for each column of the correct type. In one example, a table to store employee records might have a column specification such as:

employee_id primary key int (this may store the employee's ID as an integer, and uniquely identifies a row)
age int
gender char(1) (gender of the employee may be a single character either M or F)
salary double (salary of an employee may be a floating point number)
name varchar (name of the employee may be a variable-length string)

In this example, each employee corresponds to a row in this table. Further, the tables in this example relational database are organized into logical units called databases. An analogy to file systems is that databases can be thought of as folders and files as tables. Access to databases may be controlled by the database administrator by assigning a username/password pair to authenticate users.

Once the database is accessed, the input module 314 may allow the user to access a previously stored analysis or to begin a new analysis. If the user begins a new analysis, the input module 314 may provide the user device 202a with an interface window allowing the user to identify a table from within the database. In one example, the input module 314 provides a list of available tables from the identified database.

In step 404, the input module 314 receives a table identifier identifying a table from within the database. The input module 314 may then provide the user with a list of available ID fields from the table identifier. In step 406, the input module 314 receives the ID field identifier from the user and/or user device 202a. The ID field is, in some embodiments, the primary key.

Having selected the primary key, the input module 314 may generate a new interface window to allow the user to select data fields for analysis. In step 408, the input module 314 receives data field identifiers from the user device 202a. The data within the data fields may be later analyzed by the analysis module 320.

In step 410, the filter module 316 identifies a metric. In some embodiments, the filter module 316 and/or the input module 314 generates an interface window allowing the user of the user device 202a options for a variety of different metrics and filter preferences. The interface window may be a drop down menu identifying a variety of distance metrics to be used in the analysis. Metric options may include, but are not limited to, Euclidean, DB Metric, variance normalized Euclidean, and total normalized Euclidean. The metric and the analysis are further described herein.

In step 412, the filter module 316 selects one or more filters. In some embodiments, the user selects and provides filter identifier(s) to the filter module 316. The role of the filters in the analysis is also further described herein. The filters, for example, may be user defined, geometric, or based on data which has been pre-processed. In some embodiments, the data based filters are numerical arrays which can assign a set of real numbers to each row in the table or each point in the data generally.

A variety of geometric filters may be available for the user to choose. Geometric filters may include, but are not limited to:

Density
L1 Eccentricity
L-infinity Eccentricity
Witness based Density
Witness based Eccentricity
Eccentricity as distance from a fixed point
Approximate Kurtosis of the Eccentricity In step 414, the resolution module 218 defines the resolution to be used with a filter in the analysis. The resolution may comprise a number of intervals and an overlap parameter. In various embodiments, the resolution module 218 allows the user to adjust the number of intervals and overlap parameter (e.g., percentage overlap) for one or more filters.

In step 416, the analysis module 320 processes data of selected fields based on the metric, filter(s), and resolution(s) to generate the visualization. This process is discussed in FIG. 8.

In step 418, the visualization module 322 displays the interactive visualization. In various embodiments, the visualization may be rendered in two or three dimensional space. The visualization module 322 may use an optimization algorithm for an objective function which is correlated with good visualization (e.g., the energy of the embedding). The visualization may show a collection of nodes corresponding to each of the partial clusters in the analysis output and edges connecting them as specified by the output. The interactive visualization is further discussed in FIGS. 9-11.

Although many examples discuss the input module 314 as providing interface windows, it will be appreciated that all or some of the interface may be provided by a client on the user device 202a. Further, in some embodiments, the user device 202a may be running all or some of the processing module 212.

Figure 5:
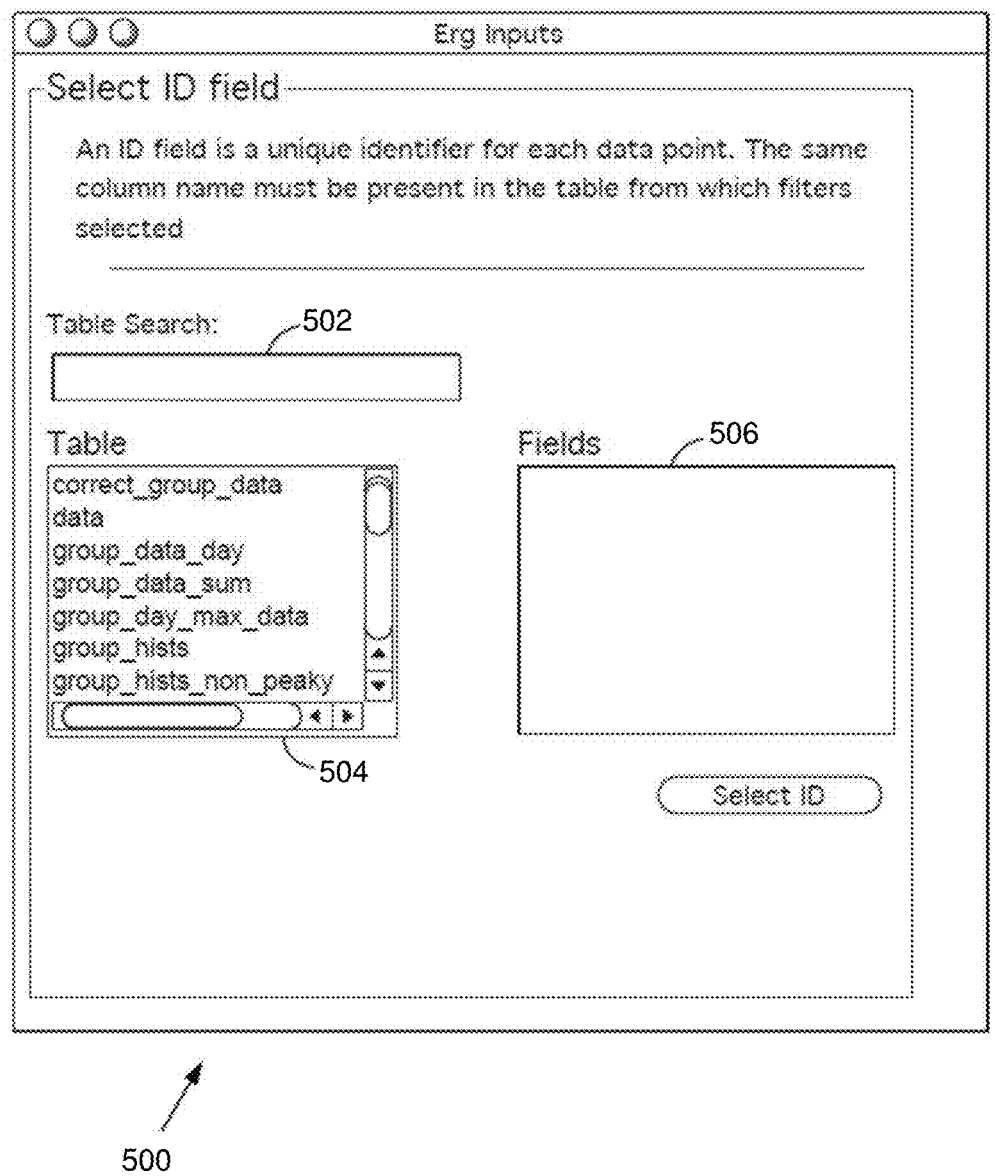
FIG. 5 is an example ID field selection interface window in some embodiments.
Figure 6A:
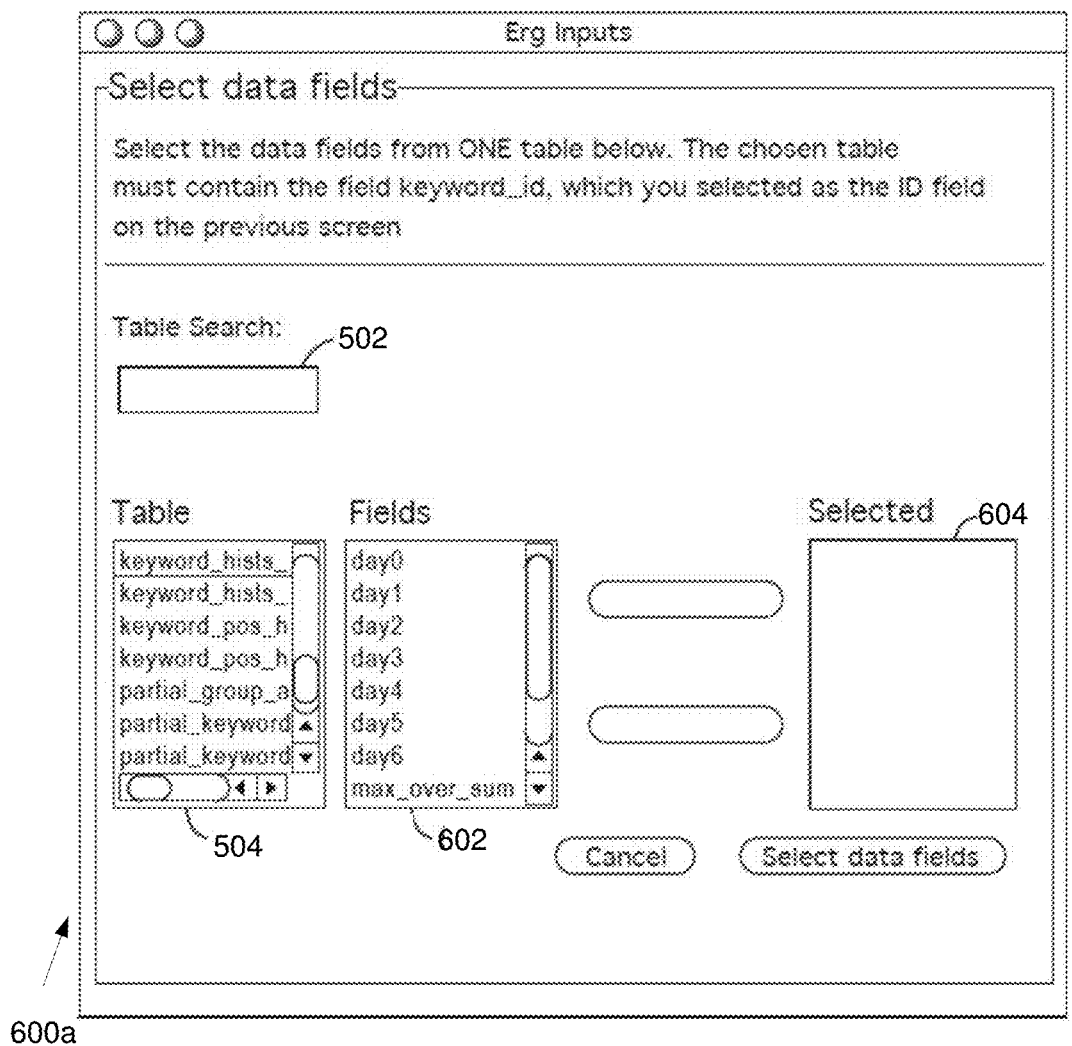
FIG. 6A is an example data field selection interface window in some embodiments.
Figure 6B:
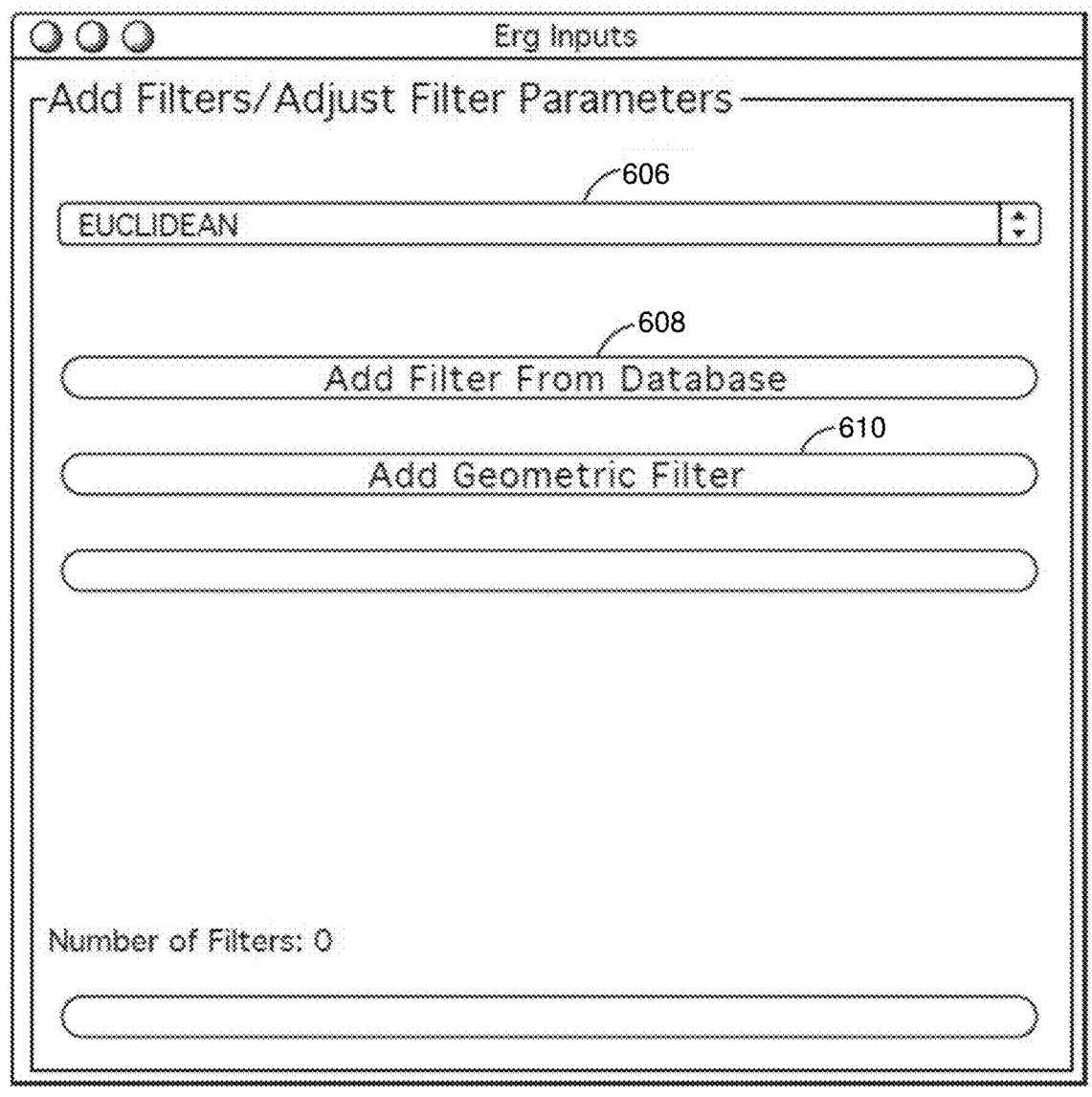
FIG. 6B is an example metric and filter selection interface window in some embodiments.
Figure 7:
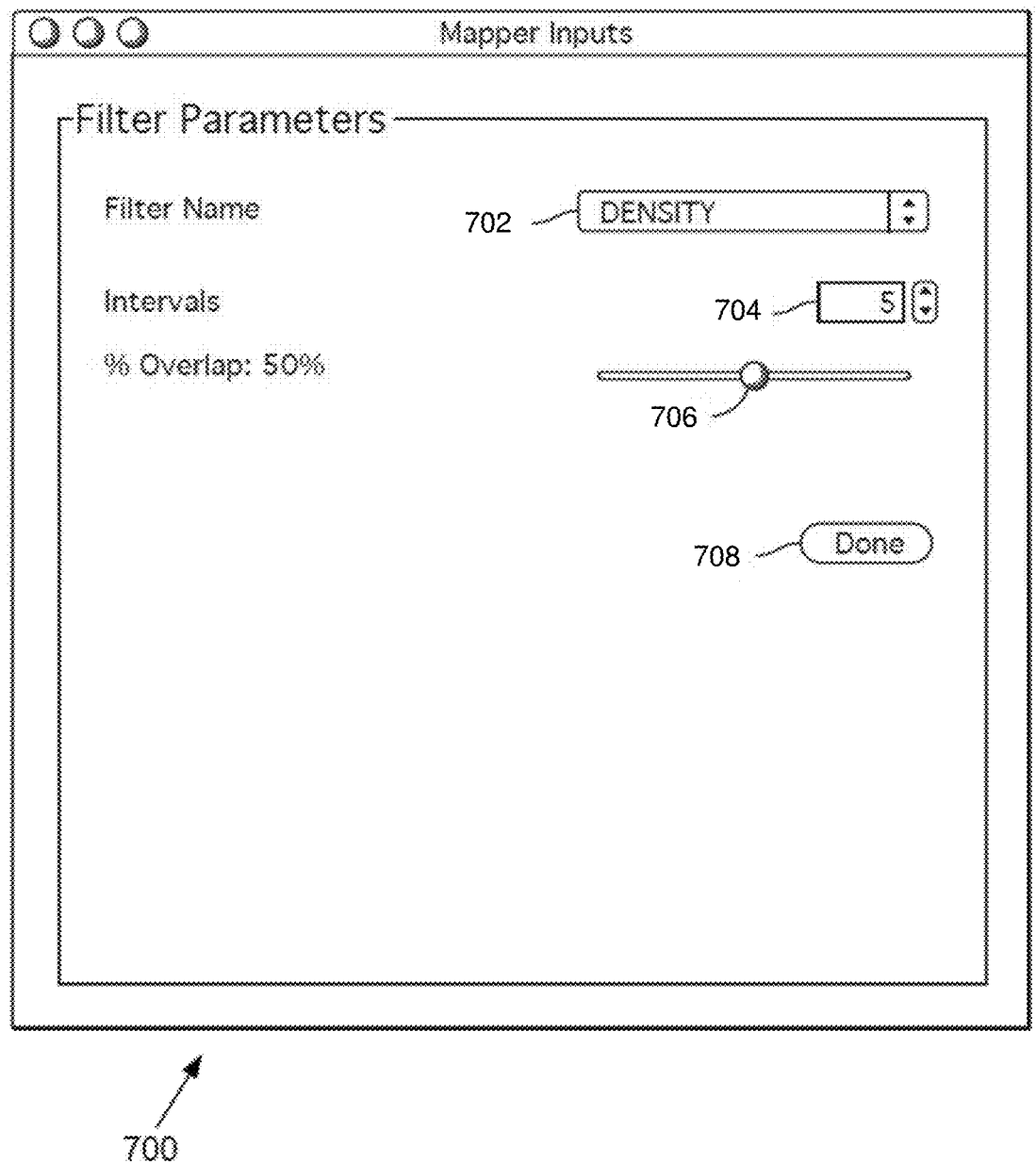
FIG. 7 is an example filter parameter interface window in some embodiments.

FIGS. 5-7 depict various interface windows to allow the user to make selections, enter information (e.g., fields, metrics, and filters), provide parameters (e.g., resolution), and provide data (e.g., identify the database) to be used with analysis. It will be appreciated that any graphical user interface or command line may be used to make selections, enter information, provide parameters, and provide data.

FIG. 5 is an example ID field selection interface window 500 in some embodiments. The ID field selection interface window 500 allows the user to identify an ID field. The ID field selection interface window 500 comprises a table search field 502, a table list 504, and a fields selection window 506.

In various embodiments, the input module 314 identifies and accesses a database from the database storage 324, user device 202a, or the data storage server 206. The input module 314 may then generate the ID field selection interface window 500 and provide a list of available tables of the selected database in the table list 504. The user may click on a table or search for a table by entering a search query (e.g., a keyword) in the table search field 502. Once a table is identified (e.g., clicked on by the user), the fields selection window 506 may provide a list of available fields in the selected table. The user may then choose a field from the fields selection window 506 to be the ID field. In some embodiments, any number of fields may be chosen to be the ID field(s).

FIG. 6A is an example data field selection interface window 600a in some embodiments. The data field selection interface window 600a allows the user to identify data fields. The data field selection interface window 600a comprises a table search field 502, a table list 504, a fields selection window 602, and a selected window 604.

In various embodiments, after selection of the ID field, the input module 314 provides a list of available tables of the selected database in the table list 504. The user may click on a table or search for a table by entering a search query (e.g., a keyword) in the table search field 502. Once a table is identified (e.g., clicked on by the user), the fields selection window 506 may provide a list of available fields in the selected table. The user may then choose any number of fields from the fields selection window 602 to be data fields. The selected data fields may appear in the selected window 604. The user may also deselect fields that appear in the selected window 604.

It will be appreciated that the table selected by the user in the table list 504 may be the same table selected with regard to FIG. 5. In some embodiments, however, the user may select a different table. Further, the user may, in various embodiments, select fields from a variety of different tables.

FIG. 6B is an example metric and filter selection interface window 600b in some embodiments. The metric and filter selection interface window 600b allows the user to identify a metric, add filter(s), and adjust filter parameters. The metric and filter selection interface window 600b comprises a metric pull down menu 606, an add filter from database button 608, and an add geometric filter button 610.

In various embodiments, the user may click on the metric pull down menu 606 to view a variety of metric options. Various metric options are described herein. In some embodiments, the user may define a metric. The user defined metric may then be used with the analysis.

In one example, finite metric space data may be constructed from a data repository (i.e., database, spreadsheet, or Matlab file). This may mean selecting a collection of fields whose entries will specify the metric using the standard Euclidean metric for these fields, when they are floating point or integer variables. Other notions of distance, such as graph distance between collections of points, may be supported.

The analysis module 320 may perform analysis using the metric as a part of a distance function. The distance function can be expressed by a formula, a distance matrix, or other routine which computes it. The user may add a filter from a database by clicking on the add filter from database button 608. The metric space may arise from a relational database, a Matlab file, an Excel spreadsheet, or other methods for storing and manipulating data. The metric and filter selection interface window 600b may allow the user to browse for other filters to use in the analysis. The analysis and metric function are further described in FIG. 8.

The user may also add a geometric filter 610 by clicking on the add geometric filter button 610. In various embodiments, the metric and filter selection interface window 600b may provide a list of geometric filters from which the user may choose.

FIG. 7 is an example filter parameter interface window 700 in some embodiments. The filter parameter interface window 700 allows the user to determine a resolution for one or more selected filters (e.g., filters selected in the metric and filter selection interface window 600). The filter parameter interface window 700 comprises a filter name menu 702, an interval field 704, an overlap bar 706, and a done button 708.

The filter parameter interface window 700 allows the user to select a filter from the filter name menu 702. In some embodiments, the filter name menu 702 is a drop down box indicating all filters selected by the user in the metric and filter selection interface window 600. Once a filter is chosen, the name of the filter may appear in the filter name menu 702. The user may then change the intervals and overlap for one, some, or all selected filters.

The interval field 704 allows the user to define a number of intervals for the filter identified in the filter name menu 702. The user may enter a number of intervals or scroll up or down to get to a desired number of intervals. Any number of intervals may be selected by the user. The function of the intervals is further discussed in FIG. 8.

The overlap bar 706 allows the user to define the degree of overlap of the intervals for the filter identified in the filter name menu 702. In one example, the overlap bar 706 includes a slider that allows the user to define the percentage overlap for the interval to be used with the identified filter. Any percentage overlap may be set by the user.

Once the intervals and overlap are defined for the desired filters, the user may click the done button. The user may then go back to the metric and filter selection interface window 600 and see a new option to run the analysis. In some embodiments, the option to run the analysis may be available in the filter parameter interface window 700. Once the analysis is complete, the result may appear in an interactive visualization which is further described in FIGS. 9-11.

It will be appreciated that that interface windows in FIGS. 4-7 are example. The example interface windows are not limited to the functional objects (e.g., buttons, pull down menus, scroll fields, and search fields) shown. Any number of different functional objects may be used. Further, as described herein, any other interface, command line, or graphical user interface may be used.

Figure 8:
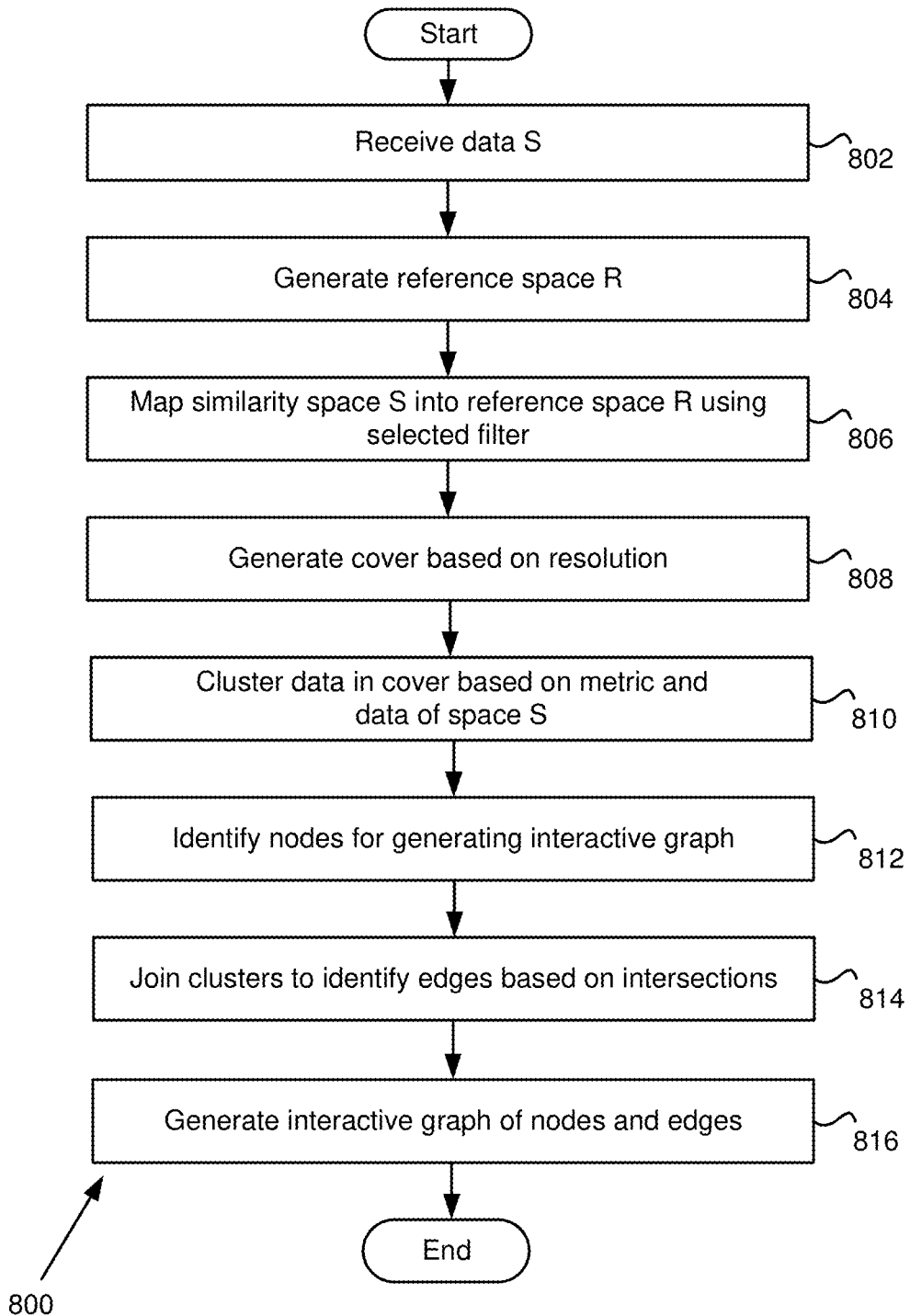
FIG. 8 is a flowchart for data analysis and generating a visualization in some embodiments.

FIG. 8 is a flowchart 800 for data analysis and generating an interactive visualization in some embodiments. In various embodiments, the processing on data and user-specified options is motivated by techniques from topology and, in some embodiments, algebraic topology. These techniques may be robust and general. In one example, these techniques apply to almost any kind of data for which some qualitative idea of "closeness" or "similarity" exists. The techniques discussed herein may be robust because the results may be relatively insensitive to noise in the data, user options, and even to errors in the specific details of the qualitative measure of similarity, which, in some embodiments, may be generally refer to as "the distance function" or "metric." It will be appreciated that while the description of the algorithms below may seem general, the implementation of techniques described herein may apply to any level of generality.

In step 802, the input module 314 receives data S. In one example, a user identifies a data structure and then identifies ID and data fields. Data S may be based on the information within the ID and data fields. In various embodiments, data S is treated as being processed as a finite "similarity space," where data S has a real-valued function d defined on pairs of points s and t in S, such that:

$d(s, s)=0$ $d(s, t)=d(t, s)$ $d(s, t)>=0$

These conditions may be similar to requirements for a finite metric space, but the conditions may be weaker. In various examples, the function is a metric.

It will be appreciated that data S may be a finite metric space, or a generalization thereof, such as a graph or weighted graph. In some embodiments, data S be specified by a formula, an algorithm, or by a distance matrix which specifies explicitly every pairwise distance.

In step 804, the input module 314 generates reference space R. In one example, reference space R may be a well-known metric space (e.g., such as the real line). The reference space R may be defined by the user. In step 806, the analysis module 320 generates a map ref( ) from S into R. The map ref( ) from S into R may be called the "reference map."

In one example, a reference of map from S is to a reference metric space R. R may be Euclidean space of some dimension, but it may also be the circle, torus, a tree, or other metric space. The map can be described by one or more filters (i.e., real valued functions on S). These filters can be defined by geometric invariants, such as the output of a density estimator, a notion of data depth, or functions specified by the origin of S as arising from a data set.

In step 808, the resolution module 218 generates a cover of R based on the resolution received from the user (e.g., filter(s), intervals, and overlap—see FIG. 7). The cover of R may be a finite collection of open sets (in the metric of R) such that every point in R lies in at least one of these sets. In various examples, R is k-dimensional Euclidean space, where k is the number of filter functions. More precisely in this example, R is a box in k-dimensional Euclidean space given by the product of the intervals [min_k, max_k], where min_k is the minimum value of the k-th filter function on S, and max_k is the maximum value.

For example, suppose there are 2 filter functions, F1 and F2, and that F1's values range from −1 to +1, and F2's values range from 0 to 5. Then the reference space is the rectangle in the x/y plane with corners (−1,0), (1,0), (−1, 5), (1, 5), as every point s of S will give rise to a pair (F1(s), F2(s)) that lies within that rectangle.

In various embodiments, the cover of R is given by taking products of intervals of the covers of [min_k,max_k] for each of the k filters. In one example, if the user requests 2 intervals and a 50% overlap for F1, the cover of the interval [−1,+1] will be the two intervals (−1.5, 0.5), (−0.5, 1.5). If the user requests 5 intervals and a 30% overlap for F2, then that cover of [0, 5] will be (−0.3, 1.3), (0.7, 2.3), (1.7, 3.3), (2.7, 4.3), (3.7, 5.3). These intervals may give rise to a cover of the 2-dimensional box by taking all possible pairs of intervals where the first of the pair is chosen from the cover for F1 and the second from the cover for F2. This may give rise to 2*5, or 10, open boxes that covered the 2-dimensional reference space. However, it will be appreciated that the intervals may not be uniform, or that the covers of a k-dimensional box may not be constructed by products of intervals. In some embodiments, there are many other choices of intervals. Further, in various embodiments, a wide range of covers and/or more general reference spaces may be used.

In one example, given a cover, C1, . . . , Cm, of R, the reference map is used to assign a set of indices to each point in S, which are the indices of the Cj such that ref(s) belongs to Cj. This function may be called ref tags(s). In a language such as Java, ref tags would be a method that returned an int[ ]. Since the C's cover R in this example, ref(s) must lie in at least one of them, but the elements of the cover usually overlap one another, which means that points that "land near the edges" may well reside in multiple cover sets. In considering the two filter example, if F1(s) is −0.99, and F2(s) is 0.001, then ref(s) is (−0.99, 0.001), and this lies in the cover element (−1.5, 0.5)×(−0.3,1.3). Supposing that was labeled C1, the reference map may assign s to the set {1}. On the other hand, if t is mapped by F1, F2 to (0.1, 2.1), then ref(t) will be in (−1.5,0.5)×(0.7, 2.3), (−0.5, 1.5)×(0.7, 2.3), (−1.5,0.5)×(1.7,3.3), and (−0.5, 1.5)×(1.7,3.3), so the set of indices would have four elements for t.

Having computed, for each point, which "cover tags" it is assigned to, for each cover element, Cd, the points may be constructed, whose tags include d, as set S(d). This may mean that every point s is in S(d) for some d, but some points may belong to more than one such set. In some embodiments, there is, however, no requirement that each S(d) is non-empty, and it is frequently the case that some of these sets are empty. In the non-parallelized version of some embodiments, each point x is processed in turn, and x is inserted into a hash-bucket for each j in ref tags(t) (that is, this may be how S(d) sets are computed).

It will be appreciated that the cover of the reference space R may be controlled by the number of intervals and the overlap identified in the resolution (e.g., see FIG. 7). For example, the more intervals, the finer the resolution in S—that is, the fewer points in each S(d), but the more similar (with respect to the filters) these points may be. The greater the overlap, the more times that clusters in S(d) may intersect clusters in S(e)—this means that more "relationships" between points may appear, but, in some embodiments, the greater the overlap, the more likely that accidental relationships may appear.

In step 810, the analysis module 320 clusters each S(d) based on the metric, filter, and the space S. In some embodiments, a dynamic single-linkage clustering algorithm may be used to partition S(d). It will be appreciated that any number of clustering algorithms may be used with embodiments discussed herein. For example, the clustering scheme may be k-means clustering for some k, single linkage clustering, average linkage clustering, or any method specified by the user.

The significance of the user-specified inputs may now be seen. In some embodiments, a filter may amount to a "forced stretching" in a certain direction. In some embodiments, the analysis module 320 may not cluster two points unless ALL of the filter values are sufficiently "related" (recall that while normally related may mean "close," the cover may impose a much more general relationship on the filter values, such as relating two points s and t if ref(s) and ref(t) are sufficiently close to the same circle in the plane). In various embodiments, the ability of a user to impose one or more "critical measures" makes this technique more powerful than regular clustering, and the fact that these filters can be anything, is what makes it so general.

The output may be a simplicial complex, from which one can extract its 1-skeleton. The nodes of the complex may be partial clusters, (i.e., clusters constructed from subsets of S specified as the preimages of sets in the given covering of the reference space R).

In step 812, the visualization engine 322 identifies nodes which are associated with a subset of the partition elements of all of the S(d) for generating an interactive visualization. For example, suppose that S={1, 2, 3, 4}, and the cover is C1, C2, C3. Then if ref tags(1)={1, 2, 3} and ref tags(2)={2, 3}, and ref tags(3)={3}, and finally ref tags(4)={1, 3}, then S(1) in this example is {1, 4}, S(2)={1,2}, and S(3)={1,2, 3,4}. If 1 and 2 are close enough to be clustered, and 3 and 4 are, but nothing else, then the clustering for S(1) may be {1} {3}, and for S(2) it may be {1,2}, and for S(3) it may be {1,2},{3,4}. So the generated graph has, in this example, at most four nodes, given by the sets {1},{4}, {1,2}, and {3,4} (note that {1,2} appears in two different clusterings). Of the sets of points that are used, two nodes intersect provided that the associated node sets have a non-empty intersection (although this could easily be modified to allow users to require that the intersection is "large enough" either in absolute or relative terms).

Nodes may be eliminated for any number of reasons. For example, a node may be eliminated as having too few points and/or not being connected to anything else. In some embodiments, the criteria for the elimination of nodes (if any) may be under user control or have application-specific requirements imposed on it. For example, if the points are consumers, for instance, clusters with too few people in area codes served by a company could be eliminated. If a cluster was found with "enough" customers, however, this might indicate that expansion into area codes of the other consumers in the cluster could be warranted.

In step 814, the visualization engine 322 joins clusters to identify edges (e.g., connecting lines between nodes). Once the nodes are constructed, the intersections (e.g., edges) may be computed "all at once," by computing, for each point, the set of node sets (not ref tags, this time). That is, for each s in S, node_id_set(s) may be computed, which is an int[ ]. In some embodiments, if the cover is well behaved, then this operation is linear in the size of the set S, and we then iterate over each pair in node_id_set(s). There may be an edge between two node_id's if they both belong to the same node_id_set( ) value, and the number of points in the intersection is precisely the number of different node_id sets in which that pair is seen. This means that, except for the clustering step (which is often quadratic in the size of the sets S(d), but whose size may be controlled by the choice of cover), all of the other steps in the graph construction algorithm may be linear in the size of S, and may be computed quite efficiently.

Figure 10:
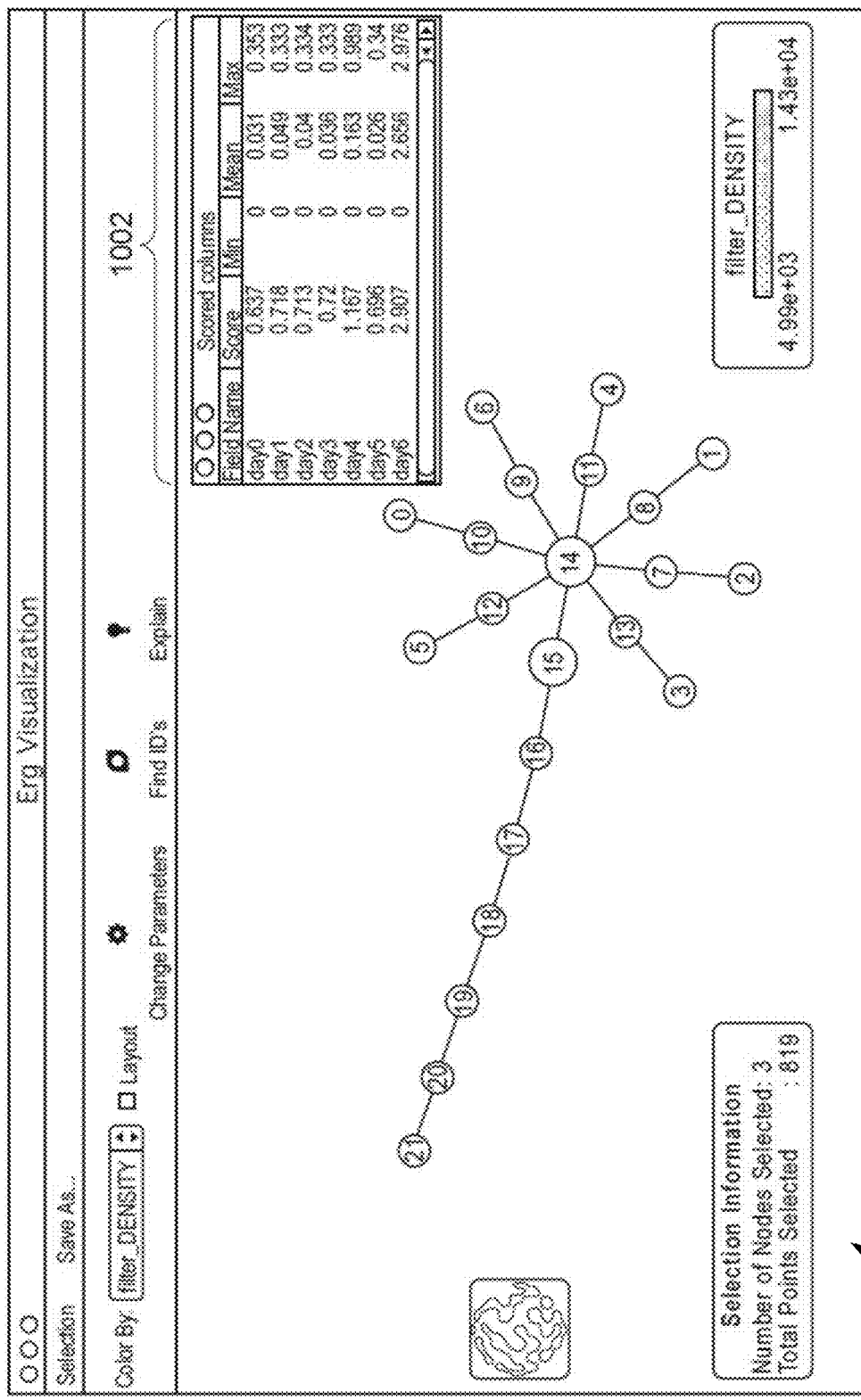
FIG. 10 is an example interactive visualization displaying an explain information window in some embodiments.
Figure 11:
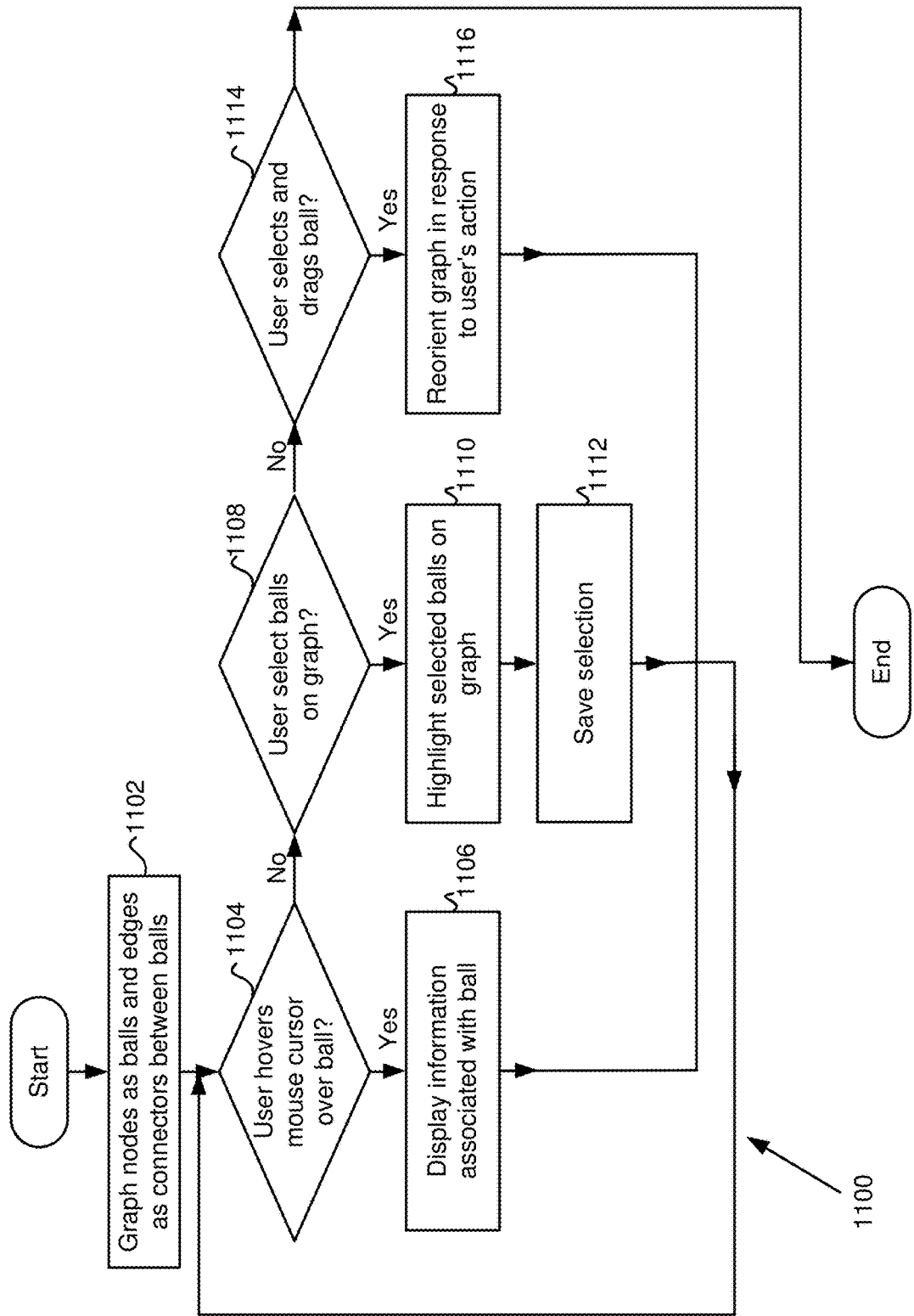
FIG. 11 is a flowchart of functionality of the interactive visualization in some embodiments.

In step 816, the visualization engine 322 generates the interactive visualization of interconnected nodes (e.g., nodes and edges displayed in FIGS. 10 and 11).

It will be appreciated that it is possible, in some embodiments, to make sense in a fairly deep way of connections between various ref( ) maps and/or choices of clustering. Further, in addition to computing edges (pairs of nodes), the embodiments described herein may be extended to compute triples of nodes, etc. For example, the analysis module 320 may compute simplicial complexes of any dimension (by a variety of rules) on nodes, and apply techniques from homology theory to the graphs to help users understand a structure in an automatic (or semi-automatic) way.

Further, it will be appreciated that uniform intervals in the covering may not always be a good choice. For example, if the points are exponentially distributed with respect to a given filter, uniform intervals can fail—in such case adaptive interval sizing may yield uniformly-sized S(d) sets, for instance.

Further, in various embodiments, an interface may be used to encode techniques for incorporating third-party extensions to data access and display techniques. Further, an interface may be used to for third-party extensions to underlying infrastructure to allow for new methods for generating coverings, and defining new reference spaces.

Figure 9:
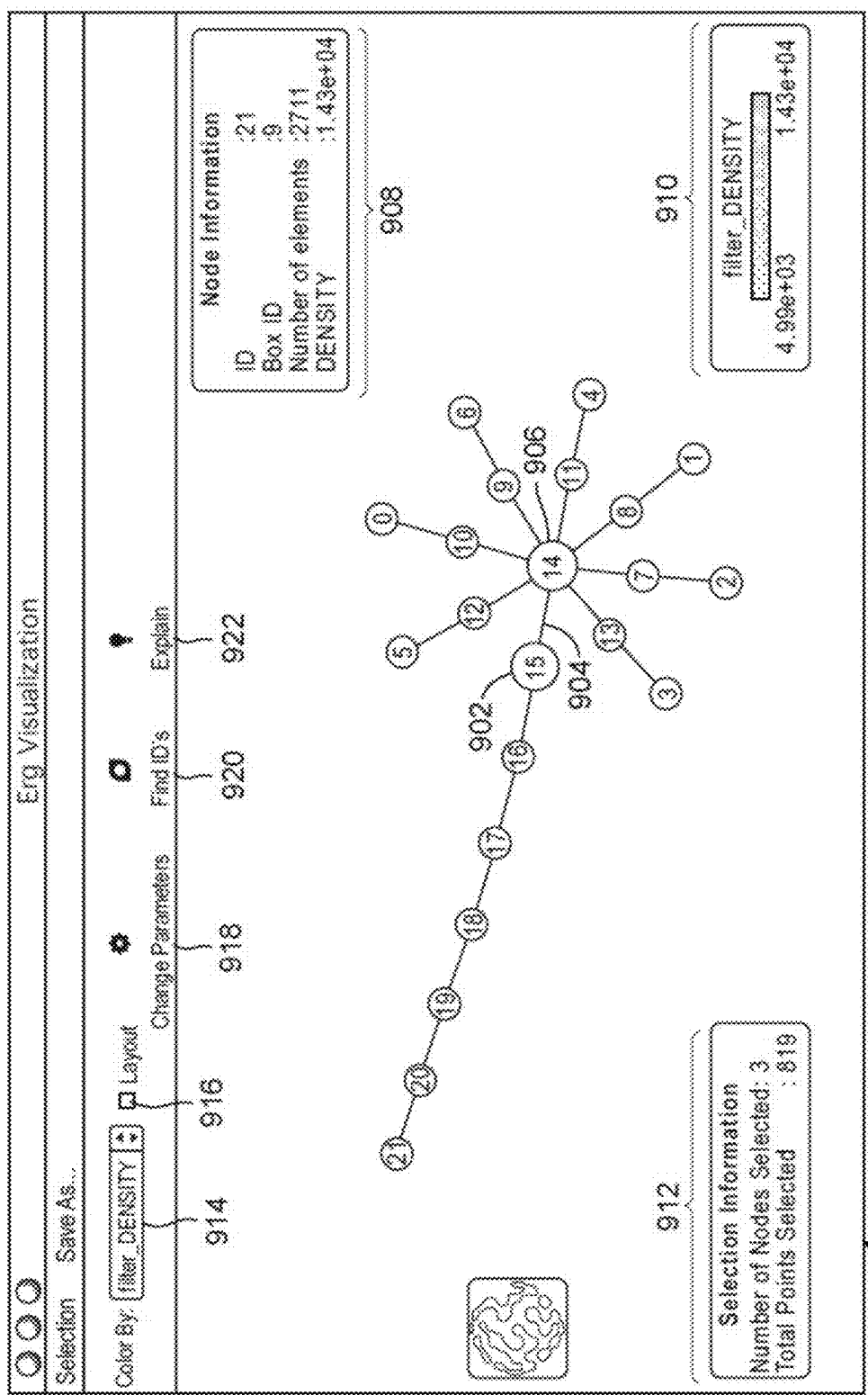
FIG. 9 is an example interactive visualization in some embodiments.

FIG. 9 is an example interactive visualization 900 in some embodiments. The display of the interactive visualization may be considered a "graph" in the mathematical sense. The interactive visualization comprises of two types of objects: nodes (e.g., nodes 902 and 906) (the colored balls) and the edges (e.g., edge 904) (the black lines). The edges connect pairs of nodes (e.g., edge 904 connects node 902 with node 906). As discussed herein, each node may represent a collection of data points (rows in the database identified by the user). In one example, connected nodes tend to include data points which are "similar to" (e.g., clustered with) each other. The collection of data points may be referred to as being "in the node." The interactive visualization may be two-dimensional, three-dimensional, or a combination of both.

In various embodiments, connected nodes and edges may form a graph or structure. There may be multiple graphs in the interactive visualization. In one example, the interactive visualization may display two or more unconnected structures of nodes and edges.

The visual properties of the nodes and edges (such as, but not limited to, color, stroke color, text, texture, shape, coordinates of the nodes on the screen) can encode any data based property of the data points within each node. For example, coloring of the nodes and/or the edges may indicate (but is not limited to) the following:

Values of fields or filters
Any general functions of the data in the nodes (e.g., if the data were unemployment rates by state, then GDP of the states may be identifiable by color the nodes)
Number of data points in the node The interactive visualization 900 may contain a "color bar" 910 which may comprise a legend indicating the coloring of the nodes (e.g., balls) and may also identify what the colors indicate. For example, in FIG. 9, color bar 910 indicates that color is based on the density filter with blue (on the far left of the color bar 910) indicating "4.99e+03" and red (on the far right of the color bar 910) indicating "1.43e+04." In general this might be expanded to show any other legend by which nodes and/or edges are colored. It will be appreciated that the, In some embodiments, the user may control the color as well as what the color (and/or stroke color, text, texture, shape, coordinates of the nodes on the screen) indicates.

The user may also drag and drop objects of the interactive visualization 900. In various embodiments, the user may reorient structures of nodes and edges by dragging one or more nodes to another portion of the interactive visualization (e.g., a window). In one example, the user may select node 902, hold node 902, and drag the node across the window. The node 902 will follow the user's cursor, dragging the structure of edges and/or nodes either directly or indirectly connected to the node 902. In some embodiments, the interactive visualization 900 may depict multiple unconnected structures. Each structure may include nodes, however, none of the nodes of either structure are connected to each other. If the user selects and drags a node of the first structure, only the first structure will be reoriented with respect to the user action. The other structure will remain unchanged. The user may wish to reorient the structure in order to view nodes, select nodes, and/or better understand the relationships of the underlying data.

In one example, a user may drag a node to reorient the interactive visualization (e.g., reorient the structure of nodes and edges). While the user selects and/or drags the node, the nodes of the structure associated with the selected node may move apart from each other in order to provide greater visibility. Once the user lets go (e.g., deselects or drops the node that was dragged), the nodes of the structure may continue to move apart from each other.

In various embodiments, once the visualization module 322 generates the interactive display, the depicted structures may move by spreading out the nodes from each other. In one example, the nodes spread from each other slowly allowing the user to view nodes distinguish from each other as well as the edges. In some embodiments, the visualization module 322 optimizes the spread of the nodes for the user's view. In one example, the structure(s) stop moving once an optimal view has been reached.

It will be appreciated that the interactive visualization 900 may respond to gestures (e.g., multitouch), stylus, or other interactions allowing the user to reorient nodes and edges and/or interacting with the underlying data.

The interactive visualization 900 may also respond to user actions such as when the user drags, clicks, or hovers a mouse cursor over a node. In some embodiments, when the user selects a node or edge, node information or edge information may be displayed. In one example, when a node is selected (e.g., clicked on by a user with a mouse or a mouse cursor hovers over the node), a node information box 908 may appear that indicates information regarding the selected node. In this example, the node information box 908 indicates an ID, box ID, number of elements (e.g., data points associated with the node), and density of the data associated with the node.

The user may also select multiple nodes and/or edges by clicking separate on each object, or drawing a shape (such as a box) around the desired objects. Once the objects are selected, a selection information box 912 may display some information regarding the selection. For example, selection information box 912 indicates the number of nodes selected and the total points (e.g., data points or elements) of the selected nodes.

The interactive visualization 900 may also allow a user to further interact with the display. Color option 914 allows the user to display different information based on color of the objects. Color option 914 in FIG. 9 is set to filter_Density, however, other filters may be chosen and the objects recolored based on the selection. It will be appreciated that the objects may be colored based on any filter, property of data, or characterization. When a new option is chosen in the color option 914, the information and/or colors depicted in the color bar 910 may be updated to reflect the change.

Layout checkbox 914 may allow the user to anchor the interactive visualization 900. In one example, the layout checkbox 914 is checked indicating that the interactive visualization 900 is anchored. As a result, the user will not be able to select and drag the node and/or related structure. Although other functions may still be available, the layout checkbox 914 may help the user keep from accidentally moving and/or reorienting nodes, edges, and/or related structures. It will be appreciated that the layout checkbox 914 may indicate that the interactive visualization 900 is anchored when the layout checkbox 914 is unchecked and that when the layout checkbox 914 is checked the interactive visualization 900 is no longer anchored.

The change parameters button 918 may allow a user to change the parameters (e.g., add/remove filters and/or change the resolution of one or more filters). In one example, when the change parameters button 918 is activated, the user may be directed back to the metric and filter selection interface window 600 (see FIG. 6) which allows the user to add or remove filters (or change the metric). The user may then view the filter parameter interface 700 (see FIG. 7) and change parameters (e.g., intervals and overlap) for one or more filters. The analysis module 320 may then re-analyze the data based on the changes and display a new interactive visualization 900 without again having to specify the data sets, filters, etc.

The find ID's button 920 may allow a user to search for data within the interactive visualization 900. In one example, the user may click the find ID's button 920 and receive a window allowing the user to identify data or identify a range of data. Data may be identified by ID or searching for the data based on properties of data and/or metadata. If data is found and selected, the interactive visualization 900 may highlight the nodes associated with the selected data. For example, selecting a single row or collection of rows of a database or spreadsheet may produce a highlighting of nodes whose corresponding partial cluster contains any element of that selection.

In various embodiments, the user may select one or more objects and click on the explain button 922 to receive in-depth information regarding the selection. In some embodiments, when the user selects the explain button 922, the information about the data from which the selection is based may be displayed. The function of the explain button 922 is further discussed with regard to FIG. 10.

In various embodiments, the interactive visualization 900 may allow the user to specify and identify subsets of interest, such as output filtering, to remove clusters or connections which are too small or otherwise uninteresting. Further, the interactive visualization 900 may provide more general coloring and display techniques, including, for example, allowing a user to highlight nodes based on a user-specified predicate, and coloring the nodes based on the intensity of user-specified weighting functions.

The interactive visualization 900 may comprise any number of menu items. The "Selection" menu may allow the following functions:

Select singletons (select nodes which are not connected to other nodes)
Select all (selects all the nodes and edges)
Select all nodes (selects all nodes)
Select all edges
Clear selection (no selection)
Invert Selection (selects the complementary set of nodes or edges)
Select "small" nodes (allows the user to threshold nodes based on how many points they have)
Select leaves (selects all nodes which are connected to long "chains" in the graph)
Remove selected nodes
Show in a table (shows the selected nodes and their associated data in a table)

Save selected nodes (saves the selected data to whatever format the user chooses. This may allow the user to subset the data and create new datasources which may be used for further analysis.)

In one example of the "show in a table" option, information from a selection of nodes may be displayed. The information may be specific to the origin of the data. In various embodiments, elements of a database table may be listed, however, other methods specified by the user may also be included. For example, in the case of microarray data from gene expression data, heat maps may be used to view the results of the selections.

The interactive visualization 900 may comprise any number of menu items. The "Save" menu may allow may allow the user to save the whole output in a variety of different formats such as (but not limited to):

Image files (PNG/JPG/PDF/SVG etc.)

Binary output (The interactive output is saved in the binary format. The user may reopen this file at any time to get this interactive window again)

In some embodiments, graphs may be saved in a format such that the graphs may be used for presentations. This may include simply saving the image as a pdf or png file, but it may also mean saving an executable .xml file, which may permit other users to use the search and save capability to the database on the file without having to recreate the analysis.

In various embodiments, a relationship between a first and a second analysis output/interactive visualization for differing values of the interval length and overlap percentage may be displayed. The formal relationship between the first and second analysis output/interactive visualization may be that when one cover refines the next, there is a map of simplicial complexes from the output of the first to the output of the second. This can be displayed by applying a restricted form of a three-dimensional graph embedding algorithm, in which a graph is the union of the graphs for the various parameter values and in which the connections are the connections in the individual graphs as well as connections from one node to its image in the following graph. The constituent graphs may be placed in its own plane in 3D space. In some embodiments, there is a restriction that each constituent graph remain within its associated plane. Each constituent graph may be displayed individually, but a small change of parameter value may result in the visualization of the adjacent constituent graph. In some embodiments, nodes in the initial graph will move to nodes in the next graph, in a readily visualizable way.

FIG. 10 is an example interactive visualization 1000 displaying an explain information window 1002 in some embodiments. In various embodiments, the user may select a plurality of nodes and click on the explain button. When the explain button is clicked, the explain information window 1002 may be generated. The explain information window 1002 may identify the data associated with the selected object(s) as well as information (e.g., statistical information) associated with the data.

In some embodiments, the explain button allows the user to get a sense for which fields within the selected data fields are responsible for "similarity" of data in the selected nodes and the differentiating characteristics. There can be many ways of scoring the data fields. The explain information window 1002 (i.e., the scoring window in FIG. 10) is shown along with the selected nodes. The highest scoring fields may distinguish variables with respect to the rest of the data.

In one example, the explain information window 1002 indicates that data from fields day0-day6 has been selected. The minimum value of the data in all of the fields is 0. The explain information window 1002 also indicates the maximum values. For example, the maximum value of all of the data associated with the day0 field across all of the points of the selected nodes is 0.353. The average (i.e., mean) of all of the data associated with the day0 field across all of the points of the selected nodes is 0.031. The score may be a relative (e.g., normalized) value indicating the relative function of the filter; here, the score may indicate the relative density of the data associated with the day0 field across all of the points of the selected nodes. It will be appreciated that any information regarding the data and/or selected nodes may appear in the explain information window 1002.

It will be appreciated that the data and the interactive visualization 1000 may be interacted with in any number of ways. The user may interact with the data directly to see where the graph corresponds to the data, make changes to the analysis and view the changes in the graph, modify the graph and view changes to the data, or perform any kind of interaction.

FIG. 11 is a flowchart 1200 of functionality of the interactive visualization in some embodiments. In step 1202, the visualization engine 322 receives the analysis from the analysis module 320 and graphs nodes as balls and edges as connectors between balls 1202 to create interactive visualization 900 (see FIG. 9).

In step 1204, the visualization engine 322 determines if the user is hovering a mouse cursor (or has selected) a ball (i.e., a node). If the user is hovering a mouse cursor over a ball or selecting a ball, then information is displayed regarding the data associated with the ball. In one example, the visualization engine 322 displays a node information window 908.

If the visualization engine 322 does not determine that the user is hovering a mouse cursor (or has selected) a ball, then the visualization engine 322 determines if the user has selected balls on the graph (e.g., by clicking on a plurality of balls or drawing a box around a plurality of balls). If the user has selected balls on the graph, the visualization engine 322 may highlight the selected balls on the graph in step 1110. The visualization engine 322 may also display information regarding the selection (e.g., by displaying a selection information window 912). The user may also click on the explain button 922 to receive more information associated with the selection (e.g., the visualization engine 322 may display the explain information window 1002).

In step 1112, the user may save the selection. For example, the visualization engine 322 may save the underlying data, selected metric, filters, and/or resolution. The user may then access the saved information and create a new structure in another interactive visualization 900 thereby allowing the user to focus attention on a subset of the data.

If the visualization engine 322 does not determine that the user has selected balls on the graph, the visualization engine 322 may determine if the user selects and drags a ball on the graph in step 1114. If the user selects and drags a ball on the graph, the visualization engine 322 may reorient the selected balls and any connected edges and balls based on the user's action in step 1116. The user may reorient all or part of the structure at any level of granularity.

It will be appreciated that although FIG. 11 discussed the user hovering over, selecting, and/or dragging a ball, the user may interact with any object in the interactive visualization 900 (e.g., the user may hover over, select, and/or drag an edge). The user may also zoom in or zoom out using the interactive visualization 900 to focus on all or a part of the structure (e.g., one or more balls and/or edges).

Further, although balls are discussed and depicted in FIGS. 9-11, it will be appreciated that the nodes may be any shape and appear as any kind of object. Further, although some embodiments described herein discuss an interactive visualization being generated based on the output of algebraic topology, the interactive visualization may be generated based on any kind of analysis and is not limited.

For years, researchers have been collecting huge amounts of data on breast cancer, yet we are still battling the disease. Complexity, rather than quantity, is one of the fundamental issues in extracting knowledge from data. A topological data exploration and visualization platform may assist the analysis and assessment of complex data. In various embodiments, a predictive and visual cancer map generated by the topological data exploration and visualization platform may assist physicians to determine treatment options.

In one example, a breast cancer map visualization may be generated based on the large amount of available information already generated by many researchers. Physicians may send biopsy data directly to a cloud-based server which may localize a new patient's data within the breast cancer map visualization. The breast cancer map visualization may be annotated (e.g., labeled) such that the physician may view outcomes of patients with similar profiles as well as different kinds of statistical information such as survival probabilities. Each new data point from a patient may be incorporated into the breast cancer map visualization to improve accuracy of the breast cancer map visualization over time.

Although the following examples are largely focused on cancer map visualizations, it will be appreciated that at least some of the embodiments described herein may apply to any biological condition and not be limited to cancer and/or disease. For example, some embodiments, may apply to different industries.

Figure 12:
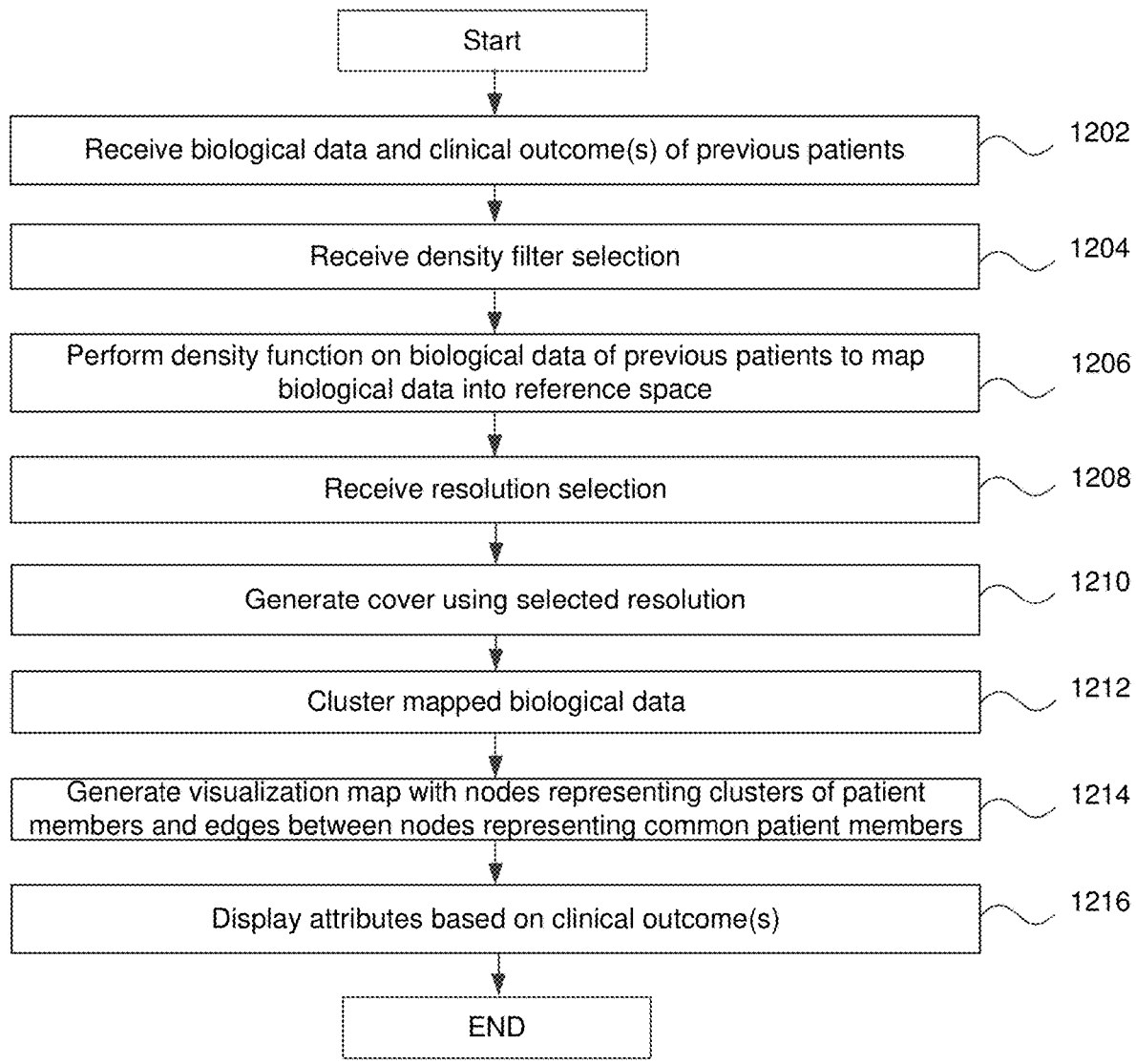
FIG. 12 is a flowchart of for generating a cancer map visualization utilizing biological data of a plurality of patients in some embodiments.

FIG. 12 is a flowchart for generating a cancer map visualization utilizing biological data of a plurality of patients in some embodiments. In various embodiments, the processing of data and user-specified options is motivated by techniques from topology and, in some embodiments, algebraic topology. As discussed herein, these techniques may be robust and general. In one example, these techniques apply to almost any kind of data for which some qualitative idea of "closeness" or "similarity" exists. It will be appreciated that the implementation of techniques described herein may apply to any level of generality.

In various embodiments, a cancer map visualization is generated using genomic data linked to clinical outcomes (i.e., medical characteristics) which may be used by physicians during diagnosis and/or treatment. Initially, publicly available data sets may be integrated to construct the topological map visualizations of patients (e.g., breast cancer patients). It will be appreciated that any private, public, or combination of private and public data sets may be integrated to construct the topological map visualizations. A map visualization may be based on biological data such as, but not limited to, gene expression, sequencing, and copy number variation. As such, the map visualization may comprise many patients with many different types of collected data. Unlike traditional methods of analysis where distinct studies of breast cancer appear as separate entities, the map visualization may fuse disparate data sets while utilizing many datasets and data types.

In various embodiments, a new patient may be localized on the map visualization. With the map visualization for subtypes of a particular disease and a new patient diagnosed with the disease, point(s) may be located among the data points used in computing the map visualization (e.g., nearest neighbor) which is closest to the new patient point. The new patient may be labeled with nodes in the map visualization containing the closest neighbor. These nodes may be highlighted to give a physician the location of the new patient among the patients in the reference data set. The highlighted nodes may also give the physician the location of the new patient relative to annotated disease subtypes. Nearest neighbor is further described in U.S. Non-Provisional patent application Ser. No. 13/648,237 filed Oct. 9, 2012 and entitled "Systems and Methods for Mapping New Patient Information to Historic Outcomes for Treatment Assistance," the entirety of which is incorporated herein by reference.

The visualization map may be interactive and/or searchable in real-time thereby potentially enabling extended analysis and providing speedy insight into treatment.

In step 1202, biological data and clinical outcomes of previous patients may be received. The clinical outcomes may be medical characteristics. Biological data is any data that may represent a condition (e.g., a medical condition) of a person. Biological data may include any health related, medical, physical, physiological, pharmaceutical data associated with one or more patients. In one example, biological data may include measurements of gene expressions for any number of genes. In another example, biological data may include sequencing information (e.g., RNA sequencing).

In various embodiments, biological data for a plurality of patients may be publicly available. For example, various medical health facilities and/or public entities may provide gene expression data for a variety of patients. In addition to the biological data, information regarding any number of clinical outcomes, treatments, therapies, diagnoses and/or prognoses may also be provided. It will be appreciated that any kind of information may be provided in addition to the biological data.

The biological data, in one example, may be similar to data S as discussed with regard to step 802 of FIG. 8. The biological data may include ID fields that identify patients and data fields that are related to the biological information (e.g., gene expression measurements).

FIG. 13 is an example data structure 1302 including biological data 1304*a*-1304*y* for a number of patients 1308*a*-1308*n* that may be used to generate the cancer map visualization in some embodiments. Column 1302 represents different patient identifiers for different patients. The patient identifiers may be any identifier.

At least some biological data may be contained within gene expression measurements 1304*a*-1304*y*. In FIG. 13, "y" represents any number. For example, there may be 50,000 or more separate columns for different gene expressions related to a single patient or related to one or more samples from a patient. It will be appreciated that column 1304*a* may represent a gene expression measurement for each patient (if any for some patients) associated with the patient identifiers in column 1302. The column 1304*b* may represent a gene expression measurement of one or more genes that are different than that of column 1304*a*. As discussed, there may be any number of columns representing different gene expression measurements.

Column 1306 may include any number of clinical outcomes, prognoses, diagnoses, reactions, treatments, and/or any other information associated with each patient. All or some of the information contained in column 1306 may be displayed (e.g., by a label or an annotation that is displayed on the visualization or available to the user of the visualization via clicking) on or for the visualization.

Rows 1308*a*-1308*n* each contains biological data associated with the patient identifier of the row. For example, gene expressions in row 1308*a* are associated with patient identifier P1. As similarly discussed with regard to "y" herein, "n" represents any number. For example, there may be 100,000 or more separate rows for different patients.

It will be appreciated that there may be any number of data structures that contain any amount of biological data for any number of patients. The data structure(s) may be utilized to generate any number of map visualizations.

In step 1204, the analysis server may receive a filter selection. In some embodiments, the filter selection is a density estimation function. It will be appreciated that the filter selection may include a selection of one or more functions to generate a reference space.

In step 1206, the analysis server performs the selected filter(s) on the biological data of the previous patients to map the biological data into a reference space. In one example, a density estimation function, which is well known in the art, may be performed on the biological data (e.g., data associated with gene expression measurement data 1304*a*-1304*y*) to relate each patient identifier to one or more locations in the reference space (e.g., on a real line).

In step 1208, the analysis server may receive a resolution selection. The resolution may be utilized to identify overlapping portions of the reference space (e.g., a cover of the reference space R) in step 1210.

As discussed herein, the cover of R may be a finite collection of open sets (in the metric of R) such that every point in R lies in at least one of these sets. In various examples, R is k-dimensional Euclidean space, where k is the number of filter functions. It will be appreciated that the cover of the reference space R may be controlled by the number of intervals and the overlap identified in the resolution (e.g., see FIG. 7). For example, the more intervals, the finer the resolution in S (e.g., the similarity space of the received biological data)—that is, the fewer points in each S(d), but the more similar (with respect to the filters) these points may be. The greater the overlap, the more times that clusters in S(d) may intersect clusters in S(e)—this means that more "relationships" between points may appear, but, in some embodiments, the greater the overlap, the more likely that accidental relationships may appear.

In step 1212, the analysis server receives a metric to cluster the information of the cover in the reference space to partition S(d). In one example, the metric may be a Pearson Correlation. The clusters may form the groupings (e.g., nodes or balls). Various cluster means may be used including, but not limited to, a single linkage, average linkage, complete linkage, or k-means method.

As discussed herein, in some embodiments, the analysis module 320 may not cluster two points unless filter values are sufficiently "related" (recall that while normally related may mean "close," the cover may impose a much more general relationship on the filter values, such as relating two points s and t if ref(s) and ref(t) are sufficiently close to the same circle in the plane where ref( ) represents one or more filter functions). The output may be a simplicial complex, from which one can extract its 1-skeleton. The nodes of the complex may be partial clusters, (i.e., clusters constructed from subsets of S specified as the preimages of sets in the given covering of the reference space R).

In step 1214, the analysis server may generate the visualization map with nodes representing clusters of patient members and edges between nodes representing common patient members. In one example, the analysis server identifies nodes which are associated with a subset of the partition elements of all of the S(d) for generating an interactive visualization.

As discussed herein, for example, suppose that S={1, 2, 3, 4}, and the cover is C1, C2, C3. Suppose cover C1 contains {1, 4}, C2 contains {1,2}, and C3 contains {1,2,3,4}. If 1 and 2 are close enough to be clustered, and 3 and 4 are, but nothing else, then the clustering for S(1) may be {1}, {4}, and for S(2) it may be {1,2}, and for S(3) it may be {1,2}, {3,4}. So the generated graph has, in this example, at most four nodes, given by the sets {1}, {4}, {1, 2}, and {3, 4} (note that {1, 2} appears in two different clusterings). Of the sets of points that are used, two nodes intersect provided that the associated node sets have a non-empty intersection (although this could easily be modified to allow users to require that the intersection is "large enough" either in absolute or relative terms).

As a result of clustering, member patients of a grouping may share biological similarities (e.g., similarities based on the biological data).

The analysis server may join clusters to identify edges (e.g., connecting lines between nodes). Clusters joined by edges (i.e., interconnections) share one or more member patients. In step 1216, a display may display a visualization map with attributes based on the clinical outcomes contained in the data structures (e.g., see FIG. 13 regarding clinical outcomes). Any labels or annotations may be utilized based on information contained in the data structures. For example, treatments, prognoses, therapies, diagnoses, and the like may be used to label the visualization. In some embodiments, the physician or other user of the map visualization accesses the annotations or labels by interacting with the map visualization.

The resulting cancer map visualization may reveal interactions and relationships that were obscured, untested, and/or previously not recognized.

Figure 14:
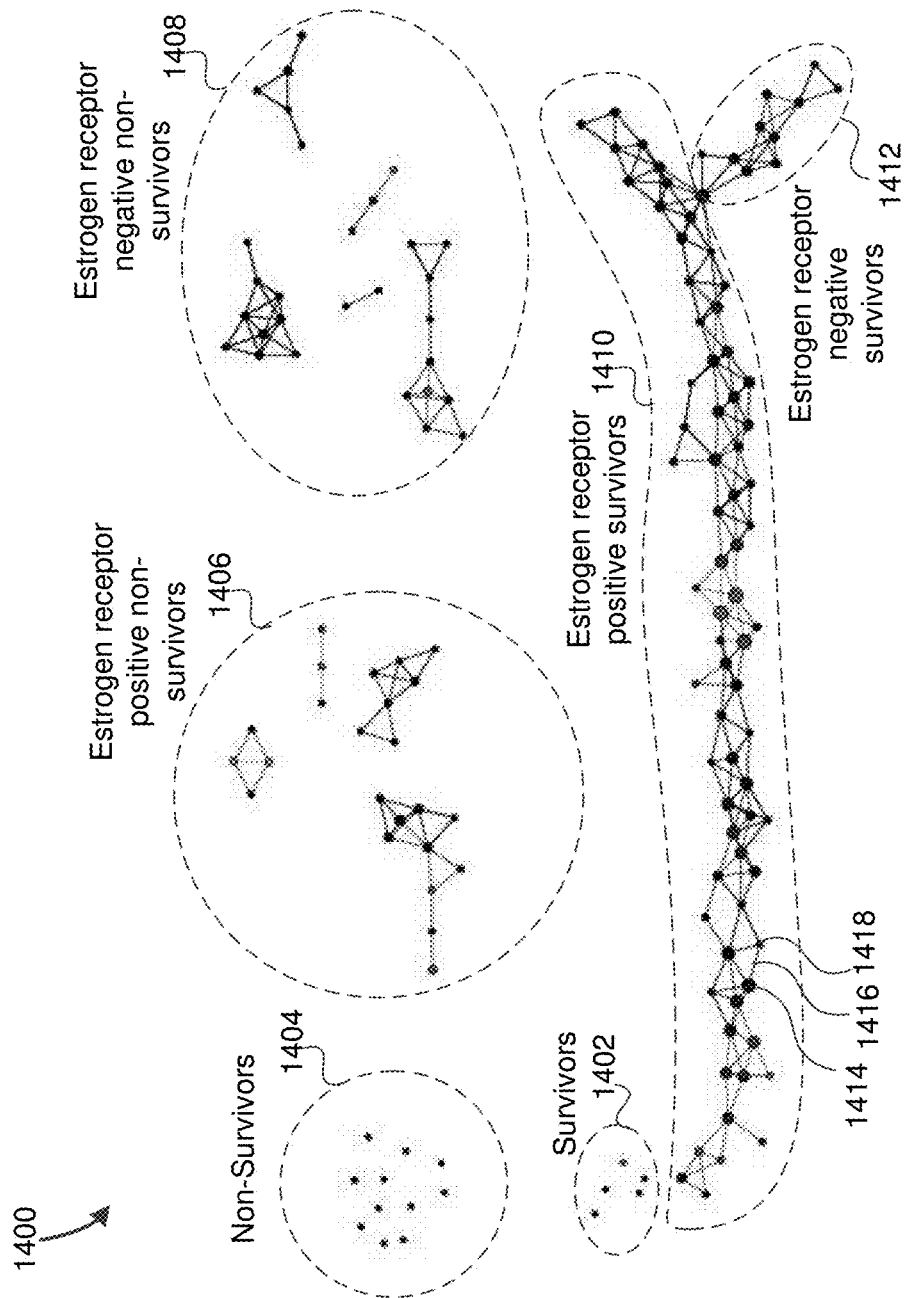
FIG. 14 is an example visualization displaying the cancer map in some embodiments.

FIG. 14 is an example visualization displaying the cancer map visualization 1400 in some embodiments. The cancer map visualization 1400 represents a topological network of cancer patients. The cancer map visualization 1400 may be based on publicly and/or privately available data.

In various embodiments, the cancer map visualization 1400 is created using gene expression profiles of excised tumors. Each node (i.e., ball or grouping displayed in the map visualization 1400) contains a subset of patients with similar genetic profiles.

As discussed herein, one or more patients (i.e., patient members of each node or grouping) may occur in multiple nodes. A patient may share a similar genetic profile with multiple nodes or multiple groupings. In one example, of 50,000 different gene expressions of the biological data, multiple patients may share a different genetic profiles (e.g., based on different gene expression combinations) with different groupings. When a patient shares a similar genetic profile with different groupings or nodes, the patient may be included within the groupings or nodes.

The cancer map visualization 1400 comprises groupings and interconnections that are associated with different clinical outcomes. All or some of the clinical outcomes may be associated with the biological data that generated the cancer map visualization 1400. The cancer map visualization 1400 includes groupings associated with survivors 1402 and groupings associated with non-survivors 1404. The cancer map visualization 1400 also includes different groupings associated with estrogen receptor positive non-survivors 1406, estrogen receptor negative non-survivors 1408, estrogen receptor positive survivors 1410, and estrogen receptor negative survivors 1412.

In various embodiments, when one or more patients are members of two or more different nodes, the nodes are interconnected by an edge (e.g., a line or interconnection). If there is not an edge between the two nodes, then there are no common member patients between the two nodes. For example, grouping 1414 shares at least one common member patient with grouping 1418. The intersection of the two groupings is represented by edge 1416. As discussed herein, the number of shared member patients of the two groupings may be represented in any number of ways including color of the interconnection, color of the groupings, size of the interconnection, size of the groupings, animations of the interconnection, animations of the groupings, brightness, or the like. In some embodiments, the number and/or identifiers of shared member patients of the two groupings may be available if the user interacts with the groupings 1414 and/or 1418 (e.g., draws a box around the two groupings and the interconnection utilizing an input device such as a mouse).

In various embodiments, a physician, on obtaining some data on a breast tumor, direct the data to an analysis server (e.g., analysis server 208 over a network such as the Internet) which may localize the patient relative to one or more groupings on the cancer map visualization 1400. The context of the cancer map visualization 1400 may enable the physician to assess various possible outcomes (e.g., proximity of representation of new patient to the different associations of clinical outcomes).

Figure 15:
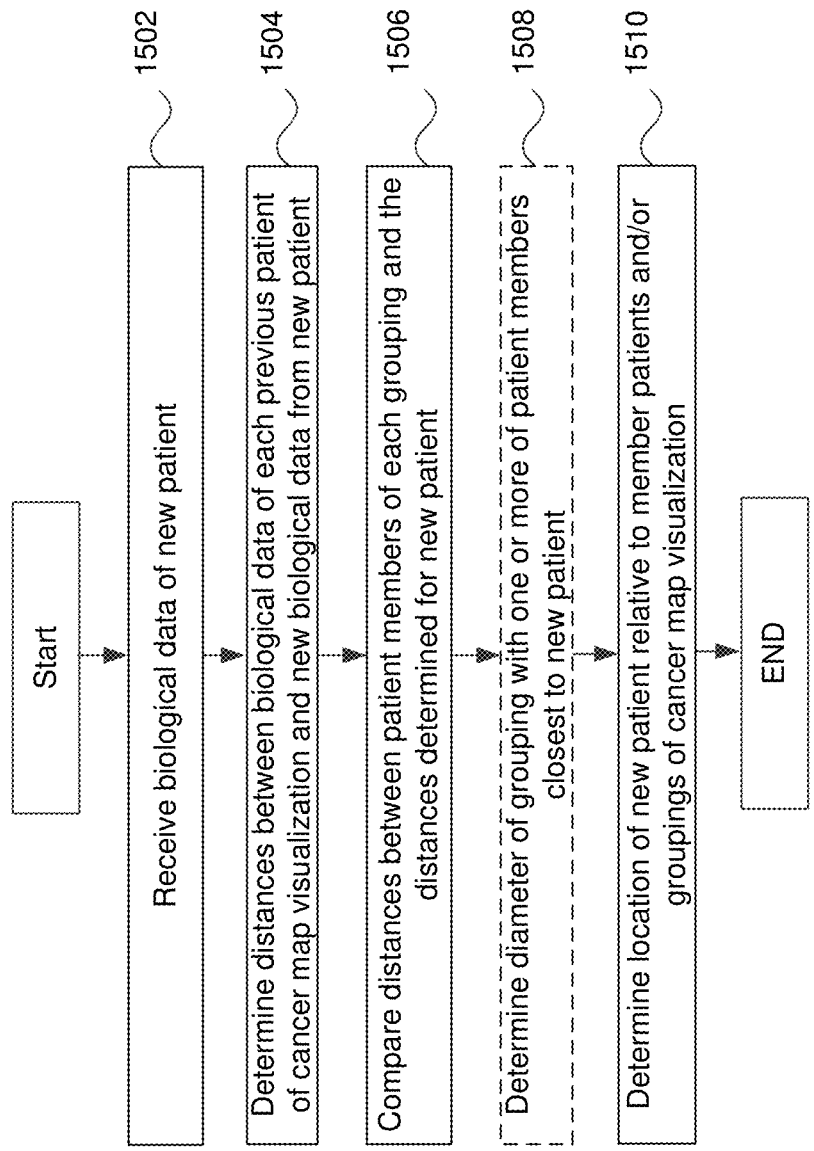
FIG. 15 is a flowchart of for positioning new patient data relative to the cancer map visualization in some embodiments.

FIG. 15 is a flowchart of for positioning new patient data relative to a cancer map visualization in some embodiments. In step 1502, new biological data of a new patient is received. In various embodiments, an input module 314 of an analysis server (e.g., analysis server 208 of FIGS. 1 and 2) may receive biological data of a new patient from a physician or medical facility that performed analysis of one or more samples to generate the biological data. The biological data may be any data that represents a biological data of the new patient including, for example, gene expressions, sequencing information, or the like.

In some embodiments, the analysis server 208 may comprise a new patient distance module and a location engine. In step 1504, the new patient distance module determines distances between the biological data of each patient of the cancer map visualization 1600 and the new biological data from the new patient. For example, the previous biological data that was utilized in the generation of the cancer map visualization 1600 may be stored in mapped data structures. Distances may be determined between the new biological data of the new patient and each of the previous patient's biological data in the mapped data structure.

It will be appreciated that distances may be determined in any number of ways using any number of different metrics or functions. Distances may be determined between the biological data of the previous patients and the new patients. For example, a distance may be determined between a first gene expression measurement of the new patient and each (or a subset) of the first gene expression measurements of the previous patients (e.g., the distance between G1 of the new patient and G1 of each previous patient may be calculated). Distances may be determined between all (or a subset of) other gene expression measurements of the new patient to the gene expression measurements of the previous patients.

In various embodiments, a location of the new patient on the cancer map visualization 1600 may be determined relative to the other member patients utilizing the determined distances.

In step 1506, the new patient distance module may compare distances between the patient members of each grouping to the distances determined for the new patient. The new patient may be located in the grouping of patient members that are closest in distance to the new patient. In some embodiments, the new patient location may be determined to be within a grouping that contains the one or more patient members that are closest to the new patient (even if other members of the grouping have longer distances with the new patient). In some embodiments, this step is optional.

In various embodiments, a representative patient member may be determined for each grouping. For example, some or all of the patient members of a grouping may be averaged or otherwise combined to generate a representative patient member of the grouping (e.g., the distances and/or biological data of the patient members may be averaged or aggregated). Distances may be determined between the new patient biological data and the averaged or combined biological data of one or more representative patient members of one or more groupings. The location engine may determine the location of the new patient based on the distances. In some embodiments, once the closest distance between the new patient and the representative patient member is found, distances may be determined between the new patient and the individual patient members of the grouping associated with the closest representative patient member.

In optional step 1508, a diameter of the grouping with the one or more of the patient members that are closest to the new patient (based on the determined distances) may be determined. In one example, the diameters of the groupings of patient members closest to the new patient are calculated. The diameter of the grouping may be a distance between two patient members who are the farthest from each other when compared to the distances between all patient members of the grouping. If the distance between the new patient and the closest patient member of the grouping is less than the diameter of the grouping, the new patient may be located within the grouping. If the distance between the new patient and the closest patient member of the grouping is greater than the diameter of the grouping, the new patient may be outside the grouping (e.g., a new grouping may be displayed on the cancer map visualization with the new patient as the single patient member of the grouping). If the distance between the new patient and the closest patient member of the grouping is equal to the diameter of the grouping, the new patient may be placed within or outside the grouping.

It will be appreciated that the determination of the diameter of the grouping is not required in determining whether the new patient location is within or outside of a grouping. In various embodiments, a distribution of distances between member patients and between member patients and the new patient is determined. The decision to locate the new patient within or outside of the grouping may be based on the distribution. For example, if there is a gap in the distribution of distances, the new patient may be separated from the grouping (e.g., as a new grouping). In some embodiments, if the gap is greater than a preexisting threshold (e.g., established by the physician, other user, or previously programmed), the new patient may be placed in a new grouping that is placed relative to the grouping of the closest member patients. The process of calculating the distribution of distances of candidate member patients to determine whether there may be two or more groupings may be utilized in generation of the cancer map visualization (e.g., in the process as described with regard to FIG. 12). It will be appreciated that there may be any number of ways to determine whether a new patient should be included within a grouping of other patient members.

In step 1510, the location engine determines the location of the new patient relative to the member patients and/or groupings of the cancer map visualization. The new location may be relative to the determined distances between the new patient and the previous patients. The location of the new patient may be part of a previously existing grouping or may form a new grouping.

In some embodiments, the location of the new patient with regard to the cancer map visualization may be performed locally to the physician. For example, the cancer map visualization 1400 may be provided to the physician (e.g., via digital device). The physician may load the new patient's biological data locally and the distances may be determined locally or via a cloud-based server. The location(s) associated with the new patient may be overlaid on the previously existing cancer map visualization either locally or remotely.

Those skilled in the art will appreciate that, in some embodiments, the previous state of the cancer map visualization (e.g., cancer map visualization 1400) may be retained or otherwise stored and a new cancer map visualization generated utilizing the new patient biological data (e.g., in a method similar to that discussed with regard to FIG. 12). The newly generated map may be compared to the previous state and the differences may be highlighted thereby, in some embodiments, highlighting the location(s) associated with the new patient. In this way, distances may be not be calculated as described with regard to FIG. 15, but rather, the process may be similar to that as previously discussed.

Figure 16:
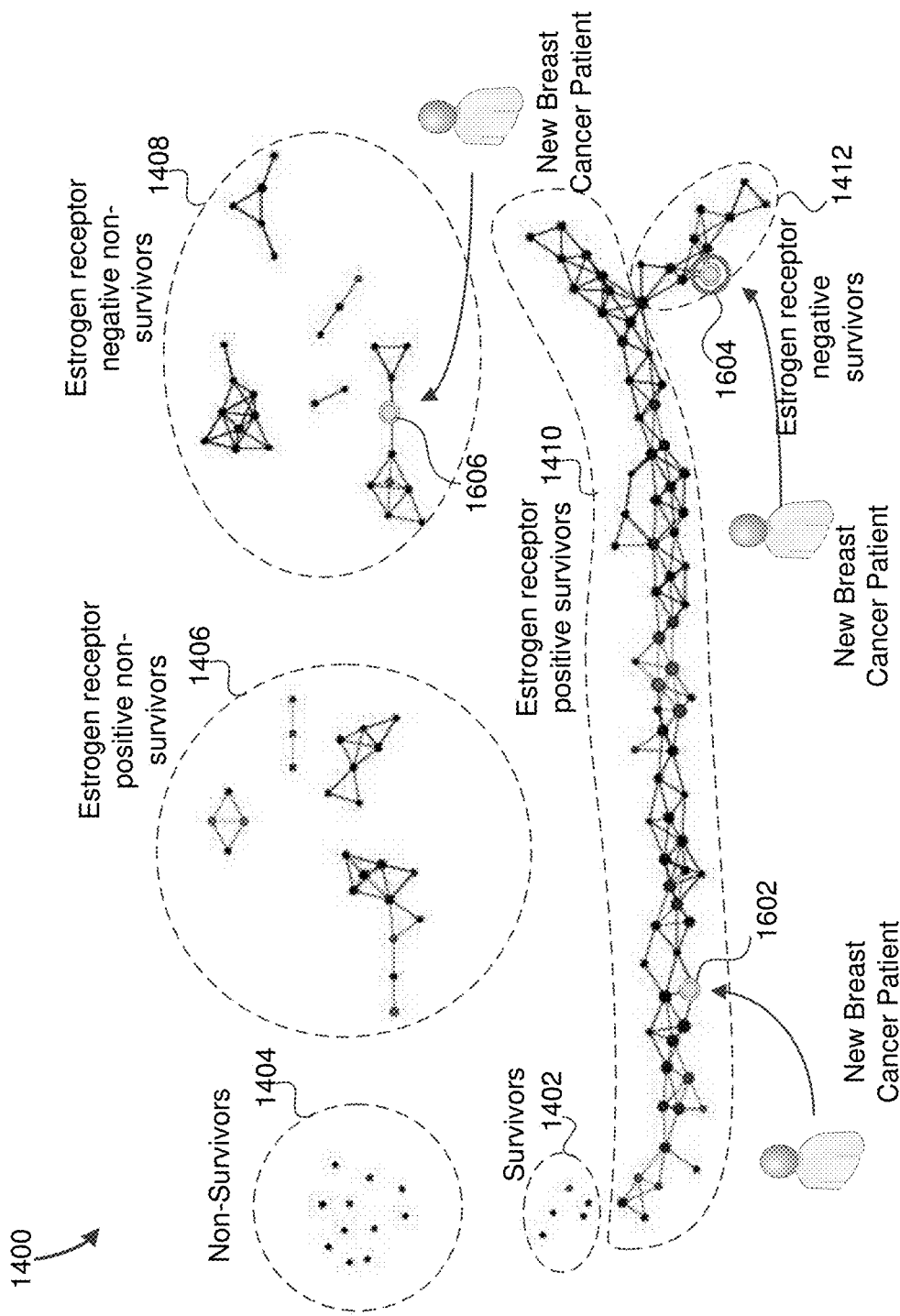
FIG. 16 is an example visualization displaying the cancer map including positions for three new cancer patients in some embodiments.

FIG. 16 is an example visualization displaying the cancer map including positions for three new cancer patients in some embodiments. The cancer map visualization 1400 comprises groupings and interconnections that are associated with different clinical outcomes as discussed with regard to FIG. 14. All or some of the clinical outcomes may be associated with the biological data that generated the cancer map visualization 1400. The cancer map visualization 1400 includes different groupings associated with survivors 1402, groupings associated with non-survivors 1404, estrogen receptor positive non-survivors 1406, estrogen receptor negative non-survivors 1408, estrogen receptor positive survivors 1410, and estrogen receptor negative survivors 1412.

The cancer map visualization 1400 includes three locations for three new breast cancer patients. The breast cancer patient location 1602 is associated with the clinical outcome of estrogen receptor positive survivors. The breast cancer patient location 1604 is associated with the clinical outcome of estrogen receptor negative survivors. Unfortunately, breast cancer patient location 1606 is associated with estrogen receptor negative non-survivors. Based on the locations, a physician may consider different diagnoses, prognoses, treatments, and therapies to maintain or attempt to move the breast cancer patient to a different location utilizing the cancer map visualization 1400.

In some embodiments, the physician may assess the underlying biological data associated with any number of member patients of any number of groupings to better understand the genetic similarities and/or dissimilarities. The physician may utilize the information to make better informed decisions.

The patient location 1604 is highlighted on the cancer map visualization 1400 as active (e.g., selected by the physician). It will be appreciated that the different locations may be of any color, size, brightness, and/or animated to highlight the desired location(s) for the physician. Further, although only one location is identified for three different breast cancer patients, any of the breast cancer patients may have multiple locations indicating different genetic similarities.

It will be appreciated that the cancer map visualization 1400 may be updated with new information at any time. As such, as new patients are added to the cancer map visualization 1400, the new data updates the visualization such that as future patients are placed in the map, the map may already include the updated information. As new information and/or new patient data is added to the cancer map visualization 1400, the cancer map visualization 1400 may improve as a tool to better inform physicians or other medical professionals.

In various embodiments, the cancer map visualization 1400 may track changes in patients over time. For example, updates to a new patient may be visually tracked as changes in are measured in the new patient's biological data. In some embodiments, previous patient data is similarly tracked which may be used to determine similarities of changes based on condition, treatment, and/or therapies, for example. In various embodiments, velocity of change and/or acceleration of change of any number of patients may be tracked over time using or as depicted on the cancer map visualization 1400. Such depictions may assist the treating physician or other personnel related to the treating physician to better understand changes in the patient and provide improved, current, and/or updated diagnoses, prognoses, treatments, and/or therapies.

Figure 17:
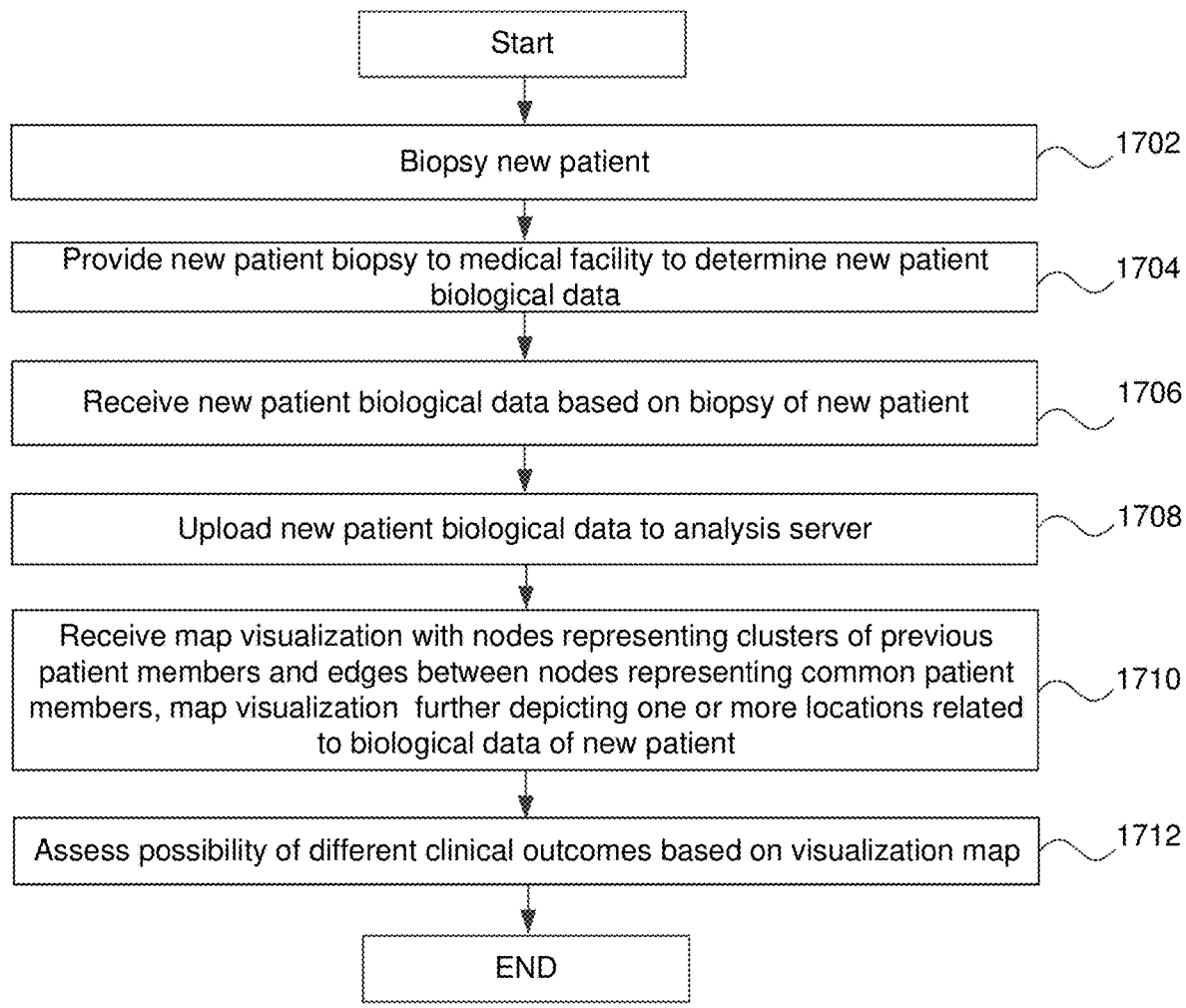
FIG. 17 is a flowchart of utilization the visualization and positioning of new patient data in some embodiments.

FIG. 17 is a flowchart of utilization the visualization and positioning of new patient data in some embodiments. In various embodiments, a physician may collect amounts of genomic information from tumors removed from a new patient, input the data (e.g., upload the data to an analysis server), and receive a map visualization with a location of the new patient. The new patient's location within the map may offer the physician new information about the similarities to other patients. In some embodiments, the map visualization may be annotated so that the physician may check the outcomes of previous patients in a given region of the map visualization are distributed and then use the information to assist in decision-making for diagnosis, treatment, prognosis, and/or therapy.

In step 1702, a medical professional or other personnel may remove a sample from a patient. The sample may be of a tumor, blood, or any other biological material. In one example, a medical professional performs a tumor excision. Any number of samples may be taken from a patient.

In step 1704, the sample(s) may be provided to a medical facility to determine new patient biological data. In one example, the medical facility measures genomic data such as gene expression of a number of genes or protein levels.

In step 1706, the medical professional or other entity associated with the medical professional may receive the new patient biological data based on the sample(s) from the new patient. In one example, a physician may receive the new patient biological data. The physician may provide all or some of the new patient biological data to an analysis server over the Internet (e.g., the analysis server may be a cloud-based server). In some embodiments, the analysis server is the analysis server 208 of FIG. 1. In some embodiments, the medical facility that determines the new patient biological data provides the biological data in an electronic format which may be uploaded to the analysis server. In some embodiments, the medical facility that determines the new patient biological data (e.g., the medical facility that measures the genomic data) provide the biological data to the analysis server at the request of the physician or others associated with the physician. It will be appreciated that the biological data may be provided to the analysis server in any number of ways.

The analysis server may be any digital device and may not be limited to a digital device on a network. In some embodiments, the physician may have access to the digital device. For example, the analysis server may be a table, personal computer, local server, or any other digital device.

Once the analysis server receives the biological data of the new patient, the new patient may be localized in the map visualization and the information may be sent back to the physician in step 1708. The visualization may be a map with nodes representing clusters of previous patient members and edges between nodes representing common patient members. The visualization may further depict one or more locations related to the biological data of the new patient.

The map visualization may be provided to the physician or other associated with the physician in real-time. For example, once the biological data associated with the new patient is provided to the analysis server, the analysis server may provide the map visualization back to the physician or other associated with the physician within a reasonably short time (e.g., within seconds or minutes). In some embodiments, the physician may receive the map visualization over any time.

The map visualization may be provided to the physician in any number of ways. For example, the physician may receive the map visualization over any digital device such as, but not limited to, an office computer, Ipad, tablet device, media device, smartphone, e-reader, or laptop.

In step 1710, the physician may assess possible different clinical outcomes based on the map visualization. In one example, the map-aided physician may make decisions on therapy and treatments depending on where the patient lands on the visualization (e.g., survivor or non-survivor). The map visualization may include annotations or labels that identify one or more sets of groupings and interconnections as being associated with one or more clinical outcomes. The physician may assess possible clinical outcomes based on the position(s) on the map associated with the new patient.

As described above, interesting continuous functions on a metric space (e.g., a similarity space) allow the application of systems and methods described herein. In various embodiments, functions may be performed on data within the metric space to project data into the reference space. Having the function(s) to project the data from the metric space to the similarity space (i.e., a lens function) dependent on a small number of coordinates (e.g., counting a number of uses of a small collection of words) is a fairly simple way to achieve continuity in most metrics, and the resulting lenses may be suitable for interpolation. However, such lenses may be of limited use on high-dimensional data, and if the interesting features of the space were captured in those few dimensions, there may be no point keeping the rest of the coordinates.

In practice, lenses which incorporate intrinsic properties of the metric (e.g., the function on the data to generate the metric space), such as density or centrality, are more likely to capture features of the space, absent special knowledge of the particular data set, than functions which depend on a few coordinates. One example method of dimensionality reduction (which is a way to think of a small collection of lenses applied jointly) are variants of "Stochastic Neighbor Embedding" (aka SNE). The underlying intuition in stochastic neighbor embedding is to map the high dimensional space to points in a low-dimensional Euclidean space, typically two or three dimensions, define a potential function on the points which penalizes them for being either closer or farther apart in the embedding than they are in the high-dimensional space, and move points around to minimize the potential. This may be effectively like a graph-layout problem, where a (potentially) high-dimensional space, an arbitrary combinatorial graph, is to be faithfully represented by a two-dimensional picture.

Some example methods amount to computing a global potential and then optimizing the placement by the same optimization techniques used in applications of artificial neural network. These methods produce very nice pictures and the lenses can be remarkably effective with TDA, but they may be computationally expensive. Some embodiments described herein allow for the use of less computationally expensive layout mechanisms and methods.

Figure 18:
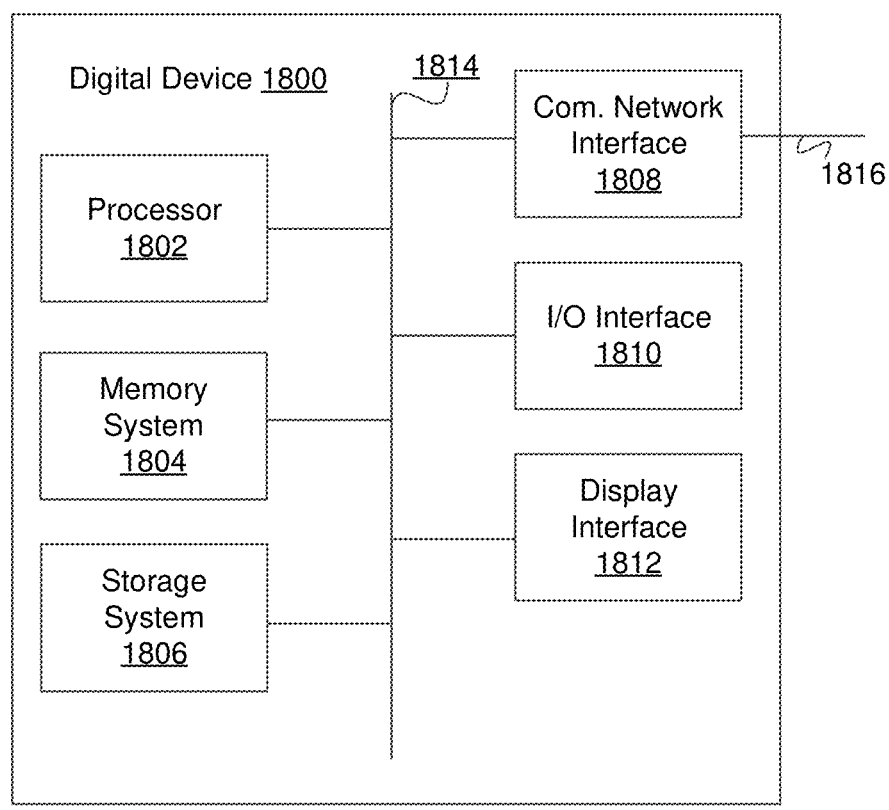
FIG. 18 is an example digital device in some embodiments.

FIG. 18 is a block diagram of an example digital device 1800. The digital device 1800 comprises a processor 1802, a memory system 1804, a storage system 1806, a communication network interface 1808, an I/O interface 1810, and a display interface 1812 communicatively coupled to a bus 1814. The processor 1802 may be configured to execute executable instructions (e.g., programs). In some embodiments, the processor 1802 comprises circuitry or any processor capable of processing the executable instructions.

The memory system 1804 is any memory configured to store data. Some examples of the memory system 1804 are storage devices, such as RAM or ROM. The memory system 1804 can comprise the ram cache. In various embodiments, data is stored within the memory system 1804. The data within the memory system 1804 may be cleared or ultimately transferred to the storage system 1806.

The storage system 1806 is any storage configured to retrieve and store data. Some examples of the storage system 1806 are flash drives, hard drives, optical drives, and/or magnetic tape. In some embodiments, the digital device 1800 includes a memory system 1804 in the form of RAM and a storage system 1806 in the form of flash data. Both the memory system 1804 and the storage system 1806 comprise computer readable media which may store instructions or programs that are executable by a computer processor including the processor 1802.

The communication network interface (com. network interface) 1808 can be coupled to a communication network (e.g., communication network 204) via the link 1816. The communication network interface 1808 may support communication over an Ethernet connection, a serial connection, a parallel connection, or an ATA connection, for example. The communication network interface 1808 may also support wireless communication (e.g., 1802.11 a/b/g/n, WiMax). It will be apparent to those skilled in the art that the communication network interface 1808 can support many wired and wireless standards.

The optional input/output (I/O) interface 1810 is any device that receives input from the user and output data. The optional display interface 1812 is any device that may be configured to output graphics and data to a display. In one example, the display interface 1812 is a graphics adapter.

It will be appreciated by those skilled in the art that the hardware elements of the digital device 1800 are not limited to those depicted in FIG. 18. A digital device 1800 may comprise more or less hardware elements than those depicted. Further, hardware elements may share functionality and still be within various embodiments described herein. In one example, encoding and/or decoding may be performed by the processor 1802 and/or a co-processor located on a GPU.

In various embodiments, data points of a data set or nodes in a graph are automatically grouped (i.e., "autogrouped"). The groupings may be approximations of a possible maxima (e.g., a best maxima) of a given scoring function that scores possible partitions of the original object (i.e., a collection of data points or a collection of nodes of a graph).

Autogrouping may be utilized to automatically find a collection of subsets of some set Y that share one or more given properties. In one example, autogrouping may be utilized to find a collection of subsets that is a partition of Y where Y is a subset of a finite metric space X or nodes in a graph. However, it will be appreciated, in some embodiments, that the methodology described herein has no such requirement.

In various embodiments, a selection of possible partitions of a data set (e.g., original data set or nodes in a visualization) may be identified and scored. A partition is a collection of disjoint subsets of a given set. The union of the subsets of each partition equal the entire original set. A hierarchical clustering method may be utilized on the original object Y to create a family of partitions of Y.

A first scoring function may score the subsets (i.e., to generate a Q_Subset score), a second scoring function may score the partitions (i.e., to generate a Q_Partition score), and a third scoring function may score the roots of trees coming from the hierarchical clustering method (i.e., to generate a Q_Max score). The highest scoring partition based on any one or a combination of these scoring functions may be found for the family. The first and/or second scoring functions may be any function or combination of functions that may be able to be scored. Example scoring functions are further discussed herein.

In some embodiments, autogrouping is the process in which a highest scoring partition is identified. The highest scoring partition may be the maximum of the given scoring function(s) of any number of subsets from any number of partitions.

In some embodiments, a limited number of partitions of all possible partitions may be generated. In fact, in some cases, the result may be better if the scorer is imperfect, as at least some hierarchical clustering algorithms generally avoid partitions with large numbers of miscellaneous singletons or other ugly sets which might actually be the global extreme for such a scoring function. It will be appreciated that the hierarchical clustering process may serve to condition data to only present 'good alternatives,' and so can improve the effectiveness of some scorers.

Since the number of partitions for a data set is high (e.g., $(N/log(N))^N$), it may be impractical to generate every possible partition. Unfortunately, most local improvement methods can easily get stuck. Some techniques to generate a subset of partitions involve attempting to maximize a modularity score over graph partitions by making an initial partition and then making local changes (e.g., moving nodes from one partition to another). Modularity is the fraction of edges that fall within given groups minus the expected such fraction if edges were distributed at random. Unfortunately, the modularity measure Q score may exhibit extreme degeneracies because it admits an exponential number of distinct high-scoring solutions and typically lacks a clear global maximum. Another approach to maximizing functions on partitions by local methods is to use probabilistic techniques such as simulated annealing. At least some embodiments described herein offer a deterministic alternative that is applicable to a wide range of scoring functions.

Subsets in one or more different partitions of those generated may be selected based, at least in part, on Q scores, further described herein. A new partition including the selected subsets may be generated or, if all of the selected subsets are already part of a generated partition, then the preexisting partition may be selected.

FIG. 19A, FIG. 19B, FIG. 19C and FIG. 19D depict examples of determining a partition based on scoring for autogrouping in some embodiments. In an example, there is a fixed space, S, of finite size. The nature of the space may be relevant only in so far as there is a way of clustering the space and scoring subsets. Referring to a graph G on S indicates a graph whose nodes are a collection of subsets where a node is connected to another node if and only if the two nodes have points in common. A partition includes one or more subsets. Each of the one or more subsets include all of the element(s) of S. For example, partition 1902 is a partition that includes subsets of all elements of S. Subsets 1904a-e include all elements of S. A union of all of the subsets 1904a-e is the partition 1902.

Figure 19A:
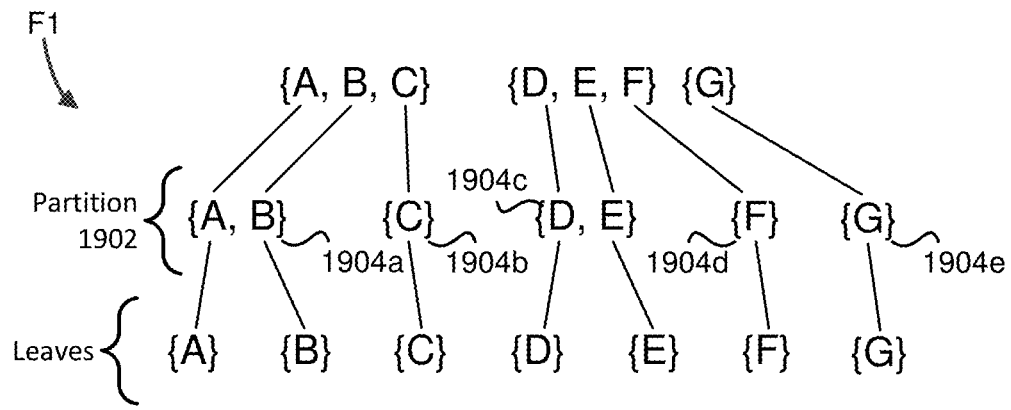
FIG. 19A, FIG. 19B, FIG. 19C and FIG. 19D depict examples of determining a partition based on scoring for autogrouping in some embodiments.
Figure 19B:
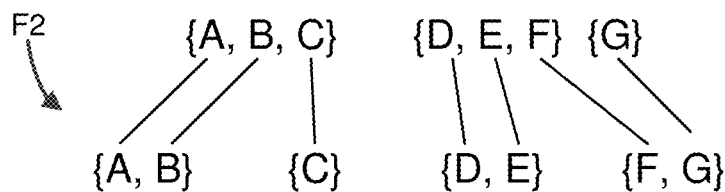
Figure 19C:
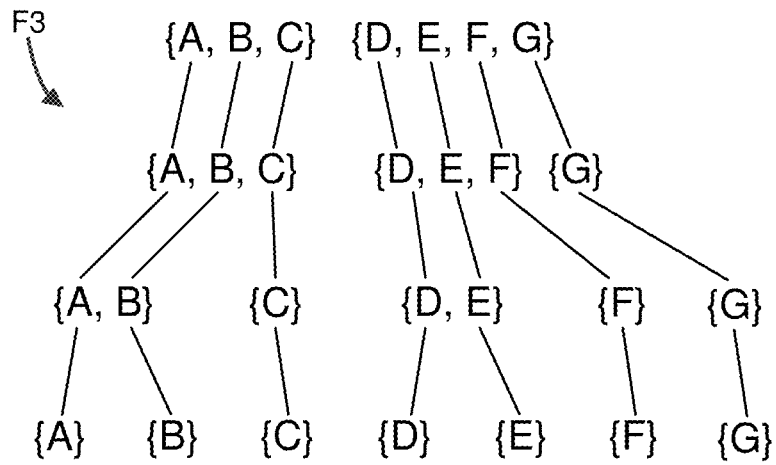

A forest F on S is a graph on S. A forest F is 'atomic' if every leaf in F is a singleton (e.g., a set with one member). FIG. 19A (i.e., F1) is an atomic forest because every leaf in F1 as depicted in FIG. 19A is a singleton. It will be appreciated that FIG. 19B (i.e., F2) is not an atomic forest since every leaf in F2 as depicted in FIG. 19B is not a singleton. For example, F2 includes leaves {A,B}, {D,E}, and {F,G}.

There is a partition R of S (in F1, {a,b,c}, {d,e,f}, {g}), called the roots, such that every set in F is reachable by a unique path from a root. N in F is either a leaf (e.g., a singleton in an atomic forest) or it is connected to nodes which form a partition (e.g., {a,b,c}->{a,b} and {c} in F1) of N. For a non-leaf node N we denote by C(N) the children of N. Notice the children of a leaf, namely C(leaf) is empty. We say that F' extends F if F and F' have the same leaves and every node in F is a node in F'. If the two forests are not equal, then F' contains a node which is the union of one or more roots in F. Example F3 (FIG. 19C) extends F1 (FIG. 19A).

Figure 19D:
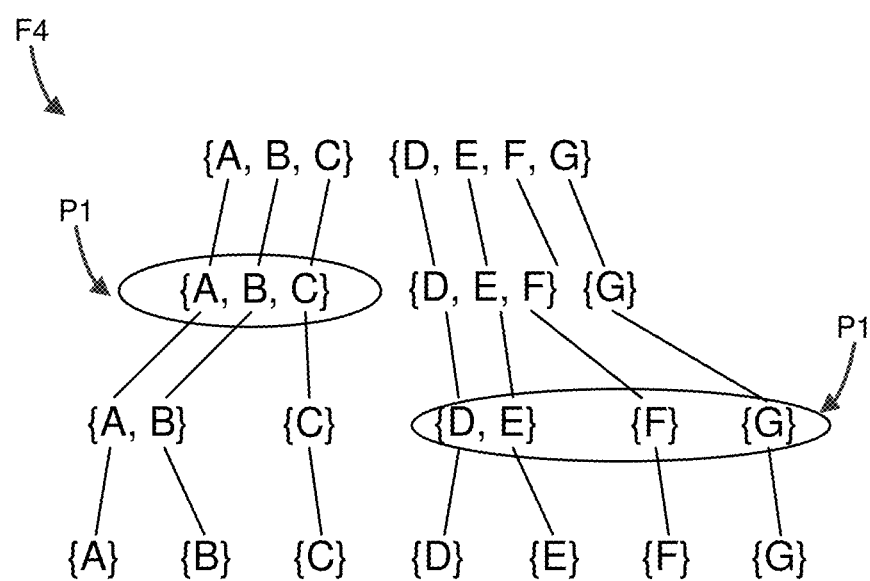

Partition P on S is subordinate to F1 if and only if every element of P is in F1. The circled partition P1 of F4 depicted in FIG. 19D, is an example of a subordinate partition {e.g., {a,b,c},{d,e},{f}, and {g}} to F1.

Singletons(S) are denoted as the partition formed by taking {{x}|x in S}. That is, in the example in FIG. 19D, Singletons({a, b, c, d, e, f, g})={{a},{b},{c},{d},{e}, {f}, {g}}. This is the same as the set of leaves of an atomic forest. Let U(P), where P is any collection of subsets of S, denote the union of all the elements of P. U(Singletons(S))==S.

Partition V on S is coarser than another partition P on S if and only if every element x' in P' is the union of elements x in P. In various embodiments, every partition on S is coarser than Singletons(S), and {S} is coarser than every partition on S. For instance, {{a,b,c},{d,e,f},{g}} is a coarser partition than {{a,b},{c},{d,e},{f},{g}}.

Figure 20:
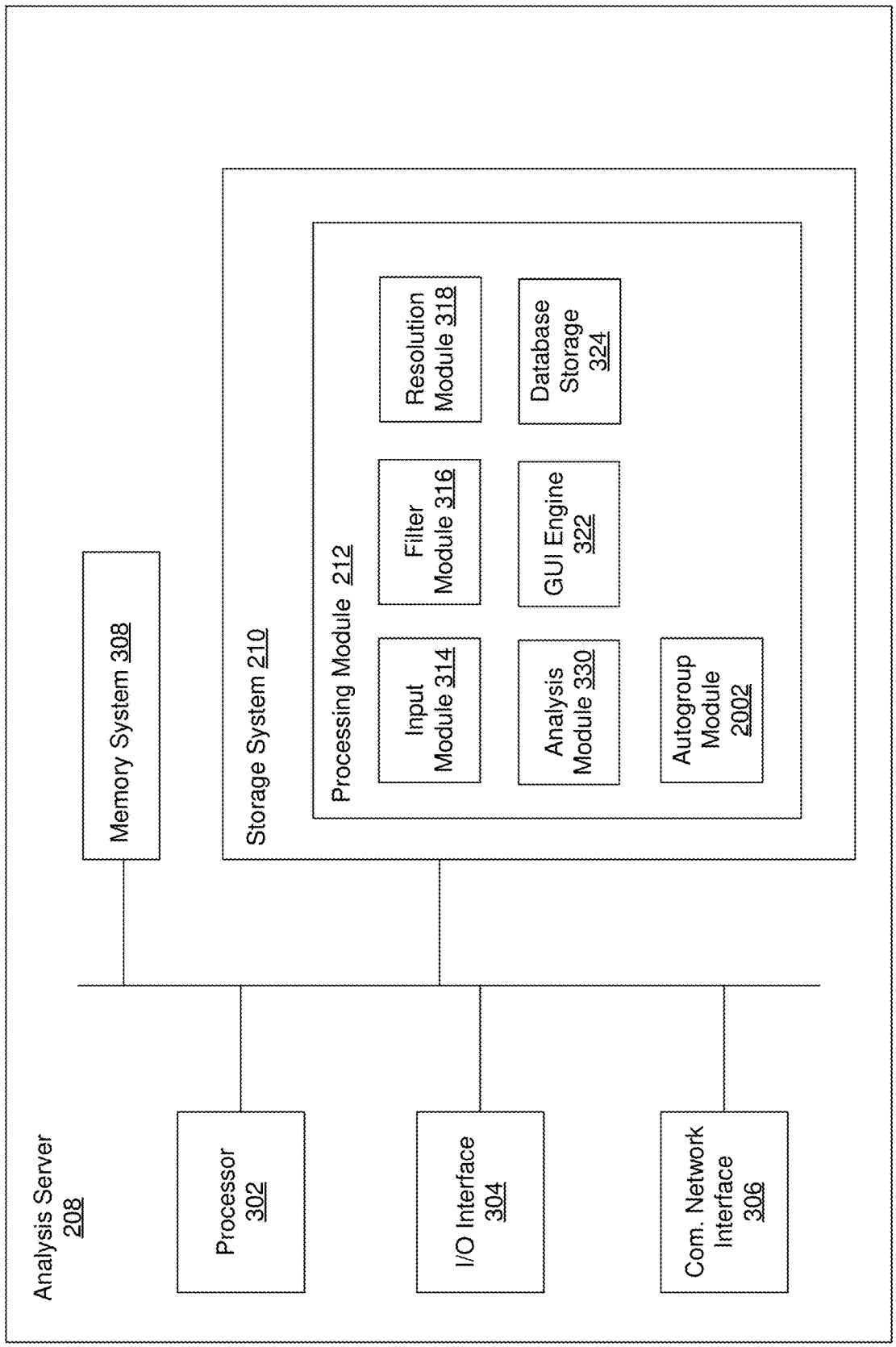
FIG. 20 is a block diagram of an example analysis server.

FIG. 20 is a block diagram of an example analysis server 208 including an autogroup module 2002. The example analysis server 208 depicted in FIG. 20 may be similar to the example analysis server 208 depicted in FIG. 2. In example embodiments, the analysis server 208 comprises a processor 302, input/output (I/O) interface 304, a communication network interface 306, a memory system 308, and a storage system 310.

The storage system 310 comprises a plurality of modules utilized by embodiments of the present invention. A module may be hardware (e.g., an ASIC), software (e.g., including instructions executable by a processor), or a combination of both. In one embodiment, the storage system 310 comprises a processing module 312 which comprises an input module 314, a filter module 316, a resolution module 318, an analysis module 320, a visualization engine 322, a database storage 324, and an autogroup module 2002. Alternative embodiments of the analysis server 208 and/or the storage system 310 may comprise more, less, or functionally equivalent components and modules.

The input module 314 may be configured to receive commands and preferences from the user device 202a. In various examples, the input module 314 receives selections from the user which will be used to perform the analysis. The output of the analysis may be an interactive visualization.

The input module 314 may provide the user a variety of interface windows allowing the user to select and access a database, choose fields associated with the database, choose a metric, choose one or more filters, and identify resolution parameters for the analysis. In one example, the input module 314 receives a database identifier and accesses a large multidimensional database. The input module 314 may scan the database and provide the user with an interface window allowing the user to identify an ID field. An ID field is an identifier for each data point. In one example, the identifier is unique. The same column name may be present in the table from which filters are selected. After the ID field is selected, the input module 314 may then provide the user with another interface window to allow the user to choose one or more data fields from a table of the database.

Although interactive windows may be described herein, it will be appreciated that any window, graphical user interface, and/or command line may be used to receive or prompt a user or user device 202a for information.

The filter module 316 may subsequently provide the user with an interface window to allow the user to select a metric to be used in analysis of the data within the chosen data fields. The filter module 316 may also allow the user to select and/or define one or more filters.

The resolution module 318 may allow the user to select a resolution, including filter parameters. In one example, the user enters a number of intervals and a percentage overlap for a filter.

The analysis module 320 may perform data analysis based on the database and the information provided by the user. In various embodiments, the analysis module 320 performs an algebraic topological analysis to identify structures and relationships within data and clusters of data. It will be appreciated that the analysis module 320 may use parallel algorithms or use generalizations of various statistical techniques (e.g., generalizing the bootstrap to zig-zag methods) to increase the size of data sets that can be processed. The analysis is further discussed in FIG. 8. It will be appreciated that the analysis module 320 is not limited to algebraic topological analysis but may perform any analysis.

The visualization engine 322 generates an interactive visualization including the output from the analysis module 320. The interactive visualization allows the user to see all or part of the analysis graphically. The interactive visualization also allows the user to interact with the visualization. For example, the user may select portions of a graph from within the visualization to see and/or interact with the underlying data and/or underlying analysis. The user may then change the parameters of the analysis (e.g., change the metric, filter(s), or resolution(s)) which allows the user to visually identify relationships in the data that may be otherwise undetectable using prior means. The interactive visualization is further described in FIGS. 9-11.

The database storage 324 is configured to store all or part of the database that is being accessed. In some embodiments, the database storage 324 may store saved portions of the database. Further, the database storage 324 may be used to store user preferences, parameters, and analysis output thereby allowing the user to perform many different functions on the database without losing previous work.

The autogroup module 2002 is configured to autogroup data points of a data set or nodes in a graph. As discussed herein, the groupings may be approximations of possible maxima of a given scoring function that scores possible partitions of the original data object (e.g., a collection of data points or a collection of nodes of a graph). The autogroup module 2002 may, in some embodiments, perform autogrouping of nodes of a graph (whether a visualization is generated or not). In various embodiments, the autogroup module 2002 may perform autogrouping for reference space open cover generation. The autogroup module 2002 may autogroup any number of data points, sets of data points, representations, and/or the like. The autogroup module 2002 is further discussed in FIG. 21.

It will be appreciated that that all or part of the processing module 212 may be at the user device 202a or the database storage server 206. In some embodiments, all or some of the functionality of the processing module 312 may be performed by the user device 202a.

Figure 21:
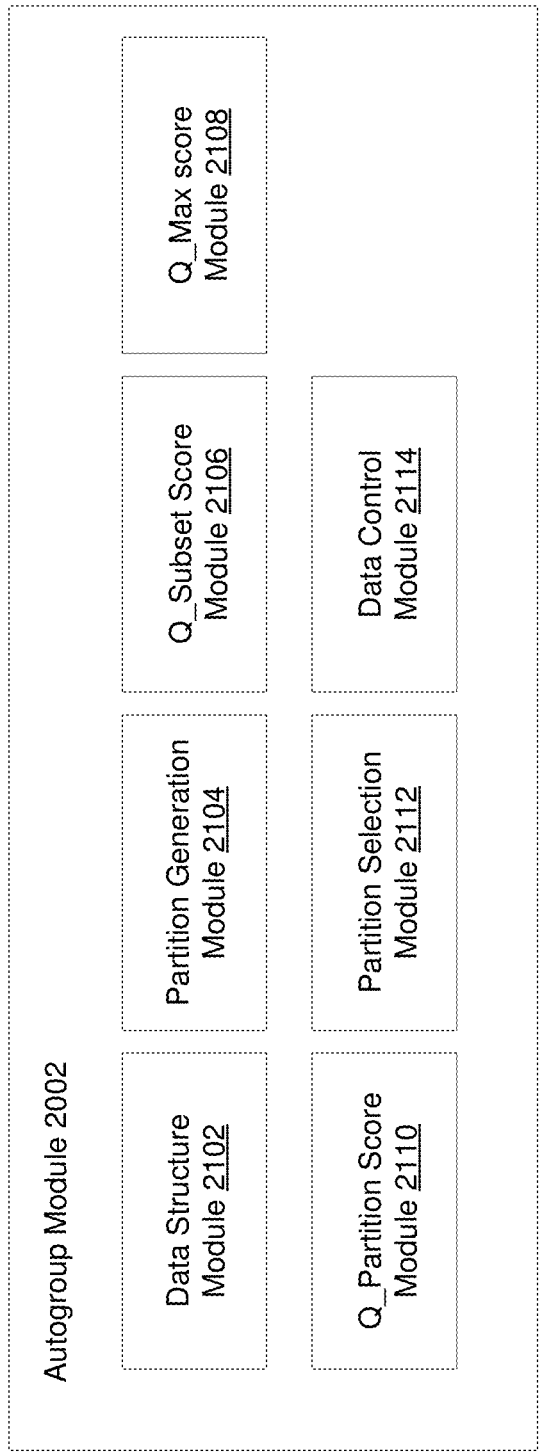
FIG. 21 depicts an example autogroup module in some embodiments.

FIG. 21 depicts an example autogroup module 2002 in some embodiments. An autogroup module 2002 may comprise a data structure module 2102, a partition generation module 2104, scoring function modules (e.g., a Q_subset score module 2106, a Q_max score module 2108, a Q_partition score module 2110), a partition selection module 2112, and a data control module 2114. Although the scoring function modules are discussed as including three modules, each performing a different scoring function, it will be appreciated that there may be any number of scoring function modules performing any number of scoring functions (e.g., one module performing a single scoring function capable of generating any number or type of scores). For example, the scoring functions may generate and/or maximize metric values of any number of metric functions.

In various embodiments, the data structure module 2102 receives data including a plurality of sets of data. The data may be received from any number of digital devices.

The partition generation module 2104 (e.g., a "clumper") forms a forest F utilizing the plurality of sets of data received by the data structure module 2102. For example, the partition generation module 2104 may generate a first partition of a forest F using the data received by the data structure module 2102. In some embodiments, the first partition may include leaves that are singletons of all elements from the data. In various embodiments, the first partition may include any number of sets of data. The first partition may include leaves for the forest, singletons, roots, sets of plurality of elements, and/or the like.

The partition generation module 2104 may generate the second partition of the forest F using the first partition. For example, the second partition may include at least one union of at least two sets of the first partition. Subsequent partitions may be generated in a similar fashion (e.g., based, at least in part, on including at least one union of at least two sets from the previous partition).

The partition generation module 2104 may generate an entire forest F before scoring partitions (or sets of partitions). For example, the partition generation module 2104 may generate the entire forest F before any or all of the scoring function modules score all or parts of partitions of the forest F.

In some embodiments, the partition generation module 2104 may generate the entire forest F while scoring is performed or in series with partition scoring (e.g., scoring of sets of partitions). For example, the partition generation module 2104 may generate the entire forest F while any or all of the scoring function modules score all or parts of partitions of the forest F. In another example, the partition generation module 2104 may generate one or more partitions of the forest F and then any number of the scoring function modules may score the generated partitions before the partition generation module 2104 generates one or more additional partitions of the forest F.

In various embodiments, the partition generation module 2104 may generate a partition of a forest F based on, at least in part, scores by any number of scoring function modules of previously generated partition(s) (or sets of partition(s)) of the forest F.

It will be appreciated that the partition generation module 2104 may not generate the entire forest F but may rather terminate generating partitions of the forest F before the forest F is completed. The partition generation module 2104 may determine whether to build a new partition of the forest F based on any number of the previously generated partition(s) of the forest F and/or scoring associated with all or parts of previously generated partition(s).

As discussed herein, the partition generation module 2104 may not generate all possible sets of data and/or all possible partitions of the forest F.

It will be appreciated that the partition generation module 2104 may utilize any number of hierarchical clustering techniques with techniques described herein. In one example, data and/or nodes are joined by epsilon (if 2 data subsets or nodes are within distance epsilon of each other then they are joined together). While this example standard technique has traditional limitations ("fixed epsilon") whereby a single epsilon may be unable to break up a space in a preferable manner, by scoring each subset of a partition, we can select subsets across a forest to identify and/or generate a selected partition (e.g., by autogrouping subsets of a plurality of partitions).

One example of a hierarchical clustering technique, KNN on a finite metric space X is to compute the K nearest neighbors for each point of a network graph (e.g., a visualized or non-visualized graph that includes nodes that may be coupled to one or more other nodes of the graph) with, for example, K=50. The partition generation module 2104 may start with INITIAL( ) being Singletons(X). Then at each step for 1<=k<=50, the partition generation module 2104 may connect x to y provided x and y are in the symmetric k nearest neighbors of one another. Note that if KNN(P,k) returns P for k<50, the partition generation module 2104 may bump k and try again instead of concluding that P is stable.

Another hierarchical clustering technique embodiment is defined on a weighted graph G (with positive weights) on a point set S. This hierarchical clustering technique is parameterized by a pre-determined real number delta where 1>delta>0. The partition generation module 2104 starts with delta=0 so INITIAL( ) being Singletons(S). For each partition P, we define wt(p,q), for p!=q in P, to be the sum of edge weights between the nodes in the graph which are a part of the subset p and those in the subset q in G, divided by |p|*|q|. The partition generation module 2104 is configured to take a partition P and make a new partition P' by joining all pairs of subsets (a,b) (where a, b are subsets in the partition P) when wt(a,b)>=delta*max(wt(p,q)) where the max is over all pairs of subsets p and q in the partition P.

There are any number of techniques for hierarchical clustering and any of them can be combined with a scoring function that satisfies example constraints on the scoring functions discussed herein.

The autogroup module 2002 includes the Q_Subset score module 2106, the Q_Max score module 2108, and the Q_Partition score module 2110 which may utilize three scoring functions, respectively. The Q_Subset score module 2106 calculates a Q_Subset score for subsets of one or more partitions. The Q_Max score module 2108 calculates a Q_Max score based on the Q_Subset score (e.g., calculates a maximum score for a partition based on the Q_Subset score) for the subsets. The Q_Partition score module 2110 calculates a Q_Partition score for two or more partitions of the forest utilizing at least the Q_Subset Score for the subsets.

In various embodiments, the Q_Subset score module 2106 calculates Q_Subset scores (e.g., one for each subset of a partition). A function Q is defined on subsets of the space S and scores the properties which are to be grouped together in the autogrouping process. For instance, in some embodiments, the Q_Subset score is a modularity score on a graph (so S are the nodes in the graph). The partition selection module 2112 may examine the data structure for a partition of the graph S with maximum modularity score(s).

Modularity is one measure of the structure of networks or graphs that is appreciated by those skilled in the art. The modularity score may be used to measure strength of division of a network of nodes (e.g., modules, groups, clusters, or communities). Modularity may be used in optimization methods for detecting community structure in networks. In one example, modularity is the fraction of edges of nodes in a graph that fall within a given group minus the expected such fraction if edges were distributed at random. It will be appreciated that there are many different methods for calculating modularity.

In one example, randomization of edges preserves a degree of each vertex. Assume a graph with n nodes and m links (edges) such that the graph can be partitioned into two communities using a membership variable s. If a node belongs to community 1, Sv=1, or if v belongs to community 2, Sv=−1. An adjacency matrix for an undirected network may be represented by A, where Avw=0 indicates there are no edges (no interaction) between nodes v and w. Avw=1 indicates there are Avw=1 indicates there is an edge between the two.

Modularity Q may be defined as the fraction of edges that fall within group 1 or 2, minus the expected number of edges within groups 1 and 2 for a random graph with the same node degree distribution as the network.

In this example, an expected number of edges is determined using configuration models. The configuration model is a randomized realization of a particular network. Given a network with n nodes, where each node v has a node degree kv, the configuration model cuts each edge into two halves, and then each half edge is rewired randomly with any other half edge in the network.

For this example, assume that the total number of half edges is $l_n$ $$l_n = \sum_v k_v = 2m$$

Two randomly nodes v and w with node degrees $k_v$ and $k_w$ respectively are selected and half edges rewired then the expectation of full edges between v and w is equal to (Full edges between v and w)/(total number of rewiring possibilities). The expected [Number of full edges between v and w]=$(k_v*k_w)/l_n$=$(k_v k_w)/2m$.

As a result, the actual number of edges between v and w minus expected number of edges between them is $A_{vw}$-$(k_v k_w)/2m$.

$$Q = \frac{1}{2m}\sum_{vw}\left[A_{vw} - \frac{k_v * k_w}{2m}\right]\frac{s_v s_w + 1}{2}$$

The equation above holds for partitioning into two communities only. Hierarchical partitioning (i.e. partitioning into two communities, then the two sub-communities further partitioned into two smaller sub communities only to maximize Q) is a possible approach to identify multiple communities in a network. The above equation can be generalized for partitioning a network into c communities.

$$Q = \sum_{vw}\left[\frac{A_{vw}}{2m} - \frac{k_v * k_w}{(2m)(2m)}\right]\delta(c_v, c_w) = \sum_{i=1}^{c}(e_{ii} - a_i^2)$$

$e_{ij}$ is the fraction of edges with one end vertices in community i and the other in community j:

$$e_{ij} = \sum_{vw}\frac{Avw}{2m}1_{v\in c_i}1_{v\in c_j}$$

$a_i$ is the fraction of ends of edges that are attached to vertices in community i:

$$a_i = \frac{k_i}{2m} = \sum_j e_{ij}$$

The second scoring function, the Q_Partition score, may be an extension of the first scoring function Q to be defined on partitions of the space S. If the scoring function Q is defined on subsets of S, it can be extended to a partition function Q_Partition in various ways. One of the simplest ways to extend function Q to partitions is by defining Q_Partition (P) as the sum over p in P of Q(p) (e.g., for a partition P, Q_Partition (P)=sum_{subsets p in P} Q(p)).

In some embodiments, Q_Partition must have the following property: Let P be an arbitrary partition of a subset of S, let p belong to P, and let q be a partition of p. P(q) is defined to be the partition of obtained by replacing p in P with the elements of q. Then, in this example, Q_Partition must have the following property for all P, p, q as described above:

$$QP(P(q))>=QP(P) \text{ if and only if } QP(q)>=Q(\{p\}) \tag{1}$$

In some embodiments, function Q does not need to come from a set function in this case. Functions Q_Partition which satisfy property (1) are, by definition, stable partition functions. A class of such functions is described as follows.

Let Q be any real-valued function defined on the set of non-empty subsets of S. Let A(p,q) be any function defined on pairs of non-empty subsets such that p is a subset of q. If:

$$A(p,p)==1 \text{ and } A(p,q)*A(q,r)=A(p,r), \text{ for all legal } p,q,r \tag{2}$$

then we may extend the set function Q( ) to all partitions P by:

$$QP(P)=\text{sum } A(p,U(P))Q(p) \tag{3}$$

p in P

Note that all real numbers k, $A(p,q)==(|p|/|q|)^k$ satisfies this property. Moreover, k==0 implies A(p,q)==1.

(1) holds for Q defined in (3). If QP and QP' are stable partition functions, then so is x*QP+y*QP' for x, y>=0. We also refer to stable partition functions on S as "partition scoring functions" for F.

For any scoring function of the form (3), a monotonically increasing function f may be chosen from the real numbers to itself and replace Q by Q'( )=f(Q( )). In particular, if f( ) is 'sufficiently invertible' (e.g., A( ) and Q( ) are >=0 and f( ) is invertible on the non-negative reals). QP(P) may be defined by:

$$QP'(P)=f\text{-inverse}(\text{sum } A(p,U(P))f(Q(p))) \tag{3'}$$

p in P

Since f(QP(P)) satisfies (1) and f( ) is monotonically increasing, the QP' in (3') also satisfies (1) and extends Q( ) on subsets of S. Concretely, if A==1 and Q( )=0 on sets, QP(P) may be defined to be the Euclidean norm of Q( ) on the individual elements of P, and still get a scoring function. Also can use the exponential function for f( ) without requiring Q to be non-negative.

In various embodiments, there may be extreme values under comparisons, using either <= or >=, for a function Q defined on partitions of subsets of S. Since Q may be replaced by −Q if the comparison is <=, it may be assumed without loss of generality that maximal values for Q (i.e., >=) are of interest. Specifically, a method for finding the F-subordinate partition on which Q is maximal, provided Q satisfies a simple property, is disclosed herein.

Given a scoring function Q_Partition on F, we can define a scoring function Q_max ( ) to be Q(p) if p is a leaf, and max(Q(p),Qmax(C(p))) if not. One consequence of this definition and requirement (1) on Q_Partition is that the maximal partition of a subset p (that is, the partition V of p for which Qmax(V) is maximal) is either p or the union of the maximal partitions of each element of C(p) (ties may be broken by taking the subset p instead the children).

In various embodiments, the autogrouping method uses a hierarchical clustering process on S to compute F (i.e., to construct the forest F) and if Q_Partition is a scoring function on the roots R of F, we can find the Q_Max maximal partition of S subordinate to F. Joining a scoring function Q( ) with hierarchical clustering may provide a principled method for choosing among the partitions for the "Q-maximal partition."

The partition generation module 2104 may begin with the original space S and may form a forest F described above. In some embodiments, the generation module 2104 takes a partition P and returns a new partition P' which is coarser than P. Note that Clumper({S})={S}. Any partition P such that generation module 2104 Clumper(P)=P is called clumper-terminal, and repeated applications must eventually reach a clumper-terminal partition. The sequence Singletons (S), Clumper(Singletons(S)), Clumper(Clumper(Singletons (S))), etc., may terminate in a finite number of steps, and the union of all these partitions forms an atomic forest F whose roots are the elements in a C-terminal partition R, which are the roots of F.

One example process utilizing the scoring functions and generating partitions is as follows in the following pseudo-code:

```
P = INITIAL(S) // some initial partion - often Singletons( ), but it
can be any partition
F = Tree(P) // node for every subset, remember connections, and
have max slot // to hold partition of the node's set which has
maximal score
for (x in S){ {x}.max = {x} }
BEGIN
  P' = clumper(P)
  if P==P'
  then
    quit
  else
    UPDATE_Qmax(P',P)
END
UPDATE_Qmax(P',P)
  for (p in P') {
    if (!(p in P)) {
      Subset pSubset = AddSubset(p,F);
      if (Q_Subset(p) >= QP(C(p)))
        pSubset.maxPartition = p
        pSubset.Qmax = Q(p)
      else
        pSubset.Qmax = QP(C(p))
        pSubset.maxPartition = MAX_UNION(C(p))
    }
  }
MAX_UNION({Ni})
  return the union of Ni.max
```

When this process terminates, the elements of the roots R of F may contain their maximal partitions, the union of which is the best partition in F of S.

The partition selection module 2112 may find a partition subordinate to the forest F that maximizes at least one scoring function. For example, the partition selection module 2112 may select a partition subordinate to the forest F that maximizes the scoring function QP.

In various embodiments, each subset of a partition (as discussed herein) may be associated with its own scores. For example, each subset of a partition may be associated with a different Q_Max score. The partition selection module 2112 may select subsets of unique elements from any number of different partitions of the forest F using the Q_Max score to generate and select a partition.

For example, looking to FIG. 19D, the partition selection module 2112 may select subset {A,B,C} from one partition and subsets {D,E}, {F}, AND {G} from another partition based on a scoring function. The selected subsets may then form (e.g., generate) a new selected partition P1 (e.g., a partition including subsets {A,B,C}, {D,E}, {F}, AND {G}). The selected partition P1 may be termed an output partition. In this example, the partition selection module 2112 may select the subset {A,B,C} from the first partition utilizing the Q_Max score. In a further example, each subset of all partitions that include any of elements A, B, or C, may be associated with a separate Q_Max score. The maximum Q_Max score of all the sets that include any of the elements of A, B, or C is the subset {A,B,C}. As a result, the partition selection module 2112 selects that subset {A,B,C} in this example.

Similarly, each subset of all partitions that include any of elements D, E, F, or G, may be associated with a separate Q_Max score. The maximum Q_Max scores of all the sets that include any of the elements of D, E, F, or G are the subsets {D,E}, {F}, and {G} (i.e., the Q_Max scores associated with subsets {D, E, F, G}, {D, E, F}, and {G} are not the maximum when compared to the Q_Max scores of subsets {D,E}, {F}, and {G}). As a result, the partition selection module 2112 selects subsets {D,E}, {F}, and {G} in this example.

One example of a scoring function mentioned herein includes a modularity score for weighted graphs on a node set S. In some embodiments, the modularity score of a subset of a graph proportion of edges within a subset, the e's, and the a's which are the proportion of edges which cross the boundaries of the subset. The final score may be: e−a^2. In various embodiments, the partition selection module 2112 selects and/or generates a partition by maximizing this score. The modularity partition scorer, QP, may be the sum of the modularity scores on the subsets within that partition.

Another example of a scoring function is a variant of entropy for a set S which has an associated classification: that is, a function cls: S→{1, 2, . . . , k} (i.e. you have a set and everything has some finite label.) For s subset of S, we define p_i(s)=|{x in s: cls(x)==i}|/|s|, provided |s|!=0. Then Q(s)=sum_{classes i} (p_i(s)*log(p_i(s))). The extension of the entropy scorer Q to a partition scorer, QP is given by the extension property (3) where A(p,q)=|p|/|q|. In other words, for a partition P, QP(P)=sum_{p in P} (Q(p)*|p|/|U(P)|). Normally one wants to minimize the entropy and the subset scorer here is the negative of the traditional entropy score by maximizing the scoring function.

The data control module 2114 is configured to provide the selected and/or generated partition from the partition selection module 2112. In various embodiments, the data control module 2114 generates a report indicating the selected and/or generated partition from the partition selection module 2112. The report may include, for example, data sets, partitions, subsets, elements, data set identifiers, partition identifiers, subset identifiers, element identifiers, and/or the like. In some embodiments, the report may include a graph (e.g., see FIG. 19) with an indication of selected nodes whose member(s) include data of the selected and/or generated partition from the partition selection module 2112.

Figure 22:
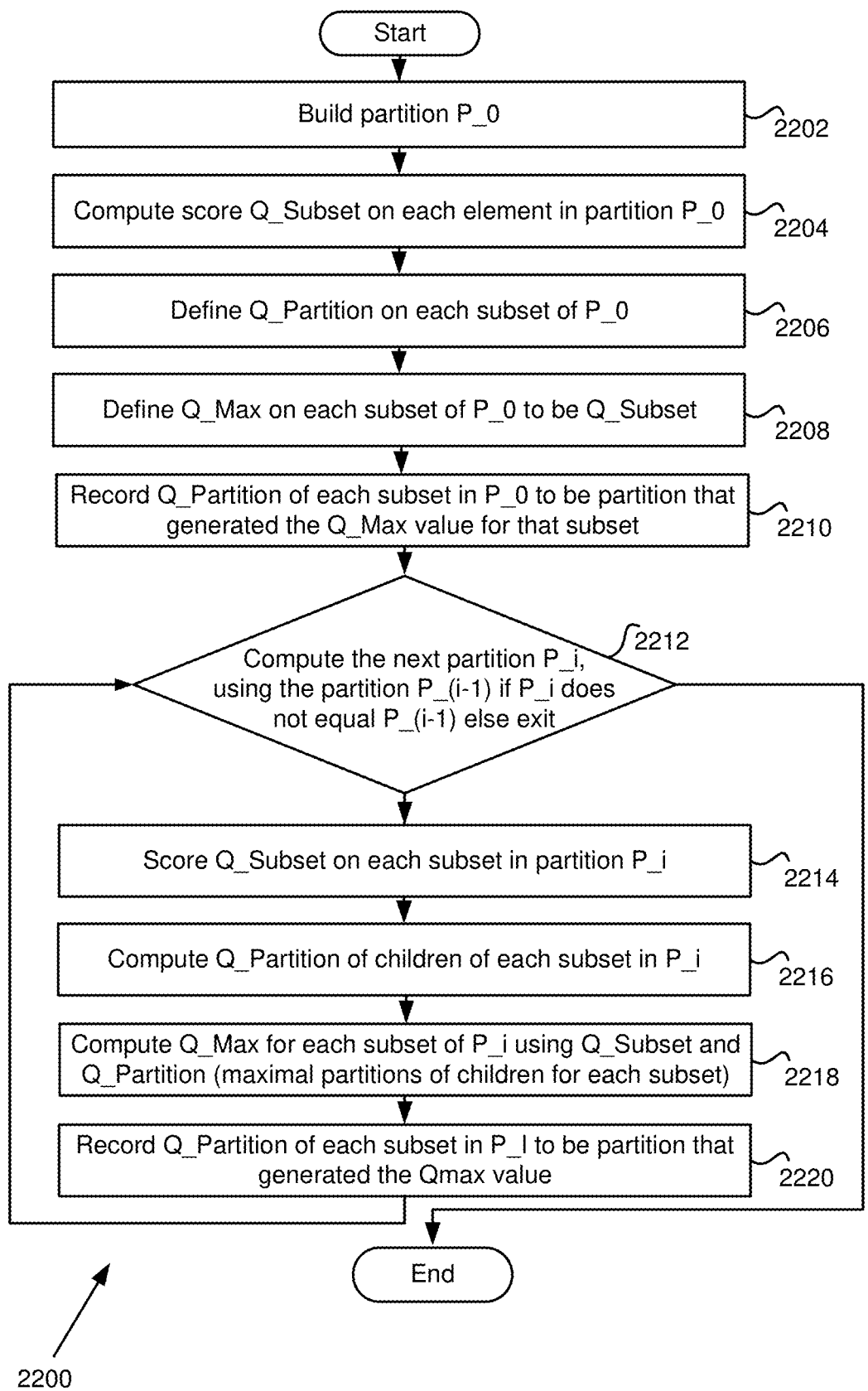
FIG. 22 is an example flowchart for autogrouping in some embodiments.

FIG. 22 is an example flowchart for autogrouping in some embodiments. In this example, the autogroup module 2002 receives a set S={A, B, C, D, E, F, G} and performs autogrouping to identify a selected partition of a forest based on S. Elements of set S may be, for example, nodes of a graph wherein the graph may be visualized (e.g., a visualization as discussed herein) or not visualized. The graph may be a topological data analysis graph of nodes and edges as described herein. In some embodiments, the graph may be any network graph that includes nodes, neighborhoods, groupings, communities, and/or data points.

Non-limiting examples describing at least some of the steps in FIG. 22 will be described using the graph depicted in FIG. 23. The embodiment of the Q_Partition in this example is simply the sum over the subsets of the partition P of the Q_Subset scores on each subset. For example, if P={{A, B, C}, {D}, {E, F}, {G}}, then Q_Partition (P)=Q_Subset({A, B, C})+Q_Subset({D})+Q_Subset({E, F})+Q_Subset({G}).

In step 2202, the data structure module 2102 receives the set S and the partition generation module 2104 generates an initial partition which are the singletons of the set S={A, B, C, D, E, F, G}, namely, P_0={{A}, {B}, {C}, {D}, {E}, {F}, {G}}. This is illustrated in FIG. 23 as the bottom row (2302) of the depicted forest.

In step 2204, the Q_subset score module 2106 computes the Q_Subset score on each subset of the partition P_0. In this example, the Q_subset score module 2106 scores each singleton subset with a value of 0.5. This score is shown in FIG. 23 for each subset of partition 2302 as Q_Sub=0.5. The scoring function in this example, may be a modularity scoring function discussed herein.

In step 2206, the Q_partition score module 2110 computes the maximal partition of each subset a of P_0 from the children of the subset a in the constructed forest. Since the subsets a in P_0 have no children in the forest, the maximal partition of the children of the subset a is itself. Namely, for each subset a in P_0, MaximalPartitionChildren(a)=a.

In this example, the Q_partition score module 2110 computes the maximal partition of each subset as itself. This is shown in FIG. 23 for each subset of partition 2302 as MaxP={A} for subset {A}, MaxP={C} for subset {C}, MaxP={D} for subset {D}, MaxP={E} for subset {E}, MaxP={F} for subset {F}, and MaxP={G} for subset {G}.

In step 2208, the Q_max score module 2108 computes Q_Max on each subset of P_0. Recall that since the subsets in P_0 do not have any children, for each subset a in P_0, $$Q\_Max(a) = \max(Q\_Subset(a), Q\_Partition(MaximalPartitionChildren(a)))$$
$$= \max(Q\_Subset(a), Q\_Partition(a))$$
$$= \max(Q\_Subset(a), Q\_Subset(a)) = Q\_Subset(a)$$
$$= 0.5$$

In this example, the Q_max score module 2108 scores each subset with a value of 0.5. This Q_Max score is shown in FIG. 23 for each subset of partition 2302 as Q_Max=0.5.

In step 2210, we optionally record the maximal partition of each subset a in P_0 to be partition of the subset a that generated the Q_Max for that subset. Thus we record the MaximalPartition(a)=a in this initial partition.

Figure 23:
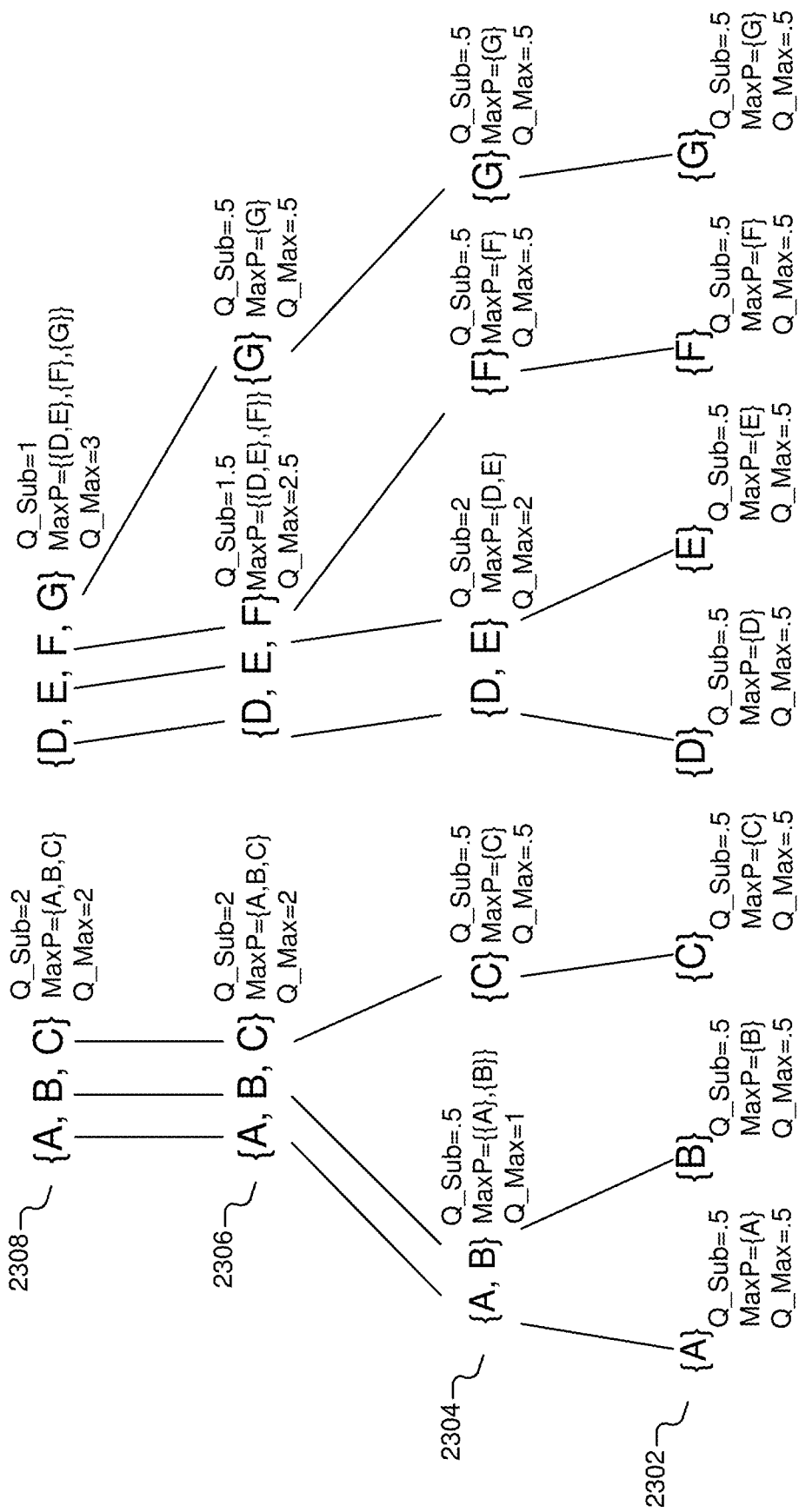
FIG. 23 depicts an example of determining a partition based on scoring in some embodiments.

In step 2212, the data structure module 2102 computes the next partition P_1 (the row labeled 2304 in FIG. 23). Namely, in this example, the data structure module 2102 groups subsets {A} and {B} into the subset {A, B} and subsets {D} and {E} into subset {D, E}. The data structure module 2102 preserved the subsets {C}, {F}, and {G} from the partition P_0 in the partition P_1.

It will be appreciated that the next partition P_1 may group subsets of previous partition(s) (e.g., partition 2304) in any number of ways. For example, the data structure module 2102 may group a predetermined number of subsets together at random and/or may group two or more subsets together based on the elements (e.g., based on the underlying data that the elements represent). In one example, the data structure module 2102 may group elements together using a distance metric and/or any other functions to define relationships in the underlying data and/or within a similarity space (e.g., reference space).

In various embodiments, the data structure module 2102 may determine whether the system ends and/or whether a new partition is to be computed. It will be appreciated that the data structure module 2102 may perform the determination based on any number of ways. In some embodiments, the data structure module 2102 determines if the next generated partition is equal to the previous partition. If the two partitions are equal (e.g., have the same subsets), the method may terminate, otherwise the method may continue to step 2214.

In some embodiments, the data structure module 2102 terminates the method after a predetermined number of partitions are generated, if a predetermined number of roots are found, and/or the like. In various embodiments, the data structure module 2102 may terminate the method if a predetermined number of subsets are present in a computed partition. In another example, the data structure module 2102 may terminate the method after a predetermined period of time, a predetermined period of memory usage, or based on any threshold (e.g., the threshold being calculated based on the amount of data received).

In step 2214, the Q_subset score module 2106 computes the Q_Subset score on each subset of the partition P_1. In this example, the Q_subset score module 2106 computes Q_Subset({A, B})=0.5 and Q_Subset({D,E})=2. In one example, the Q_subset score module 2106 calculates a modularity score for elements A and B for Subset {A,B} and a modularity score for elements D and E for Subset {D,E}. As discussed herein, the modularity score may be based on the edges of nodes A and B for Q_Subset({A, B}) modularity score and based on the edges of nodes D and E for Q_Subset({D, E}) modularity score.

As was discussed in the paragraph above describing step 2204, Q_Subset of each singleton subset is 0.5 (e.g., the previous Q_Subset score for singleton subsets in step 2304 remains unchanged from step 2302). These scores are associated with each subset and are visualized in the FIG. 23 as Q_Sub in 2304.

In step 2216, the Q_partition score module 2110 then computes the maximal partition at the children of each subset of P_1. The maximal partition of the children of the subsets {C}, {F}, and {G} are again the original singleton subset. The maximal partition of the children {A, B} is the set including the maximal partitions of the children of {A, B}, namely {{A}, {B} } as depicted in partition 2304 in FIG. 23. Similarly the maximal partition of the children of {D, E} is the set {{D}, {E}} as also depicted in partition 2304 in FIG. 23.

In step 2218, the Q_max score module 2108 computes the Q_Max on each subset of P_1. Recall Q_Max(a)=max (Q_Subset(a), Q_Partition(MaximalPartitionChildren(a)). For the subset {A, B}:

$$Q\_Max(\{A, B\}) = \max(Q\_Subset(\{A, B\}), Q\_Partition(\{\{A\}, \{B\}\}))$$
$$= \max(.5, Q\_Subset(\{A\}) + Q\_Subset(\{B\})$$
$$= \max(0.5, 1)$$
$$= 1$$

For the subset {D, E}:

$$Q\_Max(\{D, E\}) = \max(Q\_Subset(\{D, E\}), Q\_Partition(\{\{D\}, \{E\}\}))$$
$$= \max(2, Q\_Subset(\{D\}) + Q\_Subset(\{E\}))$$
$$= \max(2, 1)$$
$$= 2.$$

As displayed in partition 2304 of FIG. 23, Q_Max of {A,B} is 1 and Q_Max of {D,E} is 2. The Q_Max of singletons {C}, {F}, and {G} in partition 2304 remain consistent with the respective subsets in partition 2302. Namely, the Q_Max of each of {C}, {F}, and {G} is 0.5.

In step 2220, we optionally record the maximal partition of each subset a in P_1 that resulted in the Q_Max score. As seen above and in FIG. 23, MaxPartition({A, B})={{A}, {B}} and MaxPartition({D, E})={D, E}.

Step 2212 is repeated. The data structure module 2102 computes the next partition P_2, depicted in FIG. 23 as row (partition) 2306. In various embodiments, the data structure module 2102 may determine whether the system ends and/or whether a new partition is to be computed. It will be appreciated that the data structure module 2102 may perform the determination based on any number of ways.

In step 2214, the Q_subset score module 2106 computes the Q_Subset score on each subset of the partition P_2. In this example, the Q_subset score module 2106 computes Q_Subset({A, B, C})=2 and Q_Subset({D, E, F})=1.5. Again, Q_Subset({G})=0.5. These scores are recorded with each subset and are visualized in the FIG. 23 in partition 2306.

In step 2216, the Q_partition score module 2110 computes the maximal partition at the children of each subset of P_2. The maximal partition of the children{G} is the subset {G}. The maximal partition of the children {A, B, C} is the set consisting of the maximal partitions of the children of {A, B, C}, namely {MaxPartition({A,B}), MaxPartition({C})={{A}, {B}, {C}}. Similarly the maximal partition of the children of {D, E, F} is the set {MaxPartition({D, E}), MaxPartition({F})}={{D, E}, {F}}.

This is shown in FIG. 23 for each subset of partition 2306 as MaxP={A,B,C} for subset {A,B,C}, MaxP={{D,E},{F}} for subset {D,E,F,}, and MaxP{G} for subset {G}.

In step 2218, the Q_max score module 2108 computes the Q_Max on each subset of P_2. Recall Q_Max(a)=max (Q_Subset(a), Q_Partition(MaximalPartitionChildren(a)). For the subset {A, B, C}:

$$Q\_Max(\{A, B, C\}) = \max(Q\_Subset(\{A, B, C\}), Q\_Partition(\{\{A\}, \{B\}, \{C\}\}))$$
$$= \max(2, Q\_Subset(\{A\}) + Q\_Subset(\{B\}) + Q\_Subset(\{C\}))$$
$$= \max(2, 1.5)$$
$$= 2$$

For the subset {D, E, F}:

$$Q\_Max(\{D, E, F\}) = \max(Q\_Subset(\{D, E, F\}), Q\_Partition(\{\{D, E\}, \{F\}\}))$$
$$= \max(1.5, Q\_Subset(\{D, E\}) + Q\_Subset(\{F\}))$$
$$= \max(1.5, 2.5)$$
$$= 2.5$$

As displayed in partition 2306 of FIG. 23, Q_Max of {A,B,C} is 2 and Q_Max of {D,E,F} is 2.5 The Q_Max of singleton{G} in partition 2306 remains consistent with the respective subset in partition 2304. Namely, the Q_Max {G} is 0.5.

In step 2220, we optionally record the maximal partition of each subset a in P_2 that resulted in the Q_Max score. As seen above, MaxPartition({A, B, C})={{A, B, C} } and MaxPartition({D, E, F})={{D, E}, {F}}.

Step 2212 is repeated. The data structure module 2102 computes the next partition P_3, depicted in FIG. 23 as row (partition) 2308. The data structure module 2102 may determine whether the system ends and/or whether a new partition is to be computed.

In step 2214, the Q_subset score module 2106 computes the Q_Subset score on each subset of the partition P_3. In this example, the Q_subset score module 2106 computes Q_Subset({A, B, C})=2 and Q_Subset({D, E, F, G})=1. These scores are recorded with each subset and are visualized in FIG. 23 in partition 2308.

In step 2216, the Q_partition score module 2110 computes the maximal partition at the children of each subset of P_3. The maximal partition of the children {A, B, C} is the set consisting of the maximal partitions of the children of {A, B, C}, namely {MaxPartition({A,B, C})}={{A, B, C}. Similarly the maximal partition of the children of {D, E, F, G} is the set {MaxPartition({D, E, F}), MaxPartition ({G})}={{D, E}, {F}, {G}}.

This is shown in FIG. 23 for each subset of partition 2308 as MaxP={A,B,C} for subset {A,B,C} and MaxP={{D,E}, {F},{G}} for subset {D,E,F,G}.

In step 2218, the Q_max score module 2108 computes the Q_Max on each subset of P_3. Recall Q_Max(a)=max (Q_Subset(a), Q_Partition(MaximalPartitionChildren(a)). For the subset {A, B, C}:

$$Q\_Max(\{A, B, C\}) = \max(Q\_Subset(\{A, B, C\}), Q\_Partition(\{A, B, C\}))$$
$$= \max(2, Q\_Subset(\{A, B, C\}))$$
$$= 2$$

For the subset {D, E, F, G}:

$$Q\_Max(\{D, E, F, G\}) = \max(Q\_Subset(\{D, E, F, G\}), Q\_Partition(\{\{D, E\}, \{F\}, \{G\}\}))$$
$$= \max(1, Q\_Subset(\{D, E\}) + Q\_Subset(\{F\}) + Q\_Subset(\{G\}))$$
$$= \max(1, 3)$$
$$= 3$$

As displayed in partition 2308 of FIG. 23, Q_Max of {A,B,C} is 2 and Q_Max of {D,E,F,G} is 3.

In step 2220, we optionally record the maximal partition of each subset a in P_3 that resulted in the Q_Max score. As seen above, MaxPartition({A, B, C})={{A, B, C} } and MaxPartition({D, E, F, G})={{D, E}, {F}, {G}}.

Although not depicted in method 2200, the method may continue. For example, the partition selection module 2112 may identify and/or generate a preferred partition from that maximizes one or more scoring functions. In this example, the preferred partition is the MaxPartition. As discussed immediately above, the maximal partition of each subset in P_3 is MaxPartition({A, B, C})={{A, B, C}} and MaxPartition({D, E, F, G})={{D, E}, {F}, {G}}. The partition selection module 2112 may identify and/or generate the autogrouped partition {{A, B, C}, {{D, E}, {F}, {G}}.

The data control module 2114 may provide the identified and/or generated autogrouped partition in a report and/or identify the autogrouped partition in data or a graph.

Figure 24:
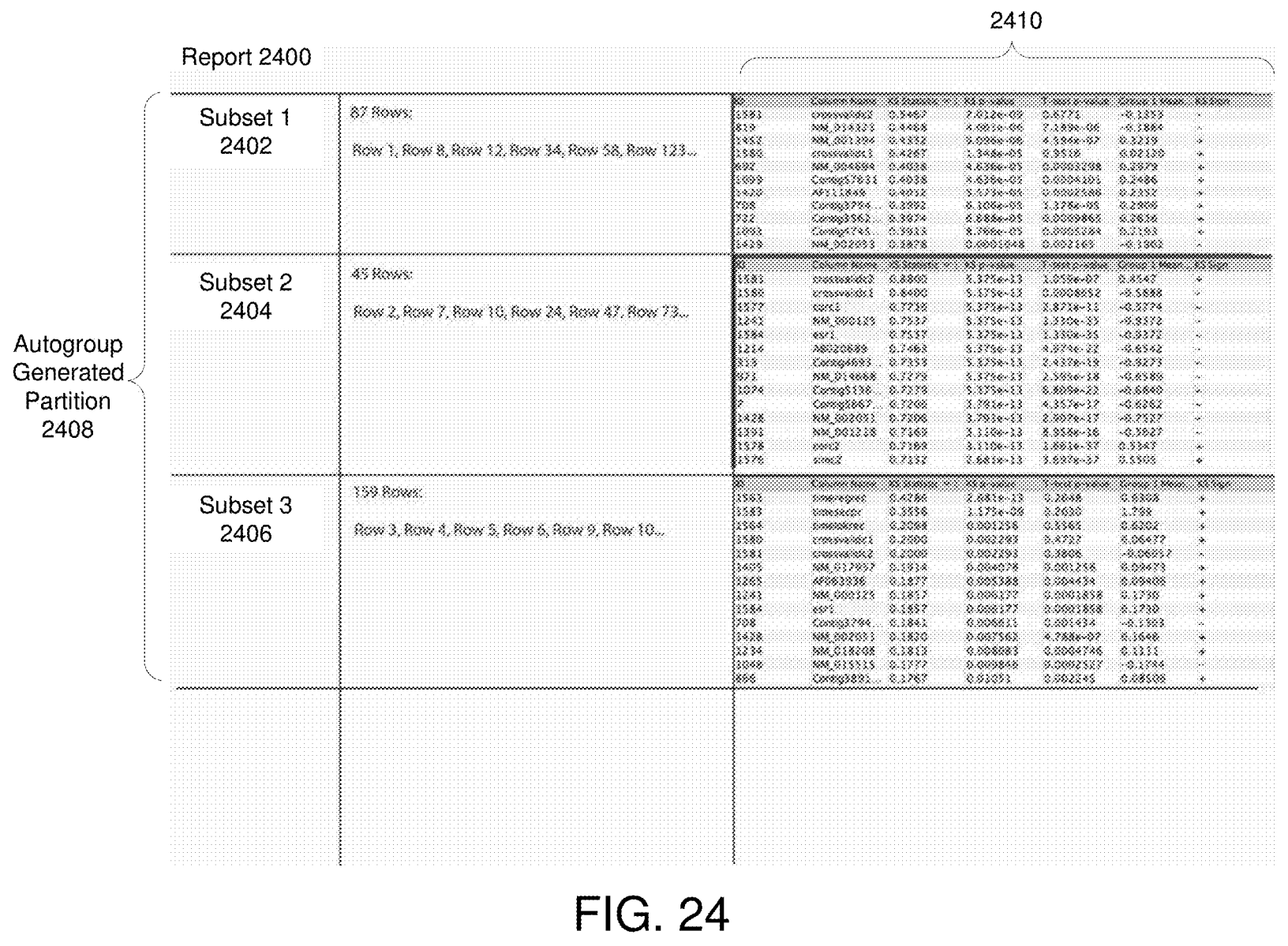

FIG. 24 is an example report 2400 of an autogrouped graph of data points that depicts the grouped data in some embodiments. Subsets 2402, 2404, and 2406 are subsets of data points that, together, make a partition (i.e., the autogrouped generated partition 2408). In various embodiments, data may be received and nodes generated utilizing embodiments described herein (e.g., see description regarding FIG. 4 or 8). The nodes that represent at least some of the received data may be autogrouped into a number of subsets 2402, 2404, and 2406 of an autogroup generated partition 2408. The report 2400 may depict the subsets including the rows of the underlying data associated and/or within each subset as well as all or some of the underlying data 2410 for that subset.

For example, the autogroup module 2002 may generate a report that shows each subset of datapoints for an autogroup generated partition. The rows, columns, or other data identifiers may be associated with each subset. Further, all or some of the data associated with each subset may be displayed (e.g., including any independent variables such as data identifiers, for example, patient identifiers).

The report may allow groups of nodes (e.g., nodes that are part of a subset of the output partition) to be identified. The identified groups of nodes may be identified in a visualization by coloring the nodes in a group a similar color, shape of nodes, a graphical element associated with nodes in a group (e.g., a box around nodes in a group), and/or in any number of ways. In some embodiments, the identified groups of nodes allow a user to create queries, analyze, and/or view data associated with nodes in a group for insights.

In some embodiments, autogrouping may be utilized on a weighted graph. In this example, the set that will be autogrouping is the set of nodes of a weighted graph G. The idea is to automatically partition the graph into groups of nodes that are strongly-connected in the graph. An unweighted graph may be transformed into a weighted graph if there is a function f on the nodes of the graph. The weight for an edge (a,b) between two nodes a and b in the graph G may be defined to be the difference between the function values: $wt(a,b)=|f(a)-f(b)|$. In another embodiment, this graph may be a visualization generated from a data set and the function on the nodes may be given by a color scheme on the nodes.

In one example, the input graph G may be generated from connecting points to their nearest neighbors, where the metric space is a set of 2200 points from 5 Gaussian samples in the Euclidean plane. The graph may be colored by the Gaussian density. The graph is made into a weighted graph by weighting each edge in G by the difference in the Gaussian density function at the edge's endpoints.

Figure 25:
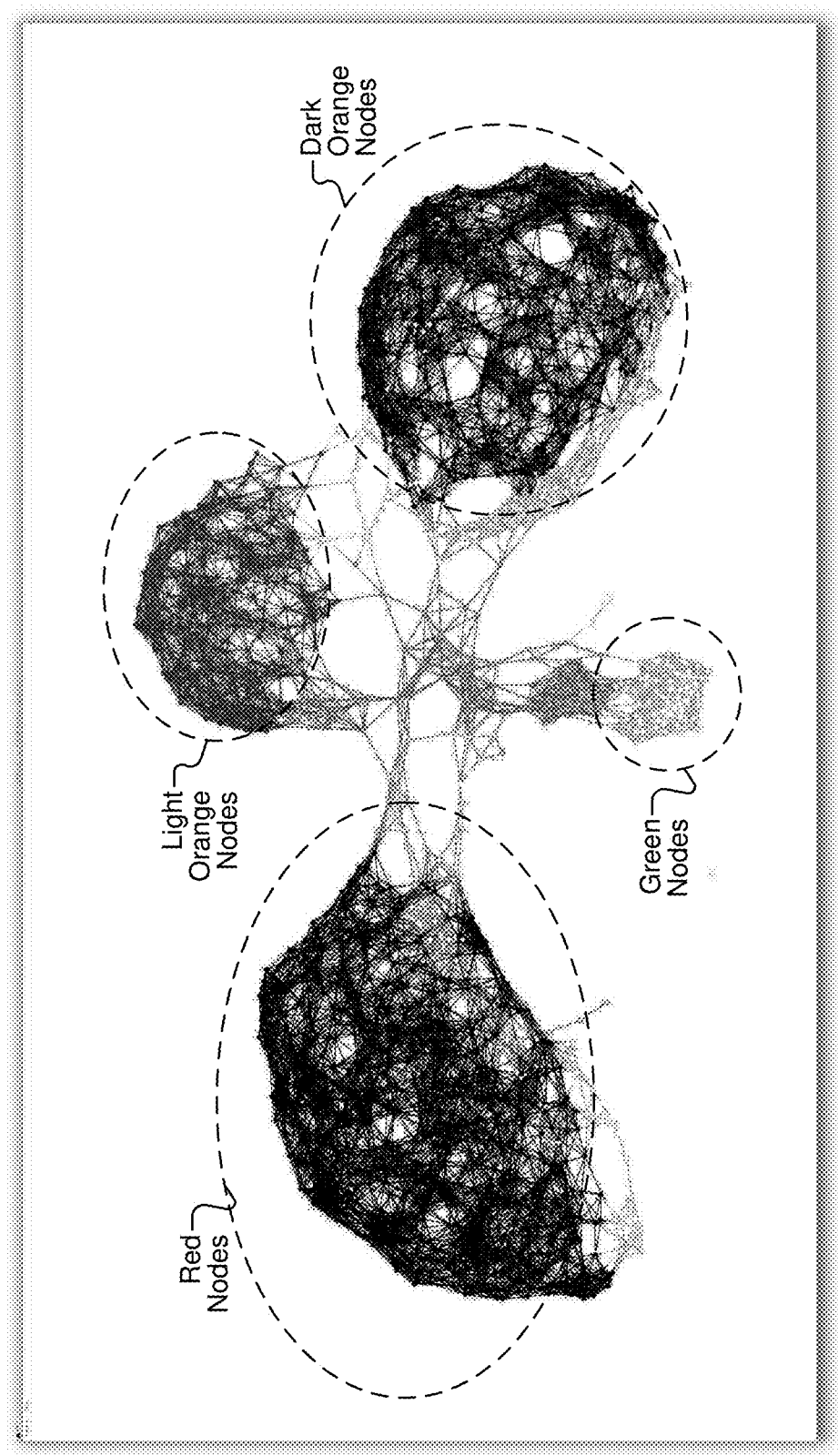
FIG. 25 is an example visualization generated based on an input graph, each edge being weighted by a difference of a density function at the edge endpoints.

The method is applied uses the scoring mechanisms described herein regarding weighted graphs and the modularity scorer applied to the weighted graph G. The resulting maximal partition may be "color coded" (utilizing greyscale) in FIG. 25.

Figure 26:
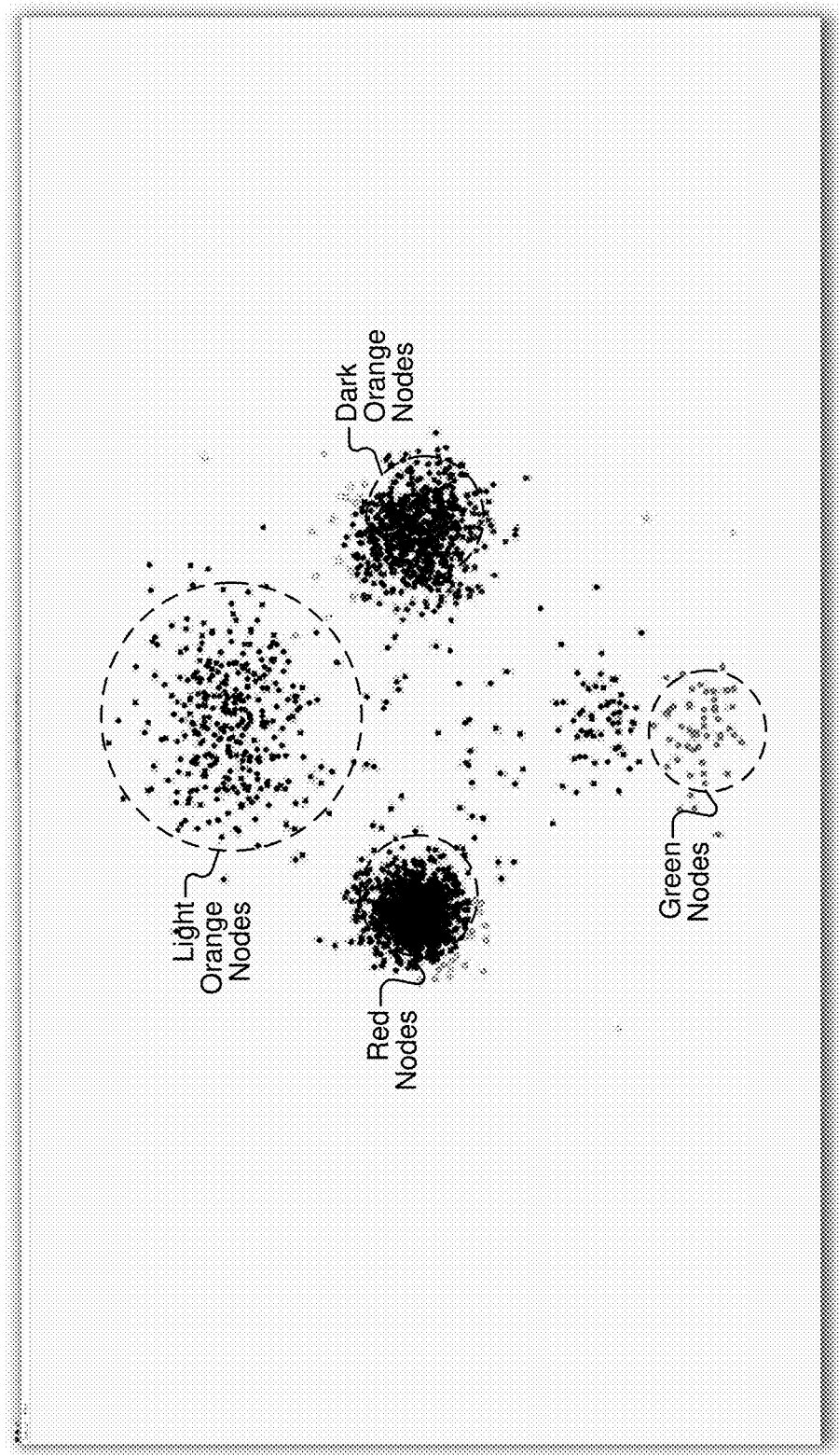
FIG. 26 is another example visualization generated using autogrouped partitions of a graph into regions that are strongly connected and have similar function values.

To elucidate the groups, we look at the corresponding points and assignments in a scatter plot of the points in the Euclidean plane in FIG. 26. As the graph G comes from the geometry in this data set, subtle geometric features are preserved in this decomposition. In other words, in this example, autogrouping partitioned the graph into regions of the graph that are strongly connected and have similar function (specifically density) values. This is helpful as the data points within each group are now very similar to each other drawing statistical conclusions from each subset is much more likely to be statistically significant.

In one application of this embodiment, the original data may be a data set that is input into the graph construction (e.g., as discussed regarding FIG. 8), which produces a graph (the graph may be in memory or a visualization). The visualization may be colored by the average value of a function of interest on the data points as discussed herein. One such coloring might be the outcome of interest for the data set such as survival of patients, power output in an electric generator, etc. The coloring is used to convert the graph (e.g., in memory or visualization) into a weighted graph that may be then autogrouped using one or more of the autogrouping embodiments described herein. Various autogrouping algorithm partitions the graph into subsets that are highly connected and have similar color values.

The groups may be used to create a new color scheme for the graph for use in a visualization. They may also be used for automatic statistical analysis and report generation. Moreover, this process may be used to start with the dataset, generate a graph (but not necessarily generate a visualization) (e.g., generate all or part of the graph in memory), and then report to the user the subsets of the final autogrouped maximal partition together with statistical calculations on those subsets.

As discussed herein, recall that once a filter is computed, data points may be mapped to a reference space and an open cover is generated in that reference space (see discussion regarding FIG. 8). The elements in the open cover may be iterated over, together with clustering, to generate the nodes in the resulting visualization. In one example described herein, the open cover may take intervals in the reference space (or cross-products of intervals in the case of more than one filter). The following embodiment is a data-driven alternative to generating the open cover in the reference space.

The set S in this embodiment are the projections of the original data points into the reference space (e.g., a function such as a gaussian density function is applied on the received data points to project to the reference space). The autogroup module 2002 may operate on a weighted graph built from this projection of the data into the reference space. For example, for a fixed positive integer k, construct a graph G on the set S by connecting each point a in S to every point b in S if b is one of a's k-nearest neighbors and a is one of b's k-nearest neighbors (i.e. they are symmetric k-nearest neighbors of each other). In some testing, k=20 produces good results. The edges of the graph may be weighted by the distance between the edge's endpoints in the embedded reference space distance. This autogrouping embodiment may utilize a hierarchical single-linkage clusterer that uses distance between points in the reference space. The scorer modules (e.g., modules 2106, 2108, and/or 2110 in FIG. 21) may utilize a modularity score built off of the weighted neighborhood graph G.

The result of this embodiment may be a partition P of the projection of the data points in the reference space. Now for a fixed positive integer j, we can expand each subset a of P by adding all the j-nearest neighbors in the reference space of the elements in the subset a. The new, expanded subsets may no longer be a partition as some points may now exist in multiple subsets but this new collection of subsets forms the open cover of the reference space (see discussion regarding FIG. 8) in the graph construction.

In various embodiments, autogrouping may be used for clustering. For example, in the embodiments described with regard to FIG. 8, after a cover is generated either in the reference space or in the original space, data is clustered on each of the subsets in the open cover to identify nodes (e.g., see steps 808-812). Autogrouping clustering may be an adaptive alternative to single linkage clustering with a fixed distance cut-off.

For example, the set S is a set data together with a metric which defines a distance between any two points in the set S. In the discussion regarding FIG. 8, these points may have come from the open cover in the reference space. In the current example, the partition generation module 2104 (see FIG. 21) and one or more of the score modules (e.g., the Q_Subset score module 2106, the Q_Max score module 2108, and/or the Q_Partition score module 2110) operate on a weighted neighborhood graph built from the data. For a fixed positive integer k, a graph G may be constructed on the set S by connecting each point "a" in S to every point "b" in S if "b" is one of "a's" k-nearest neighbors and "a" is one of "b's" k-nearest neighbors under the given metric (i.e. they are symmetric k-nearest neighbors of each other). In some instances, k=20 produces good results. The edges of this graph may be weighted by the distance between the edge's endpoints. The partition generation module 2104 for this autogrouping example is a hierarchical single-linkage clusterer that uses the distance between points determined by the given metric. The one or more of the score modules (e.g., the Q_Subset score module 2106, the Q_Max score module 2108, and/or the Q_Partition score module 2110) uses the modularity score built off of the weighted neighborhood graph G. The resulting clustering would likely have clusters formed at a variety of distance cut-offs instead of a single fixed distance cut-off for the set S.

In another example, the elements of the set S might have additional information such as an associated classification, that is, for example, a function cls: $S \rightarrow \{1, 2, \ldots, k\}$ (i.e. there is a set and everything has some finite label.) The one or more of the score modules (e.g., the Q_Subset score module 2106, the Q_Max score module 2108, and/or the Q_Partition score module 2110) may score entropy (e.g., one or more of the score modules may be an entropy scorer).

One example of an entropy scorer $Q(a) = \text{sum}\_\{\text{classes } i\} (p\_i(a)*\log(p\_i(a)))$ where $p\_i(a) = |\{x \text{ in } a: cls(x) == i\}|/|a|$, provided $|a|! = 0$. The extension of the entropy scorer Q to a partition scorer, QP is given by the extension property (3) where $A(p,q) = |p|/|q|$. In other words, for a partition P, $QP(P) = \text{sum}\_\{p \text{ in } P\} (Q(p)*|p|/|U(P)|)$. The combination of the partition generation module 2104 and one or more of the score modules (e.g., the Q_Subset score module 2106, the Q_Max score module 2108, and/or the Q_Partition score module 2110) may produce the maximal partition (i.e. clustering) of the elements of the set S that emphasizes clusters that are very close in distance and have the lowest entropy in class type in the subsets of the partition. In other words, this example embodiment may locate clusters that have the largest proportion of each single class type possible under the constraint of the distance metric.

In some embodiments, autogrouping may be used for open cover generation without a reference space. For example, in the embodiments described with regard to FIG. 8, a filter may be generated, points may be mapped to the reference space, and an open cover may be generated in that reference space (e.g., see steps 802-808). The elements in the open cover may be iterated over, together with clustering, to identify nodes. In some embodiments, the open cover may be constructed in the reference space. Various embodiments include a data-driven alternative to generating the open cover of the original data without the need to have a filter or a reference space.

In one example, the set S is the original data together with a metric which defines a distance between any two points in the set S. Both the partition generation module 2104 and the one or more of the score modules (e.g., the Q_Subset score module 2106, the Q_Max score module 2108, and/or the Q_Partition score module 2110) may operate on a weighted neighborhood graph built from the data. Specifically, for a fixed positive integer k, a graph G on the set S is constructed by connecting each point "a" in S to every point "b" in S if "b" is one of "a's" k-nearest neighbors and "a" is one of "b's" k-nearest neighbors under the given metric (i.e. they are symmetric k-nearest neighbors of each other). In some instances, k=20 produces good results. The edges of this graph may be weighted by the distance between the edge's endpoints. The partition generation module 2104 for this embodiment is a hierarchical single-linkage clusterer that uses the distance between points determined by the given metric. One or more of the score modules (e.g., the Q_Subset score module 2106, the Q_Max score module 2108, and/or the Q_Partition score module 2110) may use the modularity score built off of the weighted neighborhood graph G.

The result in this example is a partition P of the data points in the original space. For a fixed positive integer "j", we can expand each subset "a" of P by adding all the j-nearest neighbors of the elements in the subset "a". The new, expanded subsets may no longer be a partition as some points may now exist in multiple subsets but this new collection of subsets may form the open cover of the space for step 808 as described in FIG. 8.

It will be appreciated that many graphs may be generated for the same data. For example, TDA may be utilized with different filters, metrics, resolutions, or any combination to generate different graphs (and different visualizations) using the same large data set. Each graph may provide different insights based on the data's shape, character, or both. Different filters, metrics, resolutions, or combinations may generate different graphs that include different groupings of nodes. It may be advantageous for a data scientist to generate at least one graph that includes or depicts groupings of nodes that share a similar characteristic (e.g., outcome). These graphs with this type of groupings (e.g., if the groupings are coherent relative to other nodes in the same graph, relative to other nodes in other graphs, or both) may suggest insights or relationships within the data that were not previously available through query methods.

In some embodiments, different graphs may be generated on the same data using TDA methods described herein. Each different graph may be generated based on different filters, metrics, resolutions, or any combination. All or some nodes within each graph may be grouped based on a shared characteristic such as outcome. For example, if the outcome is survival, then nodes may be grouped based on those that survived and those that did not survive. In some embodiments, nodes are only grouped if they share the same outcome (e.g., they share the same shared characteristic), there is a sufficient number of nodes in the group, there is a sufficient number of connections between nodes between groups, or any combination. Each graph may be scored based on the groupings within that particular group. Each graph may then be ordered based on score and one or more of the graphs may be identified or provided to a user based on the ordered score (e.g., visualizations of the top three graphs based on best score is displayed or otherwise provided to the user).

It will be appreciated that this system of automatic outcome analysis may allow a data scientist to have data assessed through a variety of different filters, metrics, resolutions, or any combination to find a preferred graph without manual selection of each filter, metric, and resolution. Further, the data scientist may not be required to manually inspect each visualization of each graph to identify one or more graphs that have the best grouping of nodes based on outcome.

In various embodiments, systems and methods described herein may assist in identifying one or more graphs that best localizes an outcome or shared characteristic (e.g., of one or more columns in the data set). For example, a graph that best localizes an outcome may include or depict regions of the graph that have categories of or similar values from the outcome concentrated together). In some embodiments, systems and methods described herein may generate scores to identify metrics that are "continuous" with respect to the outcome column, identify lenses that have distributions of the outcome categories that are "localized," and choose lens parameters that are localized and separate outcome categories (or similar outcome values) without having too many singletons.

What is required is an approach that is somewhere between the macro and the micro that is both scalable and actionable. Many hospitals are beginning to use such an approach by focusing on identifying what can be aptly referred to as mid-level patterns of denials. A mid-level pattern is a medium-sized collection of denials, where the reason for the denials in coherent and specific. This reason is more specific than a reason for a macro-level pattern, such as "pre-certification imaging denials," and it is more significant than the reason for a micro-level pattern, such as "10 claim denials attributable to the same coding error by a single coder."

A mid-level pattern may be specific, actionable, and large enough to merit interest. To illustrate such a pattern, consider this example: A hospital has a problem with precertification denials on outpatient magnetic resonance imaging (MRI) scans with contrast in the following circumstances: when a diagnosis of sciatica is billed with one of two HCPCS codes, the facility is not fully integrated into the hospital's network of providers, the payer is private, and the employee responsible for obtaining the pre-certification has been with the hospital for less than six months. That scenario can be acted upon with a nuanced and specific intervention. It describes a collection of cases that is large enough to be meaningful, it is actionable enough to matter, and it draws upon the complexity of claims data.

Such mid-level patterns are difficult to identify using traditional analytics, ironically because traditional methods begin with people asking questions. As identified above, the possible number of questions is staggering, and even with domain expertise, it would not be feasible to consider that large of a subset of questions. In the case of our scenario, it is necessary to address denial type (pre-certification), procedure (MRI), account class (outpatient), procedure codes on claim (HCPCS), facility type (noninte-grated), payer type (private), and employment longevity of particular staff members. That is seven variables-translating into a highly complex query for a coder, and a daunting string of pivot tables for an analyst. Moreover, these seven variables are far from the only ones to consider, and It is unlikely that any one person will identify that specific set for a query, when there are so many other variables to choose from (e.g., patient status, referring provider's department, existence of an ECI code on the claim, and patient's age).

This point demonstrates the principle of combinatorial complexity. If an analysis captures 100 features of every claim, and realistically speaking that is a very low estimate, how many combinations of seven features are there? The answer is 16 billion. But what if a 10-feature combination was needed to characterize the pattern? It is precisely because of this combinatorial complexity that denials pose such a persistent and challenging problem. It is also why analytical techniques that make it easier to ask questions, or ask questions faster, or increase the number of people who can ask questions, are doomed to fail.

The flaw in the reasoning underlying such techniques is that it is possible to solve the problem just by asking the right questions. There are simply too many questions to ask.

Solving the denials problem requires a learning system designed to find answers by detecting relationships associated with the data to find finds answers without asking questions.

This is not to suggest that software eliminates people from the equation. On the contrary, people remain a critical part of any effort to drive denials down, but the new tools can help those people be far more efficient. With the advent of technologies such as machine intelligence, it is possible to leverage software and computing power to produce more complete answers in a fraction of the time it would take traditional technologies and a fraction of a fraction of the time it would take a person.

A machine intelligence framework may reveal subtle, interconnected elements of a particular payer's application, misapplication, or non-application of its own rules. Machines have the capacity to relentlessly uncover patterns in payer behavior, independent of the actual "rules," focusing on outcomes, behaviors, and subtlety and dispensing with concepts such as "should" and "intent." The 16 billion queries referenced earlier are replaced by a handful of meaningful patterns. Machine intelligence amplifies domain expertise and puts the provider on a different trajectory in the battle to eliminate claims.

In a healthcare context, topological data analysis (TDA) may help to uncover highly nuanced relationships and patterns hidden within historical claims data and automatically reveals the mid-level patterns that are actionable.

The TDA process starts by ingesting all the claims data (e.g., including UB-04 data elements and transactional information associated with each claim). TDA may then produce a visual network of all the claims based on a notion of similarity. These networks can be thought of as "similarity maps."

Claims with similar characteristics may be clustered closer together within the network, whereas claims that are less similar tend to be further apart. The determination of similarity comes from complex combinations of all of the features known about a claim. Traditional reporting using dashboards and Excel sheets may show aggregate numbers, but those tools are unable to show the relationships between similar claims.

Similarity maps can be colored by any attribute of interest, including the payer type, denial reason category (e.g., medical necessity, pre-certification), diagnostic and procedure codes reported in the claim, or percentage of claims denied. By selecting these variables, it is possible to uncover subtle patterns in the claims data.

Coloring the similarity maps by whether a claim was denied or rejected reveals hotspots, or dense clusters, of denied/rejected claims within the network. These hotspots are generated without having to input any preconceived notions of the underlying reasons for denial.

Eliminating the bias associated with a question-first approach allows for a true, data-first methodology that is open to all the possibilities associated with the data set, not just the ones the analyst puts into play-or takes out of play-with a query.

By breaking the query model, analysts and medical billing specialists no longer have to guess or check which procedures, providers, and reason codes are in common within groups of denied claims. By drilling into a hotspot, an analyst can quickly determine the characteristics that drive denials and that differentiate them from the rest of the claims.

Software efficiently distinguishes denied claims by identifying the unique combination of diagnostic codes, payer, and procedure attributes that characterize these denied claims. Based on these attributes, claim analysts can now create meaningful, actionable profiles of claims known to have a high risk of denial.

More important, an approach like this one creates a process flow that can operationalize the handling of these valuable mid-level patterns.

Once the mid-level patterns of denials have been identified, action is required to resolve those patterns. The first step in this process is to identify the drivers of patterns group by group. Some differ from payer to payer, others from procedure to procedure, and so on. Clearly, some MRI denials have one kind of driver, while others have a different one. For example, one group of MRI pre-certification denials might be driven by orders from referring physicians that are changed (e.g., from with to without contrast) by radiology without updating the pre-certification. Another group of MRI pre-certification denials might be driven by MRIs that are unnecessarily ordered with urgent status. The general category "MRI pre-certification denials" is macro-level-understandable with traditional tools, but too general to be actionable. The more specifically the group can be narrowed down, the more targeted an intervention can be. Narrowing the first example further, one might find that this process problem is occurring primarily in two radiology departments, and primarily with MRIs related to a certain diagnosis. Narrowing the second example further, it might turn out that MRIs are being unnecessarily ordered with urgent status primarily when the patient lives in a rural area without convenient access to an imaging center.

The next step is to establish priorities for work queues by identifying where the denial originated (e.g., which work group bears responsibility for it). This process can be streamlined by giving the person working the work queue a disposition, which is a summary of the detailed reason for denial. For example, the first group of denials above might be labeled "MRI pre-certs changed by radiology" while the second might be labeled "MRI pre-certs unnecessarily ordered urgent." The person reading the label would have access to the detailed description of the group and would prioritize and direct resolution accordingly.

The third step is to make the necessary modifications to upstream processes to address the drivers of the denials, changing what needs to be changed with precise solutions, thereby minimizing disruption in the revenue cycle. The first example above would suggest a targeted process improvement effort in two radiology departments, or perhaps an EHR reminder targeted at only MRI orders with the relevant diagnosis and only presented to personnel in the relevant departments. The second example, on the other hand, would suggest an education effort targeted at referring providers operating in rural areas.

Moreover, highlighting mid-level patterns of denial and defining their causes provides a basis for more easily addressing a newly denied claim: If such a claim is recognized as having attributes similar to the claims reviewed in a hotspot, it can quickly be categorized and prioritized for correction. The reason for denial is likely to be the same, which limits the investigation effort required to determine the root cause of the denial and, as a result, greatly improves the billing team's efficiency and the overall claims denial management process.

People continue to be involved, but at a stage that optimizes the process, speeds detection, and leverages the relationships discovered elsewhere. People can further analyze the classes of denied claims to proactively improve upstream coding changes by the medical staff that will avoid future denials. Instead of evaluating individual denied claims, a domain expert evaluates groups of similarly denied claims and suggests process improvements using the underlying characteristics of each denial group. By identifying, modifying, and fixing processes upstream, hospitals can minimize the number of claims rejected or denied.

A New Framework for Addressing Denials

The reason hospitals face such a persistent problem with denials today is that they too often use tools and software that are insufficient to address the complexity of the problem. Meanwhile, with the advent of ICD-10, that complexity continues to grow. With the emergence of tools such as TDA, however, hospitals can develop a new framework that is vastly more effective for addressing the problem of denials because it acknowledges the complexity of the undertaking. Simply put, machine intelligence provides the means for identifying mid-level patterns of denials and pointing the way to their solution. And in so doing, it also provides a means to smooth the inevitable revenue bumps associated with the transition to value-based care.

Figure 27:
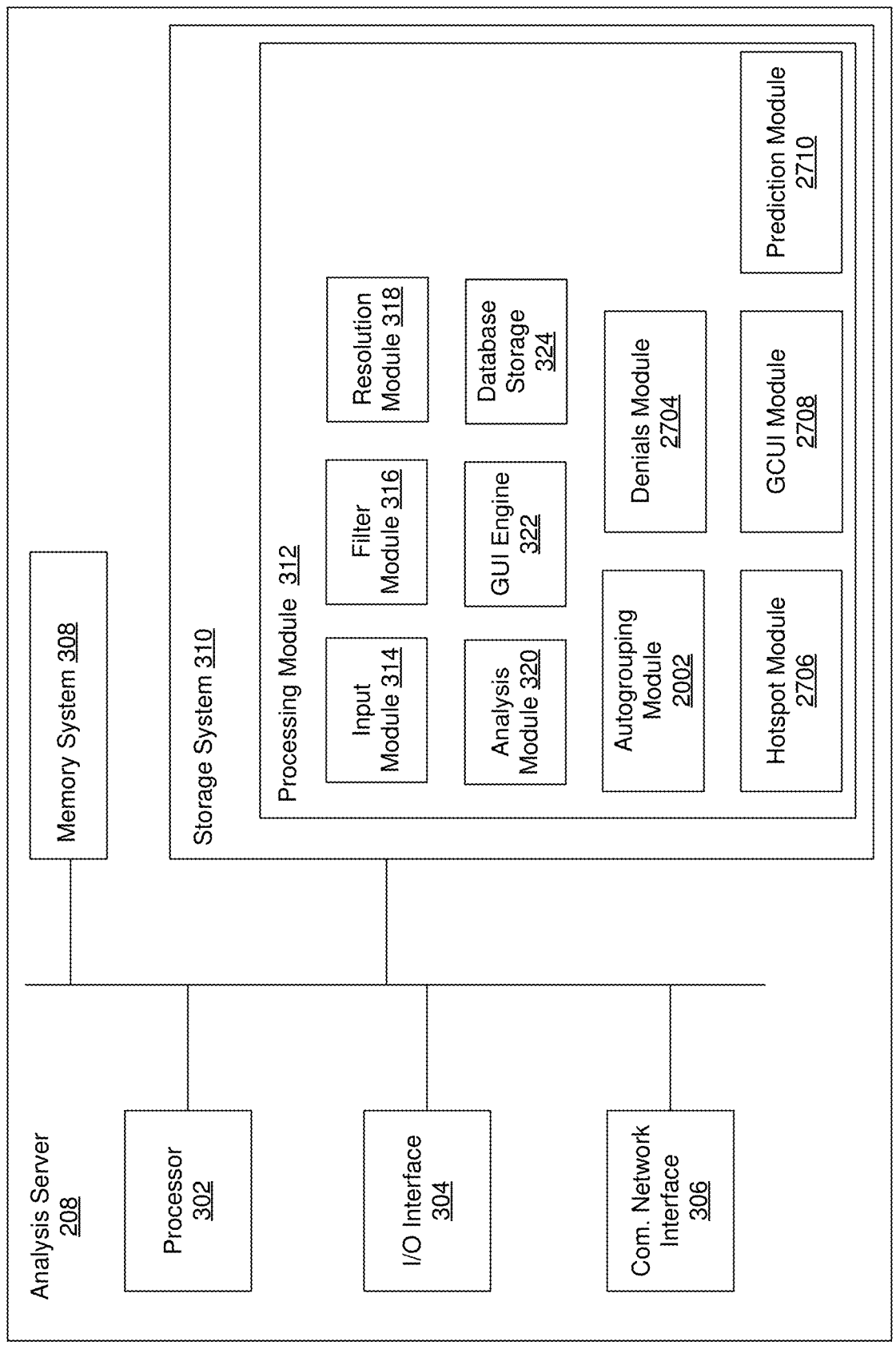
FIG. 27 is a block diagram of an example analysis server some embodiments.

FIG. 27 is a block diagram of an example analysis server 208 including an autogrouping module 2002, a denials module 2704, a hotspot module 2706, a GCUI module 2708, and a prediction module 2710 in some embodiments. The example analysis server 208 depicted in FIG. 27 may be similar to the example analysis server 208 depicted in FIG. 2 and FIG. 3. In example embodiments, the analysis server 208 comprises a processor 302, input/output (I/O) interface 304, a communication network interface 306, a memory system 308, and a storage system 310.

The storage system 310 comprises a plurality of modules utilized by embodiments of the present invention. A module may be hardware (e.g., an ASIC), software (e.g., including instructions executable by a processor), or a combination of both. In one embodiment, the storage system 310 comprises a processing module 312 which comprises an input module 314, a filter module 316, a resolution module 318, an analysis module 320, a visualization engine 322, a database storage 324, an autogrouping module 2002, a denials module 2704, a hotspot module 2706, a GCUI module 2708, and a prediction module 2710. Alternative embodiments of the analysis server 208 and/or the storage system 310 may comprise more, less, or functionally equivalent components and modules.

The input module 314 may be configured to receive commands and preferences from the user device 202a. In various examples, the input module 314 receives selections from the user which will be used to perform the analysis. The output of the analysis may be an interactive visualization.

The input module 314 may provide the user a variety of interface windows allowing the user to select and access a database, choose fields associated with the database, choose a metric, choose one or more filters, and identify resolution parameters for the analysis. In one example, the input module 314 receives a database identifier and accesses a large multi-dimensional database. The input module 314 may scan the database and provide the user with an interface window allowing the user to identify an ID field. An ID field is an identifier for each data point. In one example, the identifier is unique. The same column name may be present in the table from which filters are selected. After the ID field is selected, the input module 314 may then provide the user with another interface window to allow the user to choose one or more data fields from a table of the database.

Although interactive windows may be described herein, it will be appreciated that any window, graphical user interface, and/or command line may be used to receive or prompt a user or user device 202a for information.

The filter module 316 may subsequently provide the user with an interface window to allow the user to select a metric to be used in analysis of the data within the chosen data fields. The filter module 316 may also allow the user to select and/or define one or more filters.

The resolution module 318 may allow the user to select a resolution, including filter parameters. In one example, the user enters a number of intervals and a percentage overlap for a filter.

The analysis module 320 may perform data analysis based on the database and the information provided by the user. In various embodiments, the analysis module 320 performs an algebraic topological analysis to identify structures and relationships within data and clusters of data. It will be appreciated that the analysis module 320 may use parallel algorithms or use generalizations of various statistical techniques (e.g., generalizing the bootstrap to zig-zag methods) to increase the size of data sets that can be processed. The analysis is further discussed in FIG. 8. It will be appreciated that the analysis module 320 is not limited to algebraic topological analysis but may perform any analysis.

The visualization engine 322 generates an interactive visualization including the output from the analysis module 320. The interactive visualization allows the user to see all or part of the analysis graphically. The interactive visualization also allows the user to interact with the visualization. For example, the user may select portions of a graph from within the visualization to see and/or interact with the underlying data and/or underlying analysis. The user may then change the parameters of the analysis (e.g., change the metric, filter(s), or resolution(s)) which allows the user to visually identify relationships in the data that may be otherwise undetectable using prior means. The interactive visualization is further described in FIGS. 9-11.

The database storage 324 is configured to store all or part of the database that is being accessed. In some embodiments, the database storage 324 may store saved portions of the database. Further, the database storage 324 may be used to store user preferences, parameters, and analysis output thereby allowing the user to perform many different functions on the database without losing previous work.

The denials module 2704, hotspot module 2706, GCUI module 2708, and a prediction module 2710 (and, optionally, the autogrouping module 2002) may work together to report or assist in identifying patterns of denials without querying on the original data set (e.g., in a query-less approach). In various embodiments, machine intelligence may automatically assess large batches of adjudicated medical claims to identify and characterize patterns of denials of medical claims to disseminate guidance (e.g., into operational workflows) and enable health systems to pursue systematic initiatives to assist in preemptively preventing denials from health insurance companies.

In some embodiments, the denials module 2704, hotspot module 2706, GCUI module 2708, and a prediction module 2710 (and, optionally, the autogrouping module 2002) may work together to generate a report or assist in identifying those features (e.g., columns of data) that are most significantly related to patterns of improper medical claim denials to create a particular denial criteria (e.g., a criteria of medical claim denials that were similarly and improperly denied). Moving forward, the prediction module 2710 may receive denials from one or more payers and compare features, attributes, and/or metadata to particular criteria of medical claim denials to identify claims that may have been improperly denied.

In various embodiments, the input module 314 may receive data regarding a number of entities (e.g., providers of health care, customers, network service providers, or the like). Each entity may be associated with a variety of features (or characteristics) which may be structured into columns. In a health care example, the received data may include medical claim denials related to health data for services claimed to have been rendered and/or to be rendered to any number of patients by any number of health service providers.

The data may be structured such that each row is associated with a different health care provider and each column (i.e., feature) is associated with health care information. Data features may include but are not limited to:

Fields from adjudicated claims
   Electronic reason codes exchanged in electronic transactions between the health system's claims system and health insurance companies' adjudication systems
   Payment adjustment transactions associated with the adjudication history of each claim In some examples, data may be or include health care information may include any number of billing code(s), cost(s) for procedure(s), tests, medical coding, coverage, drug purchase(s), equipment rental(s), equipment purchase(s), health service rendered, care provided, treatment(s), facility usage, clinical workflow, or the like. For example, each column each column (i.e., feature) may include a different billing code and/or cost for a procedure, test, drug purchase, equipment rental, equipment purchase, health service rendered, care provided, or the like. In this example, at least one column of the data may identify the health care provider by name, identification number, code, or the like. The data may further include a provider's health summary information such as number of visits by the same or different patients, number of similar tests performed, number of days service was provided to one or more patients, number of days one or more patients was admitted (e.g., at a hospital) for care, outcomes, and the like.

In another example, each row in the data may be a patient account (HAR) or associated with the patient account. In some embodiments, each row of in the data may be a patient account regarding one procedure or medical treatment that was denied. The columns may be drawn from the data on UB-04 claim forms, along with records of how the claims moved through the payments and appeals process. Outcomes may include rejections and write-offs.

The following are example features (e.g., columns) for each row:

| | |
|---|---|
| bill_type = | indicators of which bill type a claim had |
| dollars = | features related to the amount rejected or written off on a claim |
| dx_code_counts = | counts of how many times common diagnosis codes appeared on a claim |
| hcpcs_code_counts = | counts of how many times common HCPCS codes appeared on a claim |
| payors = | indicators of whether various payers were primary on a claim |
| prin_dx_code_counts = | indicators of whether various diagnosis codes appeared as the principal diagnosis code on a claim |
| prin_dx_overrep_hcpcs_overrep_medicare = | a combination of certain principal diagnosis codes with certain HCPCS codes and with an indicator of whether Medicare was the primary payor on a claim |
| providers = | indicators of which provider (hospital, clinic, etc.) appeared on a claim |
| px_code_counts = | counts of how many times common ICD-9 procedure codes appeared on a claim |
| rejections_writeoffs = | indicators of rejection or write-off, for any reason and for medical necessity specifically |
| rev_code_counts = | counts of how many times each revenue code appeared on a claim |
| timelines = | features related to admit and discharge timing, length of stay |

In some embodiments, for several of these column sets, there may be two variants: "common" and "over-represented." The "common" column set is the codes that occur most frequently on claims in this dataset. The "over-represented" column set is the codes that are most strongly correlated with rejection for medical necessity. In some embodiments, the data contains other columns of other data features, or fewer.

The input module 314 may receive data from any number of sources (e.g., from any number of health service providers and/or insurers). The data may be structured or unstructured. In one example of unstructured data, the input module 314 or another entity may receive any number of adjudicated claims indicating denial or and/or write-offs. The documents or records may include any amount of health care information discussed herein. In some embodiments, the documents or records may include any amount of health summary information. The data may include an outcome column indicating a denial and/or reasons for denial.

The input module 314 and/or another entity (e.g., a hospital system or insurer) may structure the data for analysis based on the documents, records, and/or any other information. In some embodiments, the input module 314 and/or another entity may generate new features based on existing features (e.g., by creating a new column based on previously provided information that may be within other columns).

In some embodiments, an optional normalization module (not depicted) may normalize data within columns to assist with analysis. In some embodiments, the normalization module 2702 normalizes and/or scales data within one or more columns and creates new columns (e.g., new features) based on the previous normalized and/or scaled data. For example, the normalization module may create a new column based on previously received utilization features (e.g., contained within the health summary information). Utilization features may include, for example, a number of visits, number of procedures, number of units (e.g., of a drug or equipment) per patient, number of units per visit, and/or the like.

To normalize, the normalization module may normalize data within a column. For example, the normalization module may generate a z score for each entry in the column. The z score may be, for example, the original value for the entry subtracting the mean for the column divided by the standard deviation for the column. In various embodiments, the normalization module does not change the previous column but rather creates a new column (e.g., a new feature set) with the computed z scores. In other embodiments, the normalization module may generate counts for features (e.g., dx_code_counts, hcpcs_code_counts, prin_dx_code_counts, px_code_counts, and/or rev_code_counts). In some embodiments, the counts for features are received from one or more other sources (e.g., medical record depository).

Similarly, the normalization module or another digital device may generate features based on metadata and/or other features. For example, the normalization module may determine a timeline based on the adjudicated claim data and/or prin_dx_overrep_hcpcs_overrep_medicare.

In some embodiments, the normalization module may scale existing or new columns. In scaling, the normalization module may scale variables from 0 to 1 for equal contribution to ranking a calculating. In one example, the normalization module may scale the normalized data of each entry in the new normalized column (e.g., the z scores) by the following formula: (normalized data entry—minimum of the normalized column)/(maximum of the normalized column—minimum of the normalized column).

The input module 314 and/or the normalization module may select a subset of columns for analysis. For example, the input module 314 and/or the normalization module may select any number of newly created columns and/or features and not select one or more previously created or received columns and/or features for analysis.

The denials module 2704 and/or the prediction module 2710 may identify patterns in denial, refusal, write-offs and/or the like in many different ways. In some embodiments, the denials module 2704 and/or the prediction module 2710 identifies providers with health care information and/or health summary information patterns of attributes, dimensions, and/or metadata that is characteristic of known cases of improper denials In another example, the denials module 2704 and/or the prediction module 2710 may identify those payers that generate a higher number of improper denials to assist with those denials and/or identify patterns of improper information that may lead to denials.

For example, the input module 314 may receive adjudicated claims data (e.g., including the any number of the features discussed herein). The adjudicated claims data may include a first set of health care information which may include health summary information, and known denials. The adjudicated claims data may include reasons for denials (e.g., in text form and/or from a selection of predetermined choices). Analysis data may include data to be analyzed (e.g., structured or unstructured data based on or including any or all adjudicated claims data).

The analysis data may include identifiers for a plurality of payers to be analyzed. The analysis data may also include health care information for any number of payers and/or health summary information of any number of payers. Different payers may have different health care information, adjudication codes, reasons for denials, and/or different health summary information.

It will be appreciated that insurers, hospital systems, enforcement entities, healthcare systems, providers, and the like may analyze or investigate to determine or confirm evidence (e.g., providers and/or health care data) as being associated with improper denials. For example, an investigator or analyst may investigate a payer, the payer's health care information, and/or the payer's health summary information to determine if the provider is involved in fraud, waste, and/or abuse. As a result of the investigation, the investigator or analyst may identify the payer, all or some of the payer's claims information, attributes for claim denial, and/or the like.

The denial module 2704 and/or the prediction module 2710 may identify improperly denied claims and patterns in improperly denied claims. As such, the prediction module 2710 may receive new claims and compare the new claims to features associated with groups of improperly denied claims to generate a flag or alert if one or more of the new claims are similar to the improperly denied groups of claims (e.g., by generating a notification or flag associated with the one or more claims that are similar to the improperly denied groups of claims).

In various embodiments, the filter module 316 may receive one or more metric selection(s), one or more lens selection(s), a resolution and a gain as described herein. In this example, the filter module 316 may filter the received data to remove any portion of the data. In one example, the filter module 316 may choose one or more features or columns from the multidimensional data (e.g., each dimension being a feature). The filter module 316 may also receive one or more metric and/or lens selections. In one example, the filter module 316 receives a metric selection for variance normalized Euclidean (VME) and a lens selection of Gaussian Density & L-Infinity Centrality. The filter module 316 may also receive, for example, a resolution 30, and a gain of 2.5 as a starting point. It will be appreciated that the filter module 316 may apply any metric or combination of metrics. Similarly, the filter module 316 may apply any lens or combination of lenses.

As discussed herein, the analysis module 320 and/or the GUI engine 322 may generate a TDA graph using the claims data and the known improper denials to generate a TDA graph with nodes and edges. Each node may have membership of one or more providers (e.g., provider data points). Nodes that are connected share at least one provider as a member.

The denials module 2704 may identify payers and/or claims from the analysis data (i.e., those denials that are not a part of the known improper) that include similarities with claims that have been improperly denied.

In one example, the denials module 2704 may identify those claims from the claims data that are members of a node which also has at least one other member that includes a known improperly denied claim. In another example, the denials module 2704 may identify those claims from the claim data that are members of a node that also has a predetermined number of members that are known to be claims that have been improperly denied. In a further example, the denials module 2704 may identify those claims from the claim data that are members of a node that also has a number of members that are known claims that have been improperly denied that is equal or greater than a predetermined threshold or percentage of node membership (e.g., the number of claims that have been improperly denied is greater or equal to a threshold value when compared to a total number of members of the node).

In some embodiments, the denials module 2704 may also identify providers from the analysis data that are in nodes that are linked (i.e., with an edge) to a node containing at least one claim known to be improperly denied, to a node containing a number of claims known to be improperly that is equal to or greater than a predetermined number, or to a node containing a number of claims known to be improperly that is greater or equal to a threshold value when compared to a total number of members of the node (e.g., equal to or greater than a percentage).

In some embodiments, the denials module 2704 may receive node selections or claim selections from a user or another digital device based on the TDA graph. For example, the GUI engine 322 may generate a visualization of the TDA graph for the user or the digital device. The user or digital device may identify one or more claims or nodes for a report based on proximity, linking, node membership, or any other information. The claims identified in the report may be identified for further investigation for possible improper denials.

In one example, a user or a digital device may provide commands to the analysis server 208 to perform an additional function(s) on the features of the providers (e.g., a Euclidean function and/or L1) and color the visualization by the result (based on the result of the function(s)). In this example, the function(s) may be performed for a set of features of a provider. For each feature, the function(s) may be performed relative to that feature for that particular provider relative to the features of the other providers (e.g., all providers or those providers from the analysis data). The user may select any number of providers from the analysis data based on shared-membership of nodes (e.g., being a member of node that has members of one or more providers from the known data) and/or color of the visualization (e.g., based on the result of the function(s)).

A reporting module (not depicted) may, in some embodiments, generate a report listing those claims that may be improperly denied (e.g., identified by the denial module 2704). In some embodiments, the reporting module may generate a report listing those groups with the most significant number of improper claim denials or share characteristics of such groups (e.g., based on similarity as defined, at least in part, by distance between dimensions of member claims).

A ranking module (not depicted) may rank the claims or groups of claims. In one example, the ranking module ranks (e.g., sorts) each identified claim that has been or may be improperly denied. The ranking module 2708 may rank groups based on most significant number of improper claim denials or share characteristics of such groups (e.g., based on similarity as defined, at least in part, by distance between dimensions of member claims).

In some embodiments, the ranking module may identify and rank features of the groups that that may be outliers based on L1, L Infinity, or the like. As discussed herein, the analysis server 208 to perform an additional function(s) on the features of the providers (e.g., a Euclidean function and/or L1). The function(s) may be performed for a set of features of a provider. For each feature, the function(s) may be performed relative to that feature for that particular group relative to the features of the other groups. The ranking module may rank a predetermined number of features for each provider based on the function score(s). In some embodiments, the ranking module may rank or identify features with function score(s) at or above a predetermined threshold.

In various embodiments, metric(s) and/or lens(es) may be utilized in generation of the TDA graph to identify nodes that are separated from others (e.g., extreme or significant dissimilarities with other providers' health care information and/or other providers' health summary information which may indicate outliers).

The denial module 2704 may identify those claims or groups that are dissimilar (e.g., outliers or extreme) when compared to other claims or groups (e.g., other groups' features). In various embodiments, the filter module 316 may receive one or more metric selection(s), one or more lens selection(s), a resolution and a gain as described herein. In this example, the filter module 316 may receive selections of Cosine with Gaussian Density and L-infinity Eccentricity. It will be appreciated that the filter module 316 may receive and utilize any number of metric(s) and any number of lens(es).

The analysis module 320 and/or the GUI engine 322 may generate a TDA graph using the analysis data and the known fraud or abuse data to generate a TDA graph with nodes and edges. Each node may have membership of one or more providers (e.g., provider data points). Nodes that are connected share at least one provider as a member.

The denial module 2704 may further apply functions to the analysis data such as, for example, L1, L Infinity, or the like. As discussed herein, the analysis server 208 to perform an additional function(s) on the features of the claims or groups (e.g., a Euclidean function and/or L1). The function(s) may be performed for a set of features of a provider to generate a claim score (i.e., using the function(s)) for the claim and/or a feature score for any number of features of the claim using the function(s). For each feature, the function(s) may be performed relative to that feature for that particular claim relative to the features of the other claims. In various embodiments, the function(s) may be performed for a set of features of a provider to generate a group score (i.e., using the function(s)) for the claim and/or a feature score for any number of features of the group using the function(s). For each feature, the function(s) may be performed relative to that feature for that particular group relative to the features of the other groups.

The denial module 2704 may identify the claims or groups with the highest claim scores and/or highest feature score(s). For example, the denial module 2704 may identify a predetermined number of claims or groups based on highest claim score and/or highest feature score. In another example, the fraud or denial module 2704 may identify claims or groups in a claims or groups list with a claim score and/or feature score above a predetermined threshold. It will be appreciated that the denial module 2704 may identify any number of providers in the claim list using or based on the claims or groups score(s) and/or the feature score(s) in any number of ways.

In some embodiments, the denial module 2704 may apply L1 for a feature of a claim against that feature of other claims to generate a score. The denial module 2704 may perform this calculation for any number of features of any number of providers. The value of the score (e.g., the largest scores above a predetermined threshold or top largest scores) of any feature or combination of features may indicate claims or groups that may be further assessed, analyzed, or investigated.

In some embodiments, the analysis module 320 and/or the GUI engine 322 may identify those claims or groups with the highest L1 extremities score, based on position in the TDA graph which the least density of other nodes, lack of links with other nodes, lack of membership of a node with other providers (e.g., no other members of the nodes or other members being below a threshold), or the like.

In some embodiments, the denial module 2704 may receive node or group selections from a user or another digital device based on the TDA graph. For example, the GUI engine 322 may generate a visualization of the TDA graph for the user or the digital device. The user or digital device may identify one or more nodes or groups for a report based on proximity, linking, node membership, or any other information. The providers identified in the report may be identified for further investigation for improper denials and/or to study known improper denials.

The reporting module (not depicted) may, in some embodiments, generate a report listing those claims or groups identified by the denial module 2704. The reporting module may generate the listing based on claims or groups identified by the denial module 2704, another user, or another digital device.

While, as previously discussed, examples of claim denials are used herein, it will be appreciated that systems and methods herein may be applied to any industry or field (i.e., not limited to health care). For example, in some embodiments, systems and methods described herein may be applied to determining if entities are utilizing resources or systems without authorization (as discussed with regard to FIG. 25), financial fraud (e.g., by financial entities, money or financial instrument transferors or transferees, money laundering, laboratory mistakes or abuse), or the like.

Figure 28:
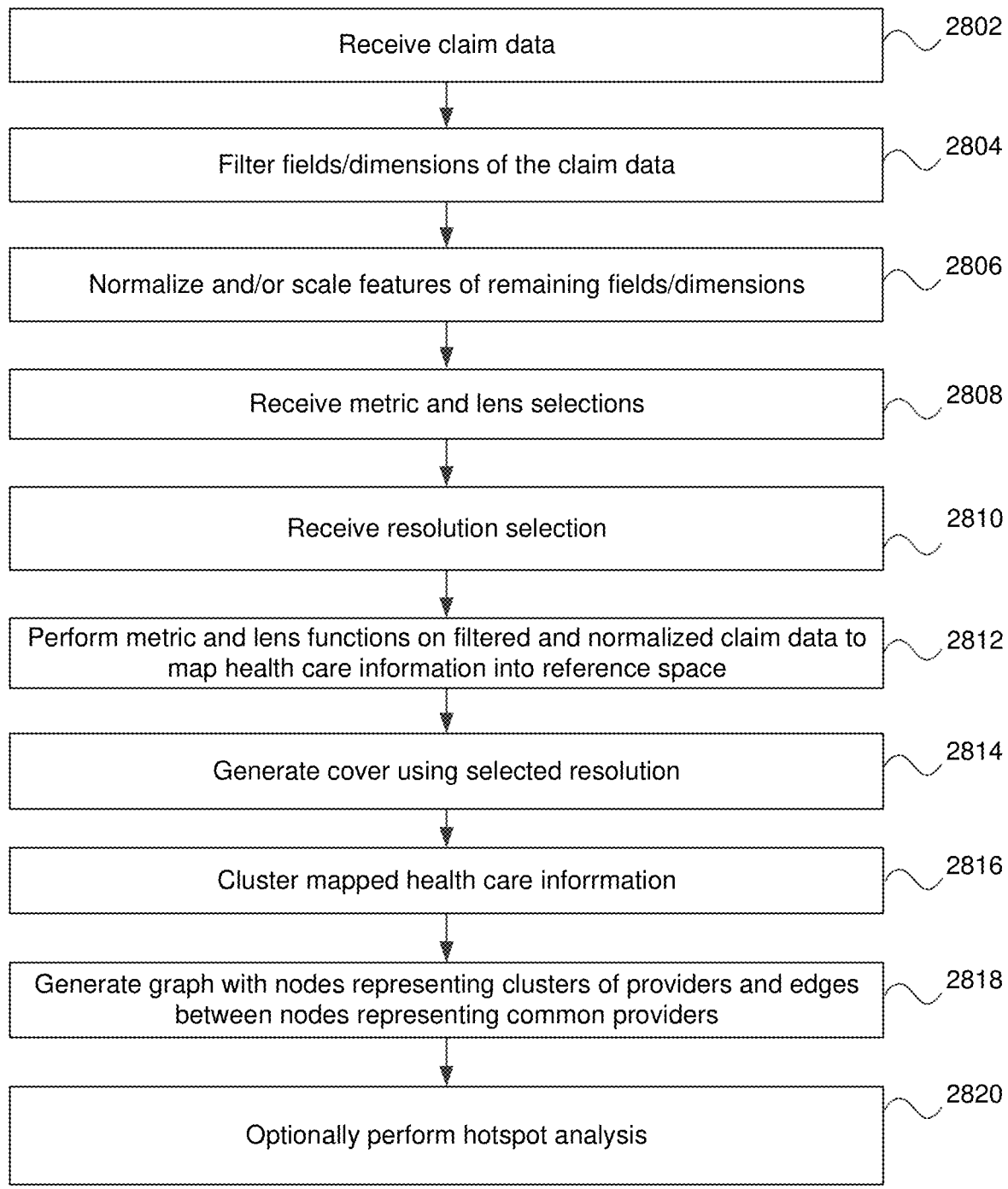
FIG. 28 is a flowchart for identifying patterns in claim denials without querying the original data in some embodiments.

FIG. 28 is a flowchart for identifying patterns in claim denials without querying the original data in some embodiments. In this example, the analysis server 208 may utilize TDA to identify groups of improperly denied claims based on similarity of the multidimensional claims (e.g., across dimensions utilizing distances between dimensions of the claims). In step 2802, the input module 314 receives the claims data including but are not limited to:

Fields from adjudicated claims
Electronic reason codes exchanged in electronic transactions between the health system's claims system and health insurance companies' adjudication systems
Payment adjustment transactions associated with the adjudication history of each claim The claims data may include information regarding whether the claims were denied. In some embodiments, the claims data may include write-offs, refusal, or other information, in various embodiments, the claims data may include reasons (e.g., metadata and/or codes) indicating the reasons for denial.

The claims data may be from any number of payers regarding any number of patients. The claims data may include pre-certification claims and/or claims for services already rendered. The claims data may be characterized as analysis data.

In step 2804, the filter module 316 may select specific fields or dimensions of the claims data and/or remove fields or dimensions of the claims data. In one example, the filter module 316 may select:

| Column Sets |
| --- |
| dx_code_counts |
| hcpcs_code_counts |
| payors |
| prin_dx_code_counts |
| prin_dx_overrep_hcp |
| cs_overrep_medicare |
| providers |
| px_code_counts |
| rev_code_counts |
| combinations of these |

In step 2806, the input module 314 and/or normalization module may normalize any number of the columns and/or scale any number of the columns. The normalized and/or scaled information may replace the original information in the column or, alternately, may be included in a new column added to the data set or may be the basis for new calculations to add new columns to the data set.

The input module 314 and/or normalization module may normalize and/or scale features of at least the first set of health care information. In various embodiments, the normalization module and/or the input module 314 selects one or more features of the data. The normalization module may normalize the data any number of the selected columns and either replace the data or create one or more new columns with the normalized data. In some examples, the normalization module may normalize the data using z scores, term frequency-inverse document frequency (TF-IDF), or in any other method.

In some embodiments, the normalization module may scale the data in the one or more selected columns as discussed herein. The normalization module may either replace the data or create one or more new columns with the scaled data.

Steps 2808-2818 are directed to performing TDA on the data set including the first set of health care information, the second set of health care information, and any additional columns or new information. In various embodiments, the analysis server 208 may perform TDA on selected columns (e.g., a subset of the first set of health care information as well as at least a portion of the second set of health care information).

In step 2808, the analysis server 208 (e.g., the filter module 316) may receive metric and lens selections from a user or another digital device. The metric selection(s) may include any number of metrics from a set of metrics or pseudo-metrics (e.g., does not satisfy the triangle inequality) from a set of metrics. The lens function may project the data into the reference space as discussed herein.

In one example, any number of the following metrics and lens pairs may be received:

| Metrics | Lens Pairs |
|---|---|
| Variance Normalized Euclidean Norm Angle | Gaussian Density & L-Infinity Centrality<br>Metric PCA 1 & Metric PCA 2<br>Neighborhood Lens 1 & Neighborhood Lens 2 |

In step 2810, the analysis server 208 (e.g., the resolution module) receives a resolution selection (e.g., resolution parameters) and possibly gain for analysis. The resolution parameters may be received from users or another digital device. In some embodiments, the resolution module 320 may determine one or more possible resolutions based on one or both sets of health care information. The resolution parameters and gain may be utilized to create a covering in the reference space to assist in clustering and/or for node membership. In one example, a resolution of 30 and a gain of 2.5 may be received.

In step 2812, the analysis server 208 (e.g., the analysis module 320) performs metric and lens functions on the claim data to map the claims to a reference space. The process is further discussed herein regarding TDA. As similarly discussed, in step 2814, the analysis server 208 generates a cover in the reference space using the selected resolution and in step 2816 clusters the mapped health care information. In step 2816, the analysis server 208 clusters the mapped claims data.

In step 2818, the analysis server 208 (e.g., the processing module 212) generates a topological graph using at least some of the metric-lens(es) combinations from the subset of metric-lens combinations and at least one of the resolutions from subset of resolutions. The topological graph may be displayed (i.e., a visualization) or may be generated in memory.

In various embodiments, the denial module 2704 performs hotspot analysis in step 2820. A "hotspot" is a region of the network where the outcome under investigation is more common than would be expected by chance. For example, if 15% of claims are rejected overall, but 50% of claims in a particular group are rejected, then that group is a hotspot for rejections. (i.e., rejections are over-represented in that group).

To locate hotspots in this example, the network (e.g., explained visualization) is coked one of the outcome variables such as, but not limited to:
rej_ind_med_nec
rej_ind_all
dollars_rejected_special
den_ind_med_nec
den_ind_all
dollars_denied_sum If coloring by one of the "ind" outcome variables, the analysis server 208 may set the max value on the color scheme to at least 1.3 and set a reasonable max value (e.g., 10). The user may then look for groups of nodes in the network that are consistently colored, such as red, (or nearly so) and geometrically cohesive.

The claims data represented in the explained visualization 3000 is very feature-rich, so there are many possible comparisons available. In this example, the analysis server 208 may: run a continuous comparison of the payors column set, run a continuous comparison and a categorical comparison on the rejections writeoffs column set, or run a continuous comparison on the dx_code_counts column set.

Some column sets appear more than once because there is more than one statistically valid way to interpret them.

| For these column sets . . . | The analysis server 208 may use this comparison and statistic . . . |
|---|---|
| dx_code_counts<br>hcpcs_code_counts<br>payors<br>prin_dx_code_counts<br>providers<br>rejections_write_offs<br>rev_code_counts<br>dollars<br>timelines<br>bill types<br>payors<br>prin_dx_code_counts<br>providers<br>rejections_writeoffs<br>timelines | continuous<br><br><br><br><br><br><br><br><br>categorical |

For the "code_counts" column sets, the analysis server 208 may be configured to run explains on more than just the most common or most over-represented columns. In that case, the analysis server 208 may create a new column set containing all the "code_counts" of a given type (e.g. all columns with names of the form 67_dx_code_count_*) and a comparison is run on the newly-created column set.

It will be appreciated that, in some embodiments, groupings of nodes enable hotspot analysis and/or hotspot analysis is optional.

Figure 29A:
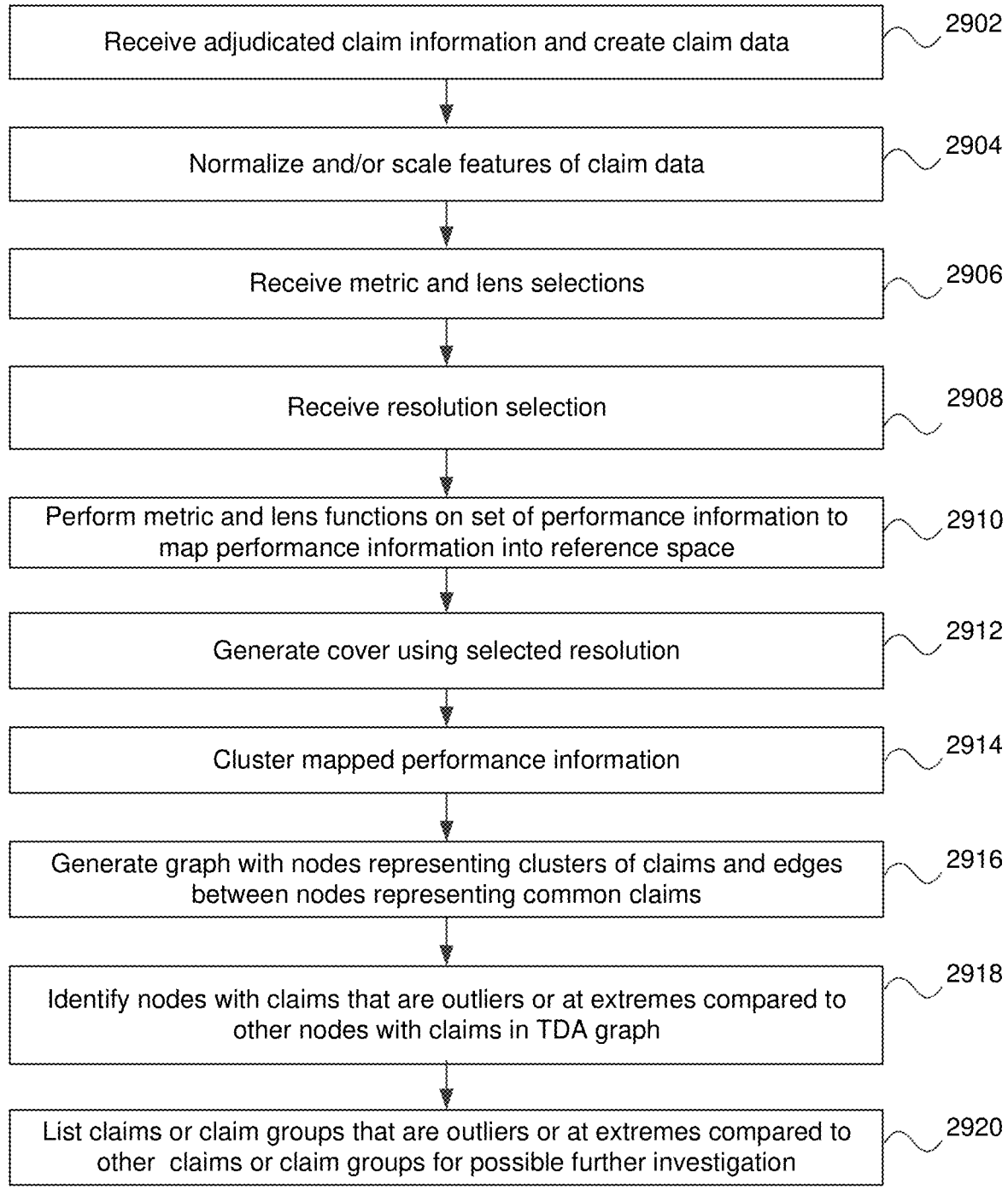
FIG. 29A is a flowchart for identifying groups of improper claim denials and predict whether new claims may be improperly denied based on similarities identified in the groups in various embodiments.

FIG. 29A is a flowchart for identifying groups of improper claim denials and predict whether new claims may be improperly denied based on similarities identified in the groups in various embodiments. Claims may be improperly denied when features or groups of features of a claim are unusual when compared with others. In this example, particular claims or groups of claims may be identified as possible candidates for further investigation if one or more features (e.g., dimensions) are an outlier or an extreme (e.g., dissimilar) to other providers in a TDA graph. As discussed herein, the TDA graph enable for insights to be determined from the shape of data (e.g., without a query to build the TDA graph).

In step 2902, the input module 314 receives adjudicated claim information and generates claim data regarding claims for medical treatment to be performed or that has been performed.

As discussed herein, the input module 314 and/or normalization module may normalize any number of the columns and/or scale any number of the columns. The normalized and/or scaled information may replace the original information in the column or, alternately, may be included in a new column added to the data set or may be the basis for new calculations to add new columns to the data set.

In step 2904, the normalization module (not shown) may normalize and/or scale features of at least the first set of performance information. In various embodiments, the normalization module and/or the input module 314 selects one or more features of the data. The normalization module may normalize the data any number of the selected columns and either replace the data or create one or more new columns with the normalized data. In some examples, the normalization module may normalize the data using z scores, term frequency-inverse document frequency (TF-IDF), or in any other method.

In some embodiments, the normalization module may scale the data in the one or more selected columns as discussed herein. The normalization module may either replace the data or create one or more new columns with the scaled data.

Steps 2906-2916 are directed to performing TDA on the data set including the first set of performance information and any additional columns or new information. In various embodiments, the analysis server 208 may perform TDA on selected columns (e.g., a subset of the first set of performance information).

In step 2906, the analysis server 208 (e.g., the filter module 316) may receive metric and lens selections from a user or another digital device. The metric selection(s) may include any number of metrics from a set of metrics or pseudo-metrics (e.g., does not satisfy the triangle inequality) from a set of metrics. The lens function may project the data into the reference space as discussed herein. In one example, the metric and lens may include Euclidean as a metric and L1-Centrality as a lens. Another lens that may be utilized may be L-Infinity Centrality. It will be appreciated that the filter module 316 may apply any metric or combination of metrics. Similarly, the filter module 316 may apply any lens or combination of lenses.

In step 2908, the analysis server 208 (e.g., the resolution module) receives a resolution selection (e.g., resolution parameters) and possibly gain for analysis. The resolution parameters may be received from users or another digital device. In some embodiments, the resolution module 320 may determine one or more possible resolutions based on the set of performance information. The resolution parameters and gain may be utilized to create a covering in the reference space to assist in clustering and/or for node membership.

In step 2910, the analysis server 208 (e.g., the analysis module 320) performs metric and lens functions on the claim data (e.g., or on the selected columns of the performance information) to map performance information to a reference space. The process is further discussed herein regarding TDA. As similarly discussed, in step 2912, the analysis server 208 generates a cover in the reference space using the selected resolution and in step 2916 clusters the mapped performance information. In step 2914, the analysis server 208 clusters the claim data.

In step 2916, the analysis server 208 (e.g., the processing module 212) generates a TDA graph using at least some of the metric-lens(es) combinations from the subset of metric-lens combinations and at least one of the resolutions from subset of resolutions. The topological graph may be displayed (i.e., a visualization) or may be generated in memory.

In step 2918, the denial module 2704 may identify nodes with claims that are outliers or at extremes compared to other nodes with claims that are members of nodes in the TDA graph. For example, the denial module 2704 may apply L1 for a feature of a particular entity against that feature of other entities to generate a score. The denial module 2704 may perform this calculation for any number of features of any number of claims. The value of the score (e.g., the largest scores above a predetermined threshold or top largest scores) of any feature or combination of features may indicate entities that may be further assessed, analyzed, or investigated. The denial module 2704 may identify those entities with high entity scores and/or high feature scores as well as those entities that share membership in a node with entities with high entity scores and/or high feature scores.

In some embodiments, the analysis module 320 and/or the GUI engine 322 may identify those entities with the highest L1 extremities score (e.g., an entity score or feature score of any number of features of the entity), based on position in the TDA graph which the least density of other nodes, lack of links with other nodes, lack of membership of a node with other providers (e.g., no other members of the nodes or other members being below a threshold), or the like. Similarly, the analysis module 320, GUI engine 322, or denial module 2704 may identify claims that share node membership with claims (e.g., claims known to be improperly denied) with the highest L1 extremities score.

In another example, using the members (i.e., entities or data points of entities), the entities may be sorted by a measure of centrality (e.g., L1-Centrality) generated on the dataset. The contribution of each feature may be computed to the computed measure of centrality. For instance, a script may calculate a Euclidean distance matrix by each feature, squared, and then sum up the distances to determine the L1-Centrality lens value for each feature.

A measure of centrality lens values and a subset containing the largest lens values for each feature along with their features names may be written into a comma separated file. As an example, a script may write a file that contains eleven columns for each row, including the L1-Centrality lens value, top five contributing feature names and their values in alternating order.

For validation of the ranking, the file may be appended to the original source data file. Ranking may be evaluated based on, for example, whether the ranking reflects a good weighting of the features. In the health care example of FIG. 20, a good weighting may be assessed based on knowledge about the healthcare system, medical billing, medical coding, reimbursement, coverage and/or clinical workflow for some examples. In the example of FIG. 29A, a good weighting may be assessed on knowledge about the resources and network utilized, expected performance, reasons for denial, metadata, and/or the like.

If it is not a good weighting, the dataset may need to be re-transformed, uploaded and/or analyzed in networks (e.g., one or more network(s) of nodes). For example, a transformation may re-scale the variables to reflect that some variables are more important. For instance, paid per claim and total paid may have a higher upper bound than other variables. So if all variables are re-scaled to be between zero and one, paid per claim and total paid may be re-scaled to be between zero and two. Sometimes more networks may be re-created to find a better localization or to pull out dense networks regions. Other times other previously created networks may be revisited and colored by other (e.g., combinations of) features.

If the ranking is considered good enough such that it provides a good description of behavior warranting investigation, the reporting module 1906 may generate a ranked list of claims. The ranked list of claims or groups of claims may be the subject of an investigation or analysis team for confirmation, verification, and/or further investigation. The investigations or analysis team may audit electronic medical records of a provider. Any information as to whether the group or claim need to be rectified may be recorded and/or provided to an analyst or investigator. This information may be used to improve the ranking, such as creating new features or adjusting the weights of features that contribute to the ranking.

In various embodiments, the denial module 2704 may utilize L1 Eccentricity or L-infinity Eccentricity to measure a feature of each particular entity against the other entities. The resulting measure may indicate features and/or entities that are outliers or extremes (e.g., based on any number of outlying or extreme features). A reporting module (not depicted) may list a predetermined number of claims or groups in order of the size of value from the resulting utilization of L1 function. In some embodiments, the reporting module may further identify those functions that have the greatest value from the resulting utilization of L1 function(s) of those claims.

In step 2920, the reporting module generates a report identifying claims for further review.

Figure 29B:
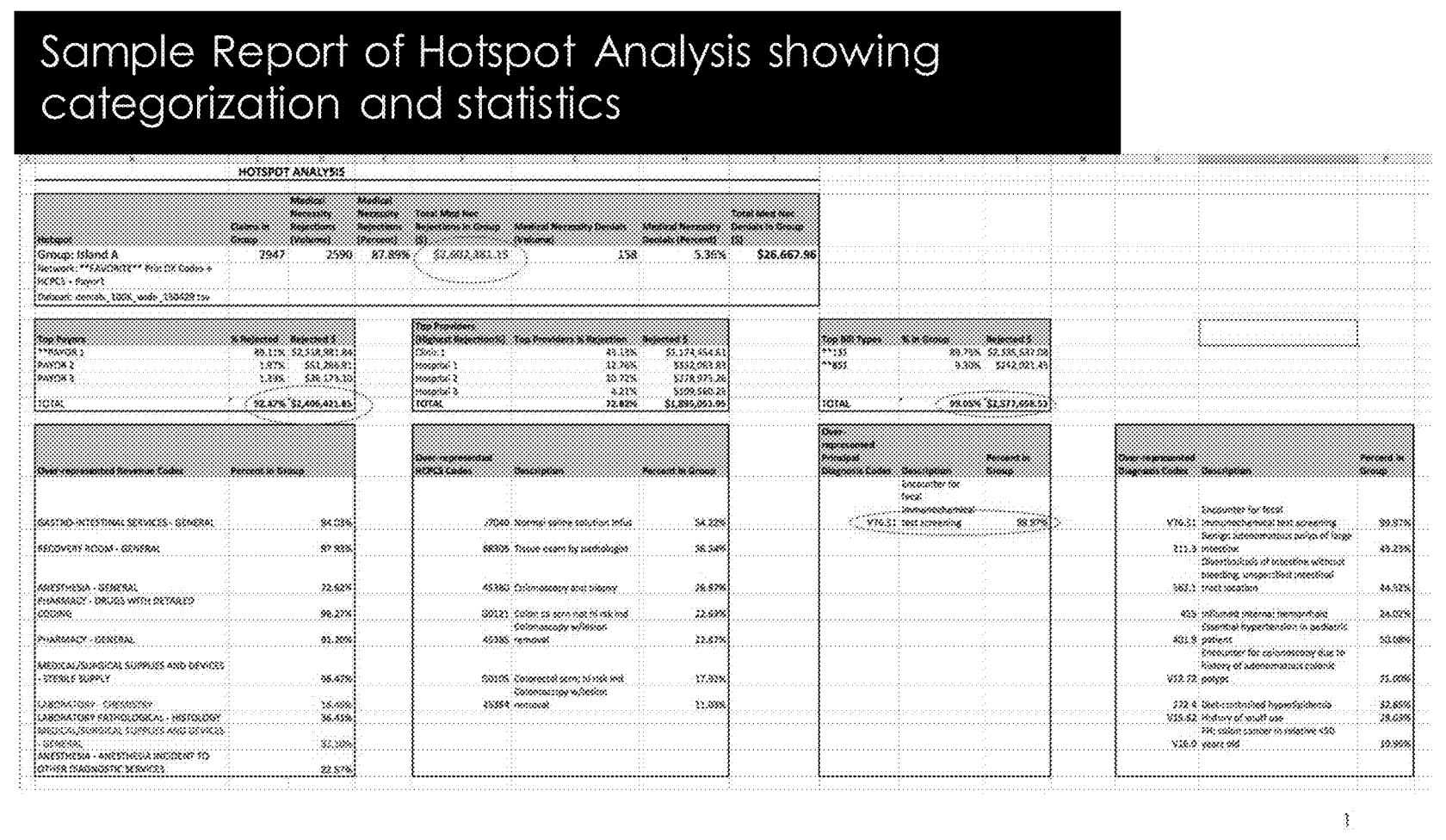

FIG. 29B depicts an example report of hotspot analysis showing categorization and statistics to further review hotspots or groups. The hotspot or group may include nodes with the claims that are known or suspected of being improperly denied. In the sample report, a hotspot or group is analyzed and includes summary statistics at the top, identifies top payors, top providers, top bill types, over-represented revenue codes, over-represented HCPCS codes, over-represented principal diagnosis codes, and over-represented diagnosis codes. The circled information indicates information that is particularly significant when compared to other hotspots, groups, or the claim data in general (e.g., based on centrality as discussed herein). In this example, the total medical necessity rejections in the group is $2,602,381.15, the top payors rejected 92.47% of the claims, the two top bill types rejected 99.05% of the amount, and test screening was the most over-represented diagnosis code.

These features may allow future claims adjudication information to be assessed for possible improper denials. For example, the prediction module 2710 may track features such as those identified in the example report. When a new adjudicated claim is received, the prediction module 2710 may compare features (e.g., attributes and dimensions) of the claim to groups or hotspots of claims known to be improperly dismissed. If the new claim is sufficient similar in comparison to the features (e.g., by a predetermined percentage, above a threshold, and/or the like), then the adjudicated claim may be flagged for further review. As a result, the coding or other features of the claim in question can be assessed for errors and for corrections.

Figure 30:
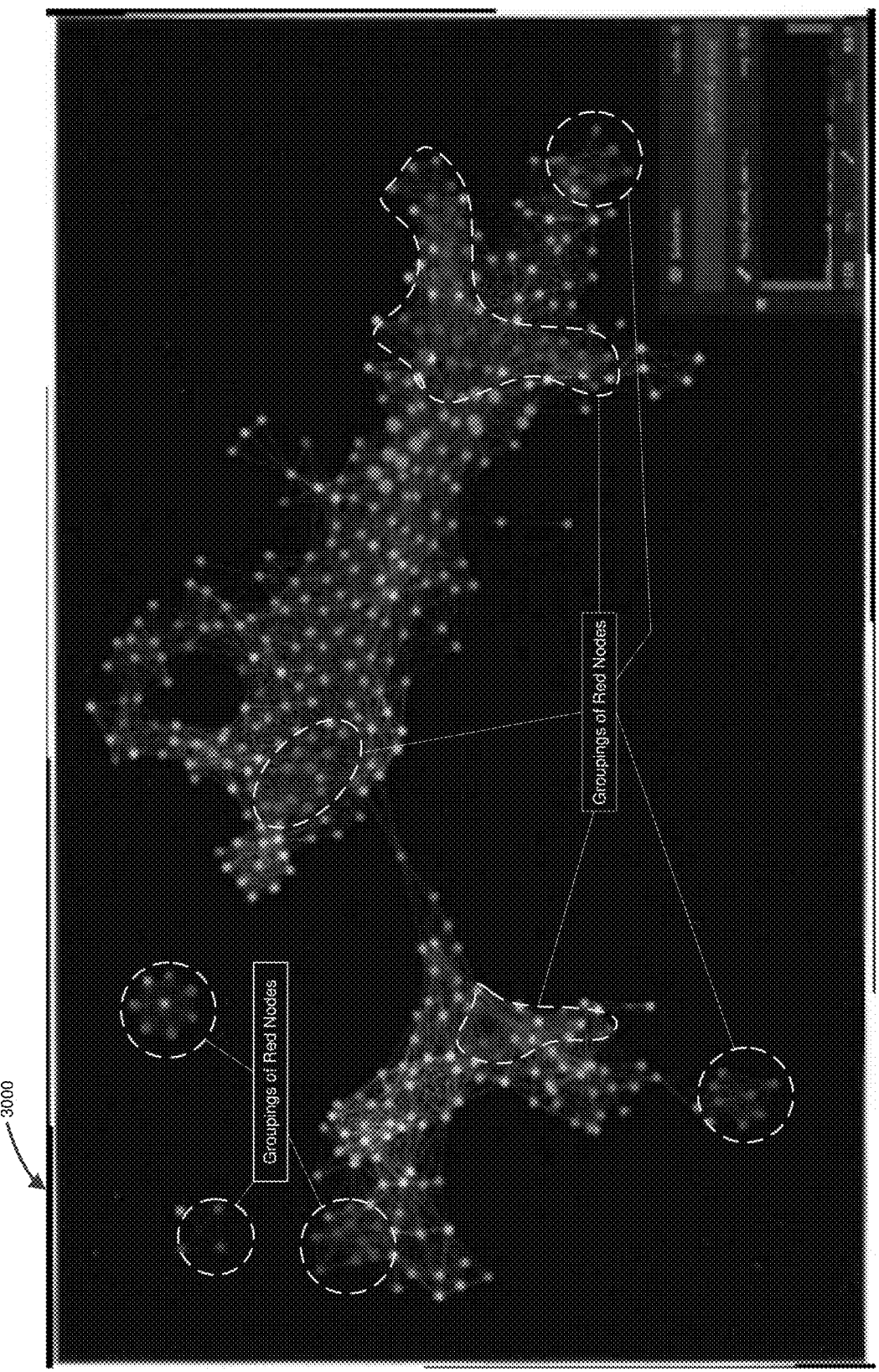
FIG. 30 is an example of an explanation visualization generated by applying query-less TDA (the initial application of TDA on a data set is always without generating or applying queries on the data itself) on claim data to identify relationships within claim adjudications to provide insights on claim denials in some embodiments.

FIG. 30 is an example of an explanation visualization 3000 generated by applying query-less TDA (the initial application of TDA on a data set is always without generating or applying queries on the data itself) on claim data to identify relationships within claim adjudications to provide insights on claim denials in some embodiments. In the explanation visualization 3000 depicts a so-called "topological summary" of the claims data.

In some embodiments, the explanation visualization 3000 is a map all claims of the claim data, based on a notion of similarity (e.g., utilizing the metric and lenses to determine distances between features of the claim and define similarity using the cover in the reference space). Claims that are close together in this explanation visualization 3000 are relatively similar, while claims that are far apart in the explanation visualization 3000 are relatively different from each other. In this example, a concentration of Medicare claims may be in one location of the explanation visualization 3000 while private payer claims may be in a separate location. In another example, the explanation visualization 3000 may depict claims for outpatient tests in a first location, with claims for inpatient surgeries in a second location that is separate and apart from the first location.

It will be appreciated that the GCUI module 2710 may color the explanation visualization 3000 by a number of features that are present in the data, similarity, and/or outcome (e.g., denial, reasons for denial, and/or meta data associated with the claim data that may have not been a part of the TDA analysis).

In this example, the explanation visualization 3000 was generated based on adjudicated claims including claims that were allowed and that that were denied. In various embodiments, a user may utilize the GCUI module 2710 to provide commands to color different nodes based on claim outcome (e.g., thereby coloring claims that are denied with a similar color). In one example, red may indicate regions where denied claims are over-represented in those groups of claims. In this example, a hotspot or a group of claims that have a high percentage of denials are extremely similar to teach other. There are multiple groups of hotspots through this explanation visualization 3000 (e.g., through this similarity map).

The GCUI module 2710 may provide tools to identify drivers of denials by enabling a user to look into each hotspot to discover drivers of denials. In various embodiments, the GCUI module 2710 may provide a more nuanced view than just looking for global trends across the whole dataset, and a more comprehensive view than just evaluating each claim individually. It would be extremely difficult using traditional methods to identify the key drivers for denials across 11,000 input variables (e.g., 11,000 features or dimensions) per claim.

Regarding these hotspots, a user may be interested in:
What are characteristics of each hotspot? That is, what's making this a coherent group of claims that's similar to each other, but different from the rest of the network? and
Within each of these coherent groups of claims, what's driving denials?

The GCUI module 2710 may provide mechanisms for answering these questions which may, in some embodiments, exposes these hotspots of denials for those seeking to identify and understand systematic denial patterns. Let us jump to that user interface for understanding hotspots.

Figure 31:
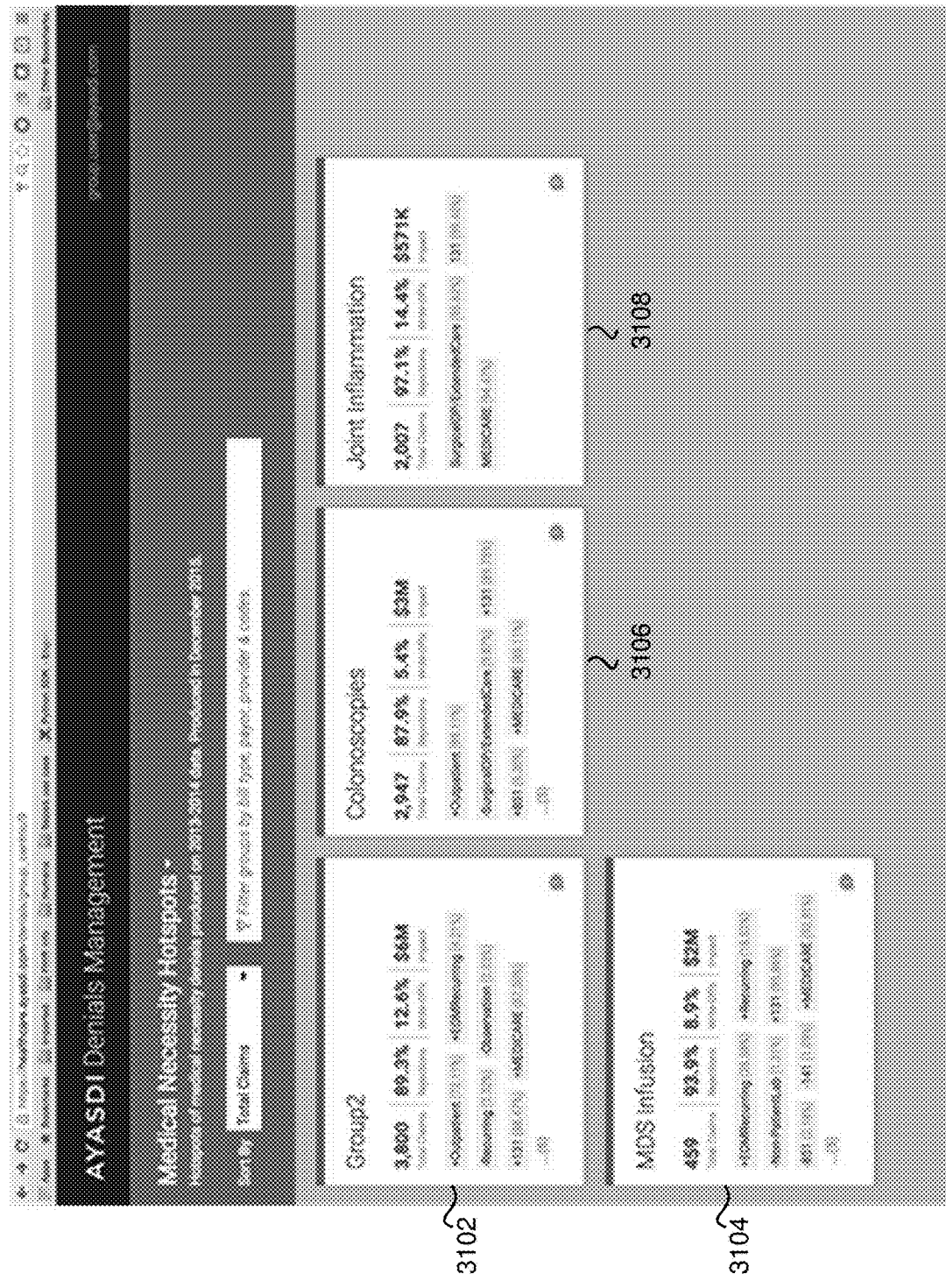
FIG. 31 is a denials application user interface in some embodiments.

FIG. 31 is a denials application user interface in some embodiments. In various embodiments, the GCUI module 2710 enables a user to log into the system (e.g., with a username, password, and possibly encryption keys to preserve personal medical information). The denials application user interface may provide a collapsed view of each of the groups in the explanation visualization 3000.

In various embodiments, after logging in, the GCUI module 2710 generates the denials application user interface. The user may select the explanation visualization 3000 and input a selection to color the nodes of the explanation visualization 3000 based on claim denials. The explanation visualization 3000 may utilize any color and any different color to color the nodes of the explanation visualization 3000 based on denial. One example is depicted in FIG. 30.

The denials application user interface may then depict a collapsed view of each group of denials (e.g., the denials hotspots depicted in red in the denials application user interface). In the denials application user interface depicted in FIG. 31, the interface depicts groups of claims that have a higher than average percentage of medical necessity rejections. Each card 3102-2108 has basic information about each group (e.g., card 3102 describes Group2, card 3104 describes MDS Infusion, card 3106 describes Colonoscopies, and card 3108 describes Joint Inflammation). Information described in one or more cards may include the total number of claims in the group, the percent of rejections in the group, the dollar impact of the group, and the top payers of the group, facilities of the group, bill types of the groups, and account classes of the group.

In various embodiments, after the TDA graph is generated as described herein (the graph may be the same as the explanation visualization except not visualized or depicted). The user may color the nodes based on denials as described herein to depict groupings of nodes of similar color (i.e., by similarity of criteria which, in this case, includes denials). Recall that in the TDA graph, proximity of nodes in the graph may also depict a degree of similarity while distances may depict a degree of dissimilarity.

In some embodiments, the user may view an explanation visualization 3000 and select groupings of nodes by colors. In various embodiments, the GCUI module 2710 may group nodes that have similar criteria (e.g., similar color) within a predefined distance of each other or nodes that are linked together (i.e., nodes that are linked together by an edge or line share at least one record or row of data from the original claim data—recall that each node in the explanation visualization 3000 contains one or more records or rows of data from the original claim data as members).

In some embodiments, the analysis server 208 autogroups the nodes based on the selected criteria (e.g., based on denials). Autogrouping is discussed with regard to FIG. 20-25. Each group of the selected partition may be depicted by a card in the denials application user interface. For example, the analysis server 208 may generate the total number of claims in the group (e.g., total number of rows for each node that is a member of the group), the percent of rejections in the group, the dollar impact of the group, and the top payers of the group, facilities of the group, bill types of the groups, and/or account classes of the group. These are examples. It will be appreciated that any number of group statistics may be generated. In various embodiments, each group may contain similar measures (not measurements).

In one example of card 3102 regarding group 2, the analysis server 208 determined the total number of claims for the group (3,800), the percentage rejections (89.3%), the percent of write-offs for the group relative to revenue (12.6%), impact ($6 m), as well as percent outpatient (72.11%), EOMRecurring (4.21%), recurring (2.32%), observation (2.03%), 131 (a code) 88.47%), and Medicare (87.50%). The card indicates that there are six more statistics that are not displayed on this particular collapsed card.

This can depict a descriptive claim profile. It will be appreciated that the number and type of statistical assessments may be selected by a user from a list of possible available statistics to depict on each card. For example, the user may have input into the denials application user interface a selection of statistics to generate and depict in a card, including, but not limited to total number of claims for the group, the percentage rejections, the percent of write-offs for the group relative to revenue, impact, as well as percent outpatient, EOMRecurring, recurring, observation, 131 (codes), and Medicare.

In viewing these cards, an analyst may choose to begin assessment starting with the card/group that has highest revenue impact or largest percent of denials.

In various embodiments, the GCUI module 2710 enables the denials application user interface to allow users to enter notes regarding each card (e.g., concerning the group of that particular card). The GCUI module 2710 may also enable tracking to determine the number of users that have accessed or otherwise seen the card. For example, in card 3102, the GCUI module 2710 depicts a number in a lower right corner of the card 3102 to indicate that this number of other users (e.g., each with a different username or other identifier) that have already looked at this group.

Figure 32:
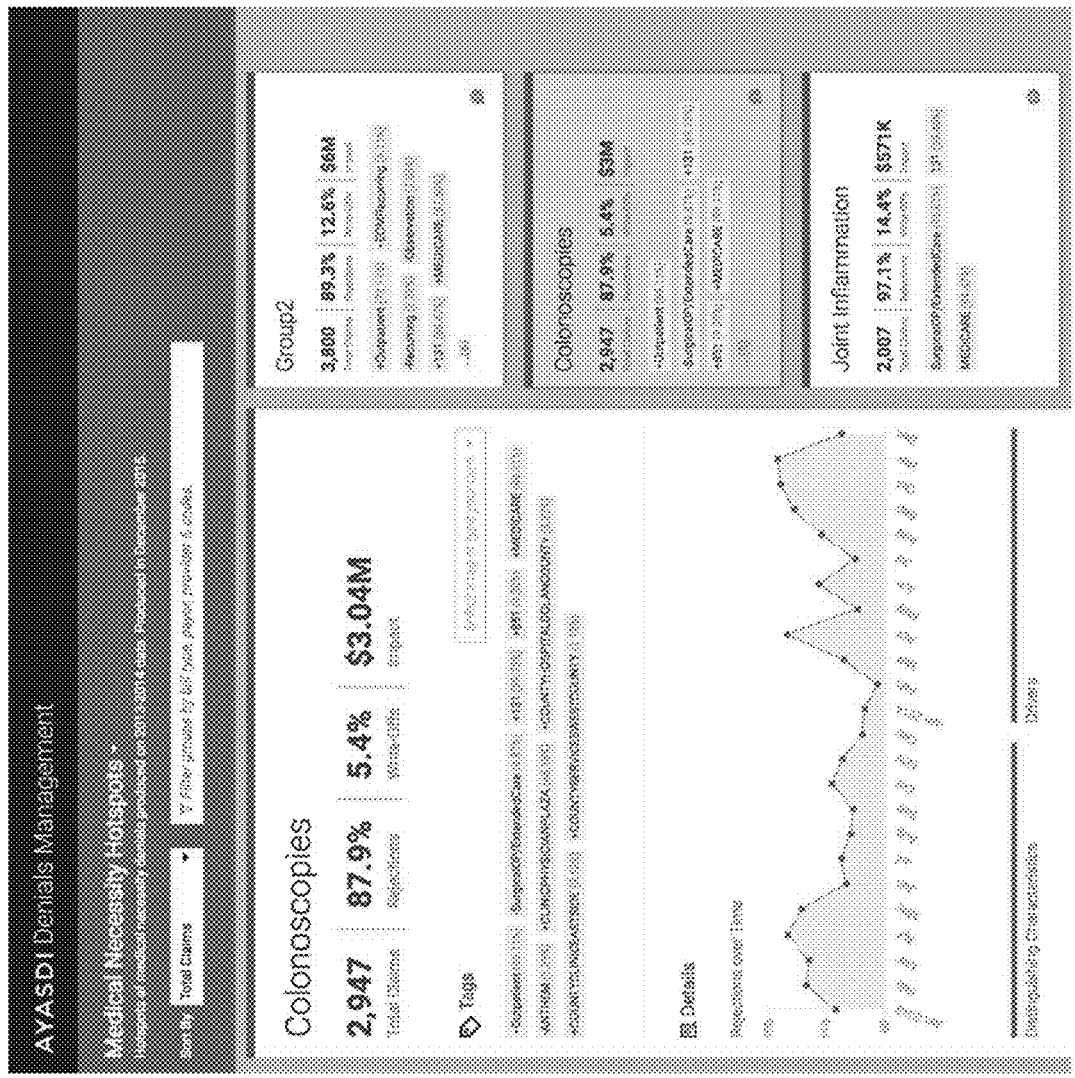
FIG. 32 depicts expanded card for colonoscopies in the denials application user interface after a user may interact with the collapsed card (depicted in FIG. 31) in some embodiments.

FIG. 32 depicts expanded card for colonoscopies in the denials application user interface after a user may interact with the collapsed card 3106 (depicted in FIG. 31) in some embodiments.

By engaging (e.g., clicking) on card 3106 as depicted in FIG. 31, the GCUI module 2710 causes the card to expand. In various embodiments, the remaining cards stack up on the side of the denials application user interface (e.g., please see the other, unselected collapsed cards moved to the right of the window in the denials application user interface in FIG. 32).

In the expanded card, there is more information regarding this group. In various embodiments, the same summary statistics of this group of claims remains at the top of the expanded card. Just below the summary are a set of tags that provide additional statistics on the group of claims: The top payers, the top facilities, bill types etc. present in this hotspot of claims. Further below, the Rejections Over Time trendline provides a quick visual cue of whether or not denials in this group are still an ongoing problem. In this case, there is no reason to believe this issue is going away. In various embodiments, the user may select from the denials application user interface a selection of statistics to generate and depict in the expanded card. In some embodiments, the denials application user interface enables the user to select statistics to generate and choose where those statistics should be depicted (e.g., in the collapsed or expanded card). In some embodiments, the denials application user interface enables the user to change statistics to be generated, or move statistics between views (e.g., from the collapsed view of the card to the expanded view, from the expanded view to the collapsed view, or on both the collapsed view and the expanded view).

It will be appreciated that a user may not be limited to statistical measures, but the user may select one or more function graphs to be depicted in the expanded view. In the example in FIG. 31, the graph depicts rejections over a timeline.

Below the graph, the denials application user interface depicts group insights. The Distinguishing Characteristics on the left describes the profile of the claims in this group in contrast to the rest of the data. These characteristics are categorized by revenue codes, HCPCs codes, and the like with each category revealing the overrepresented factor within each category.

There may be a longer list of drivers on the right of the denials application user interface which may suggest actions to take based on drivers of rejections within this group. These drivers may be ascertained by looking at rejected claims in comparison with accepted claims within the hotspot of similar claims.

Figure 33:
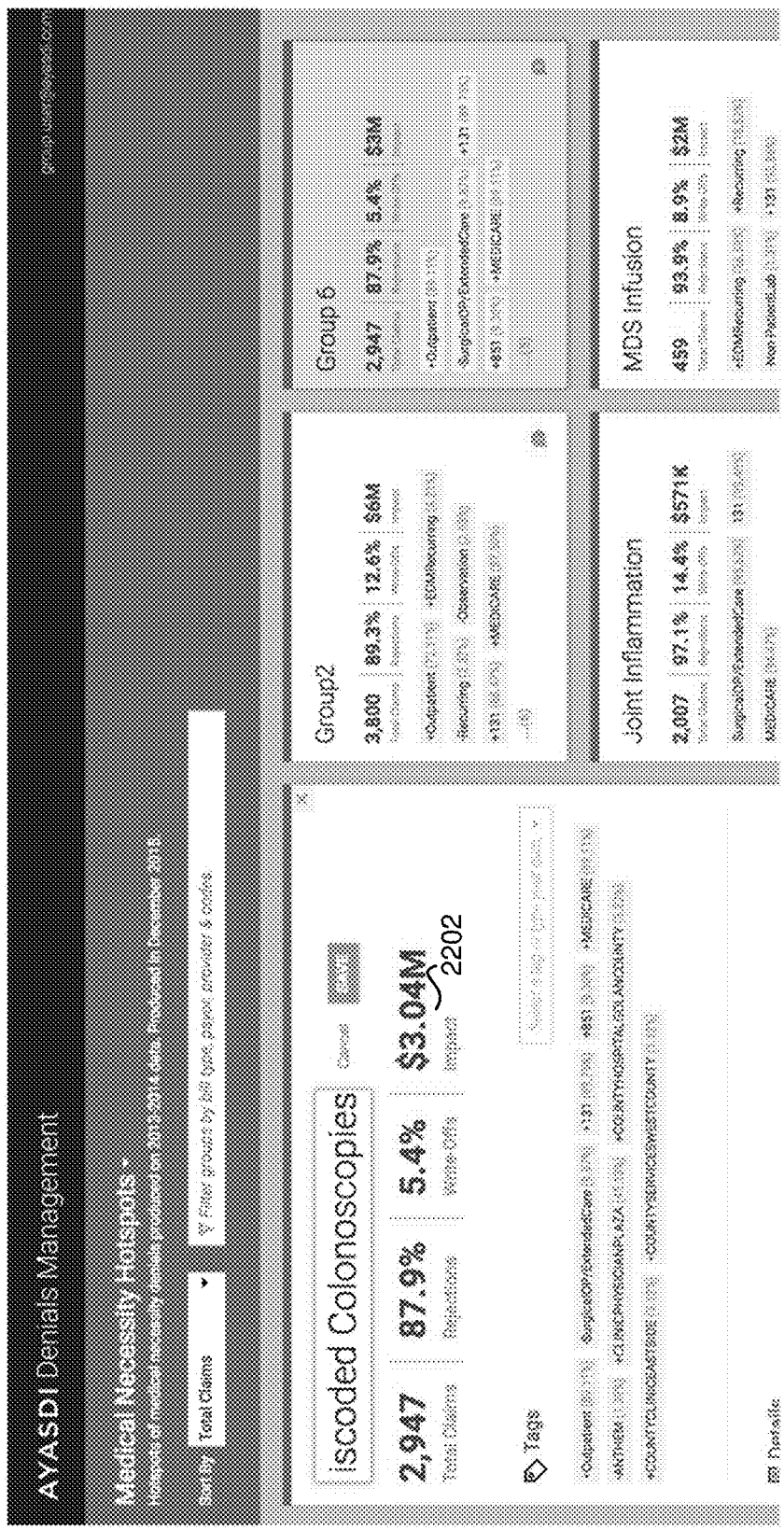
FIG. 33 depicts another view of the expanded card for colonoscopies in the denials application user interface after a user may interact with the collapsed card (depicted in FIG. 31) in some embodiments.

FIG. 33 depicts another view of the expanded card for colonoscopies in the denials application user interface after a user may interact with the collapsed card 3106 (depicted in FIG. 31) in some embodiments. In this example, the denials application user interface enables the user to edit the card (e.g., rename the group).

On the left hand side, the denials application user interface depicts a number of HCPCS codes. After assessing the statistical measures in the card, the interventions in this group seem to be consistent with a colonoscopy including tissue sampling and investigation. The denials application user interface depicts drivers of acceptance on the right. If the user engages with icons (e.g., the "+" signs) against drivers of acceptance, the denials application user interface depicts HCPCS and Diagnosis codes corresponding to inflamed tissue. Whereas, looking at the drivers of rejection, the denials application user interface depicts non-specific diagnosis and HCPCS codes around more chronic conditions.

In this example, this claim profile suggests a coding issue and the rejected claims could use a more specific diagnosis to justify the additional tissue examination beyond routine screening instead of the more generic diagnoses of chronic issues. Once the user has studied the group's characteristics and understood the key issues driving rejections in this group, the user can proceed to action these insights In this example, the name of the group has been edited to "Miscoded Colonoscopies."

The expanded card may be scrolled to the bottom in the denials application user interface.

Figure 34:
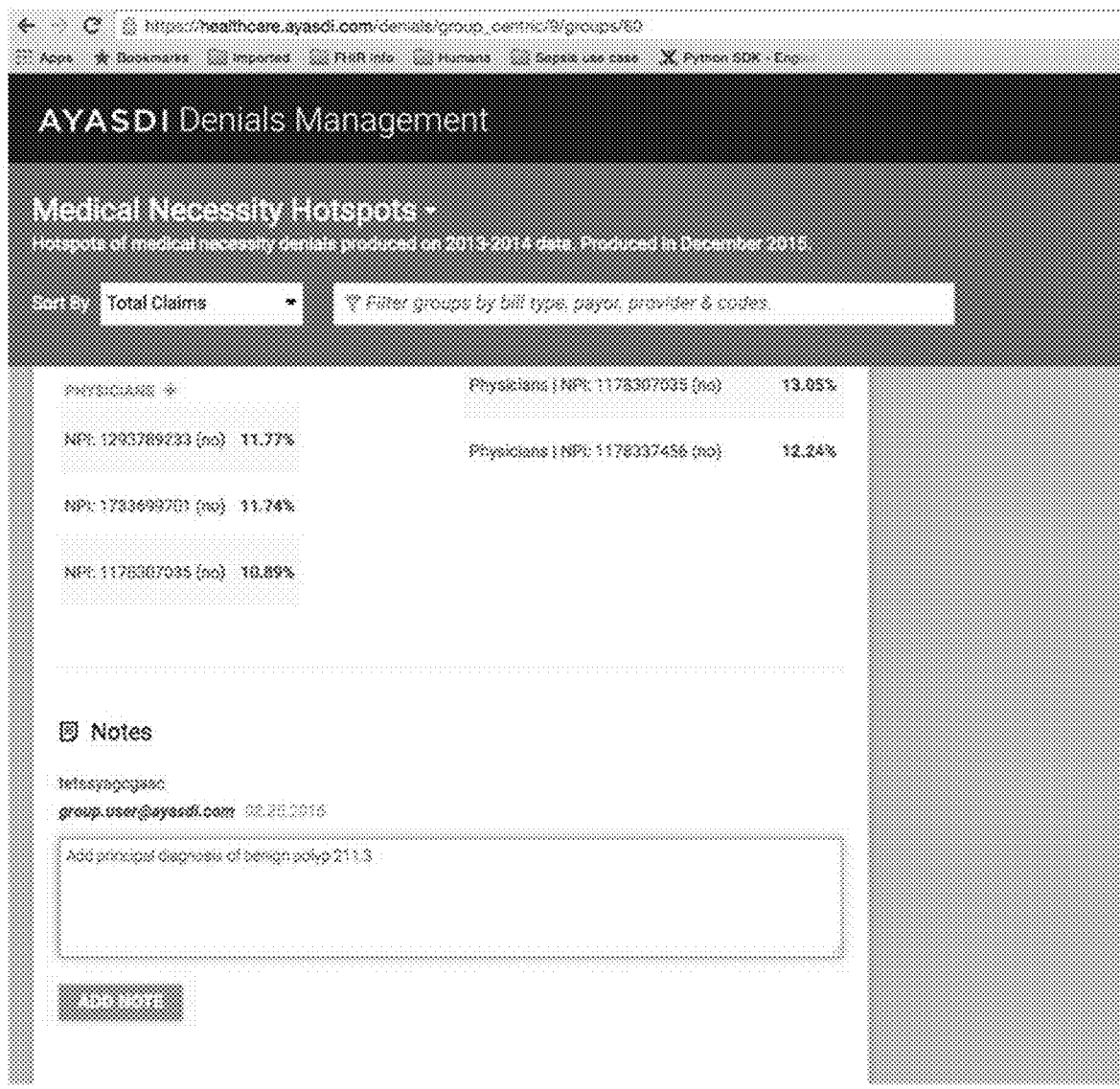
FIG. 34 depicts the bottom of the expanded card for colonoscopies in the denials application user interface after a user may interact with the collapsed card (depicted in FIG. 31) in some embodiments.

FIG. 34 depicts the bottom of the expanded card for colonoscopies in the denials application user interface after a user may interact with the collapsed card 3106 (depicted in FIG. 31) in some embodiments.

In some embodiments, the denials application user interface enables users to leave one or more notes associated with one or more cards. The note may be saved and is accessible through the denials application user interface (e.g., through another user on a different machine on a shared network). In one example, analysts can leave comments and share insights regarding each group via each card through the denials application user interface. Here, the user can enter a note. In one example, the user may describe a problem and suggest that for rejected claims in this group, the principal diagnosis should be set to "suspected polyp." This information can be passed to the customer's denials management system to be consumed in denials work queues.

Now that the group is understood, the user may review other groups with an essential hypertension diagnosis to see if a similar solution would work for them. In one example, the user may enter "Hypertension" in the search bar at the top of the denials application user interface.

All groups and their related cards (e.g., collapsed) that also have Essential Hypertension as part of the diagnosis codes may be depicted. In this example, the joint inflammation group may be depicted.

Figure 35:
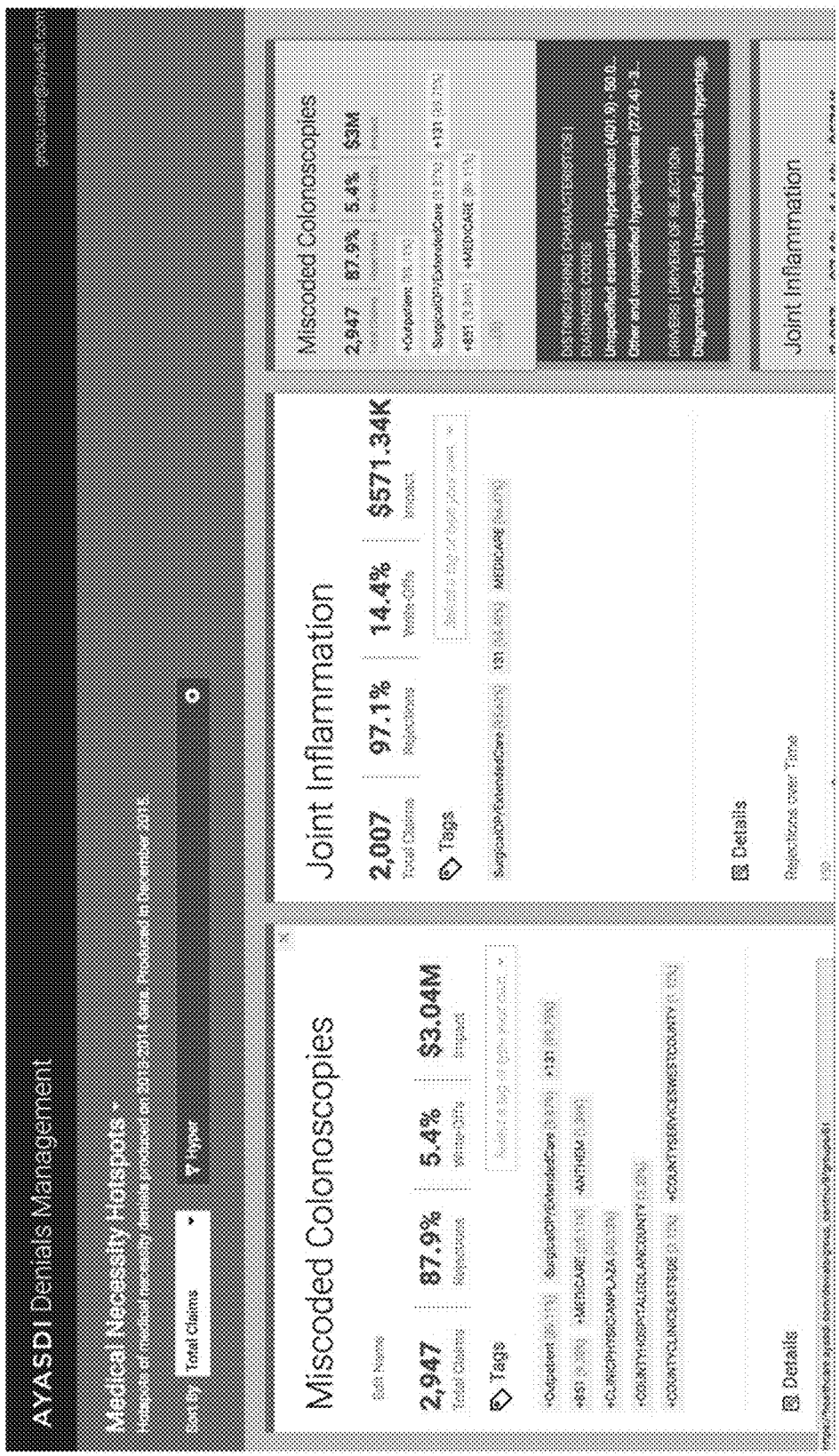
FIG. 35 depicts the denials application user interface after the user input "Essential Hypertension" in the search bar of the denials application user interface in some embodiments.

FIG. 35 depicts the denials application user interface after the user input "Essential Hypertension" in the search bar of the denials application user interface in some embodiments. In this example, the denials application user interface depicts a collapsed card for the group of "Miscoded Colonoscopies" and a group a collapsed card for the group of "Joint Inflammation."

This allows the user to compare groups side by side and determine if two groups of claims may have similar rejection patterns and can be disposed of similarly.

Figure 36:
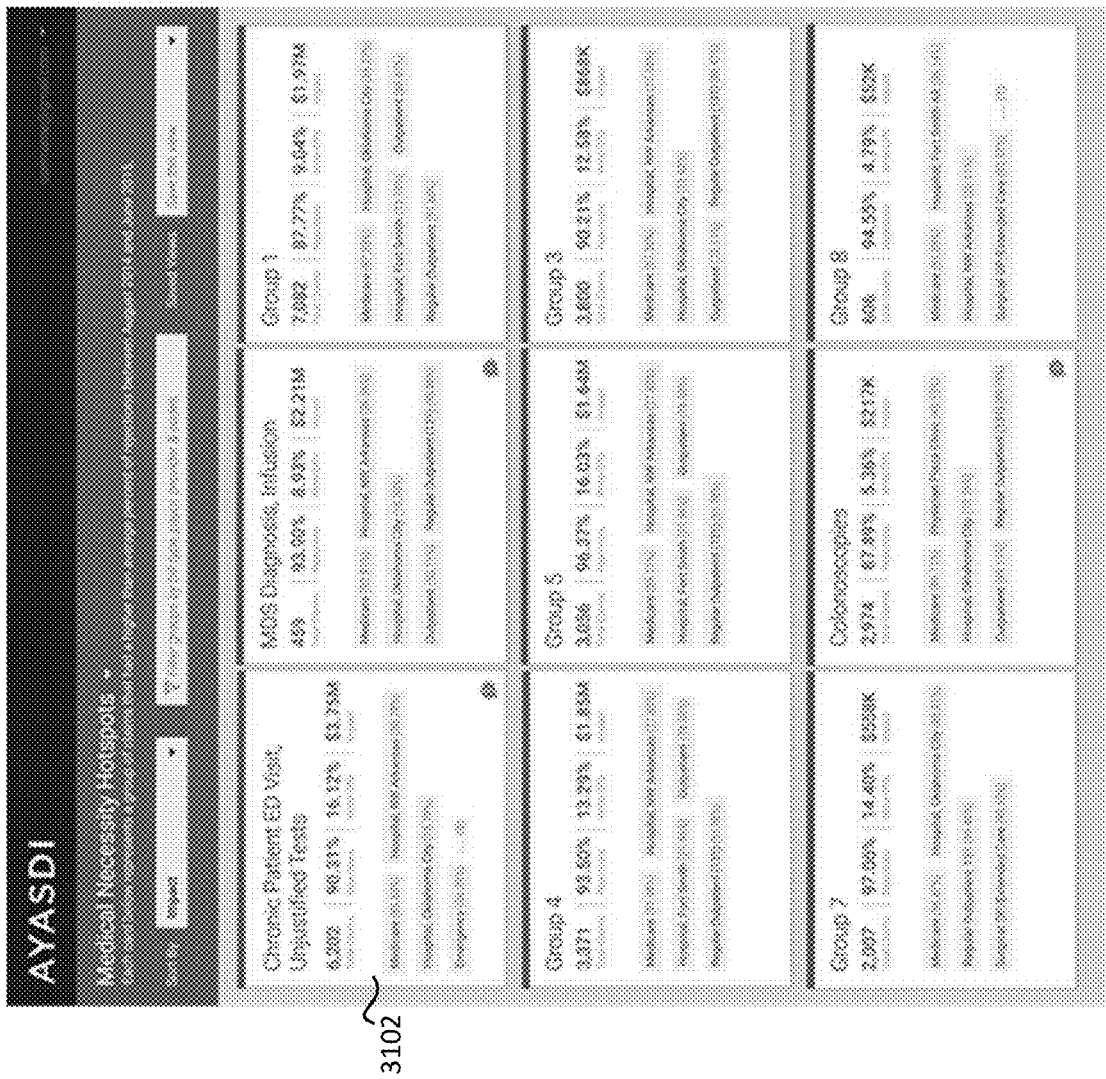
FIG. 36 is another denials application user interface in some embodiments.

FIG. 36 is another denials application user interface in some embodiments. In various embodiments, the GCUI module 2708 enables a user to log into the system (e.g., with a username, password, and possibly encryption keys to preserve personal medical information). The denials application user interface may provide a collapsed view of each of the groups (e.g., collapsed cards) of the explanation visualization 3000.

As discussed herein, after logging in, the GCUI module 2708 generates the denials application user interface. The user may select the explanation visualization 3000 and input a selection to color the nodes of the explanation visualization 3000 based on claim denials. The explanation visualization 3000 may utilize any color and any different color to color the nodes of the explanation visualization 3000 based on denial. One example is depicted in FIG. 30.

The denials application user interface may then depict a collapsed view of each group of denials (e.g., the denials hotspots depicted in red in the denials application user interface). In the denials application user interface depicted in FIG. 36, the interface depicts groups of claims that have a higher than average percentage of medical necessity rejections. In this example, cards include Chronic Patient ED Visit (Unjustified Tests), MDS Diagnosis (Infusion), Group 1, Group 4, Group 5, Group 3, Group 7, Colonoscopies, and Group 8. There may be any number of other collapsed cards associated with any number of groups.

Information described in one or more cards may include the total number of claims in the group, the percent of rejections in the group, write-offs, impact, the dollar impact of the group, and the top payers of the group, facilities of the group, bill types of the groups, and account classes of the group.

In various embodiments, after the TDA graph is generated as described herein (the graph may be the same as the explanation visualization except not visualized or depicted). The user may color the nodes based on denials as described herein to depict groupings of nodes of similar color (i.e., by similarity of criteria which, in this case, includes denials). Recall that in the TDA graph, proximity of nodes in the graph may also depict a degree of similarity while distances may depict a degree of dissimilarity.

In some embodiments, the user may view an explanation visualization 3000 and select groupings of nodes by colors. In various embodiments, the GCUI module 2708 may group nodes that have similar criteria (e.g., similar color) within a predefined distance of each other or nodes that are linked together (i.e., nodes that are linked together by an edge or line share at least one record or row of data from the original claim data—recall that each node in the explanation visualization 3000 contains one or more records or rows of data from the original claim data as members).

In some embodiments, the analysis server 208 autogroups the nodes based on the selected criteria (e.g., based on denials). Autogrouping is discussed with regard to FIG. 20-25. Each group of the selected partition may be depicted by a card in the denials application user interface. For example, the analysis server 208 may generate the total number of claims in the group (e.g., total number of rows for each node that is a member of the group), the percent of rejections in the group, the dollar impact of the group, and the top payers of the group, facilities of the group, bill types of the groups, and/or account classes of the group. It will be appreciated that any number of group statistics may be generated. In various embodiments, each group may contain similar measures (not measurements).

In one example of card 3602 regarding the group for "Chronic Patient ED Visit (Unjustified Tests)," the analysis server 208 determined the total number of claims for the group (6,202), the percentage rejections (90.3%), the percent of write-offs for the group relative to revenue (16.12%), impact ($3.75 m), as well as Medicare (85.63%), Hospital, NW Arkansas (30.78%) Hospital, Oklahoma City (15.79%), Emergency (36.29%). The card indicates that there are five more statistics that are not displayed on this particular collapsed card. The Medicare statistic may indicate the number of records of patients or the number of patients associated with the records of the claim data that are on Medicare. The different hospitals suggests that the group includes treatment performed at different hospitals, and that the hospital in NW Arkansas treated/pre-certified 30.78% of all patients in this particular group.

This can depict a descriptive claim profile. It will be appreciated that the number and type of statistical assessments may be selected by a user from a list of possible available statistics to depict on each card. For example, the user may have input into the denials application user interface a selection of statistics to generate and depict in a card.

In viewing these cards, an analyst may choose to begin assessment starting with the card/group that has highest revenue impact or largest percent of denials.

In various embodiments, the GCUI module 2708 enables the denials application user interface to allow users to enter notes regarding each card (e.g., concerning the group of that particular card). The GCUI module 2708 may also enable tracking to determine the number of users that have accessed or otherwise seen the card. For example, in card 3602, the GCUI module 2708 depicts a number in a lower right corner of the card 3602 to indicate that this number of other users (e.g., each with a different username or other identifier) that have already looked at this group.

In various embodiments, the title of the card may be changed or entered. For example, a subject matter expert may enter or change the name of a card. The GCUI module 2708 may display top statistics for a group in the denials application user interface for identifying important diversifying information for the group. The GCUI module 2708 may, in some embodiments, sort groups (e.g., collapsed cards) in the denials application user interface. In one example, example, the GCUI module 2708 sorts groups by highest impact. In some embodiments, the GCUI module 2708 sorts by any number of criteria, including, for example, total claims, rejections, and write-offs.

In some embodiments, the icon in the lower right of the denials application user interface may indicate the number of annotations (e.g., notes) made by one or more users. These notes or annotations may be saved with the denials application user interface and the card in particular. Other users may choose to view the annotations, or block views of annotations. In some embodiments, a user may block a set of other users but not all (e.g., particularly when working with specific team).

Figure 37:
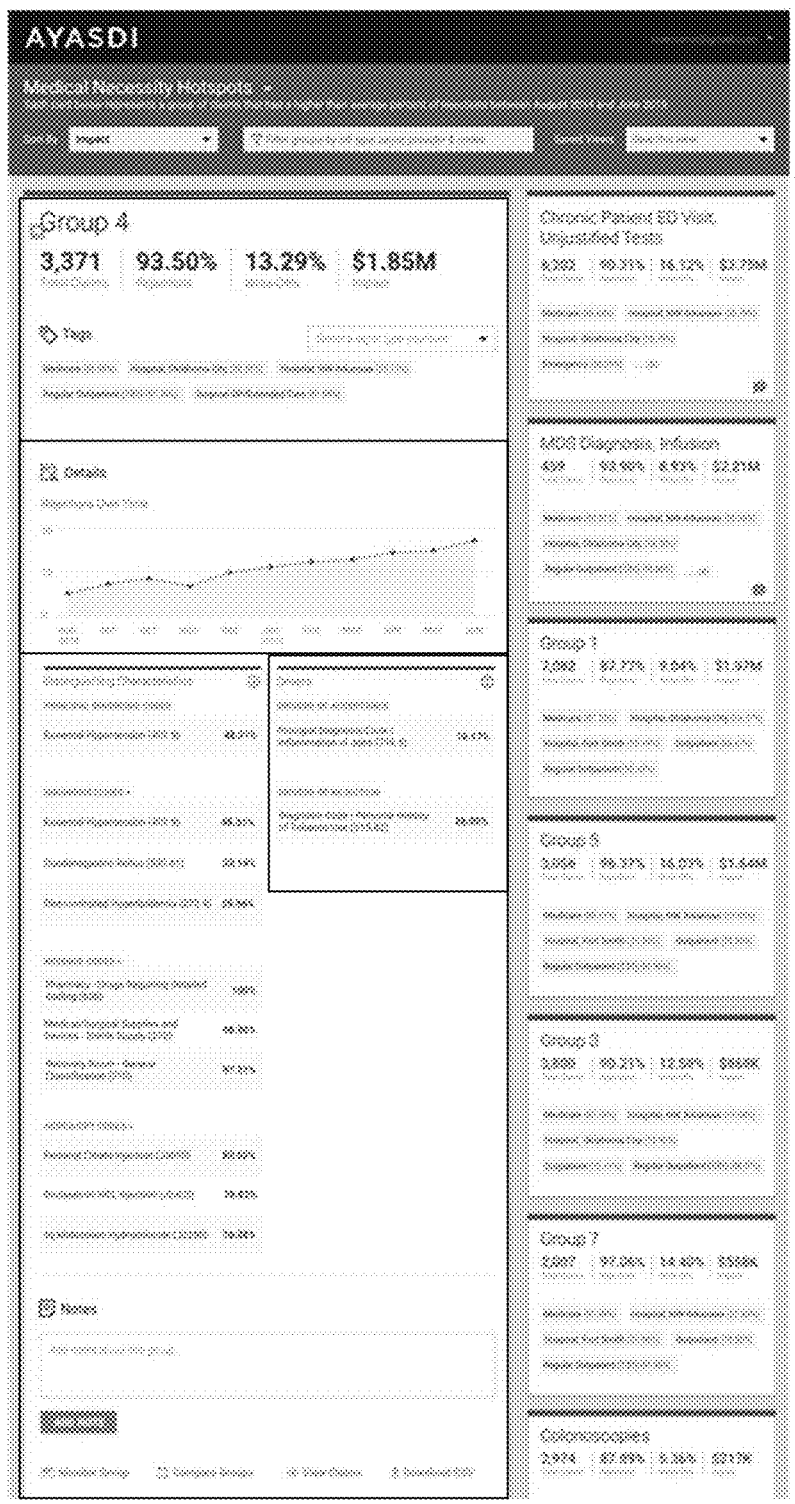
FIG. 37 depicts expanded card for Group 4 in the denials application user interface after a user may interact with the collapsed card for Group 4 (depicted in FIG. 36) in some embodiments.

FIG. 37 depicts expanded card for Group 4 in the denials application user interface after a user may interact with the collapsed card for Group 4 (depicted in FIG. 36) in some embodiments.

By engaging (e.g., clicking) on card for Group 4 as depicted in FIG. 31, the GCUI module 2708 depicts an expanded card. In various embodiments, the remaining cards stack up on the side of the denials application user interface (e.g., please see the other, unselected collapsed cards moved to the right of the window in the denials application user interface in FIG. 37).

In the expanded card, there is more information regarding this group. In various embodiments, the same summary statistics of this group of claims remains at the top of the expanded card. Just below the summary are a set of tags that provide additional statistics on the group of claims. Tags may be defined by labels on different statistical measures and/or users may create the tags to ease categorization and sorting (e.g., by utilizing field labeled "select a tag or type your own" in the denials application user interface of FIG. 37).

In various embodiments, the user may select within the denials application user interface a selection of statistics to generate and depict in the expanded card. In some embodiments, the denials application user interface enables the user to select statistics to generate and choose where those statistics should be depicted (e.g., in the collapsed or expanded card). In some embodiments, the denials application user interface enables the user to change statistics to be generated, or move statistics between views (e.g., from the collapsed view of the card to the expanded view, from the expanded view to the collapsed view, or on both the collapsed view and the expanded view).

It will be appreciated that a user may not be limited to statistical measures, but the user may select one or more function graphs to be depicted in the expanded view. In the example in FIG. 37, the graph depicts rejections over a timeline.

Below the graph, the denials application user interface depicts group insights. The Distinguishing Characteristics on the left describes the profile of the claims in this group in contrast to the rest of the data. These characteristics are categorized by principal diagnosis codes, diagnosis codes, revenue codes, HCPCs codes, and the like with each category revealing the overrepresented factor within each category.

There may be a longer list of drivers on the right of the denials application user interface which may suggest actions to take based on drivers of rejections within this group. These drivers may be ascertained by looking at rejected claims in comparison with accepted claims within the hotspot of similar claims. In this case, the members of group 4 (records and or users from the claim data that are members of nodes which are a part of group 4) and the claim adjudication are differentiated by principal diagnosis code 1 of inflammation of joint and diagnosis code I Personal History of Tobacco Use.

Figure 38:
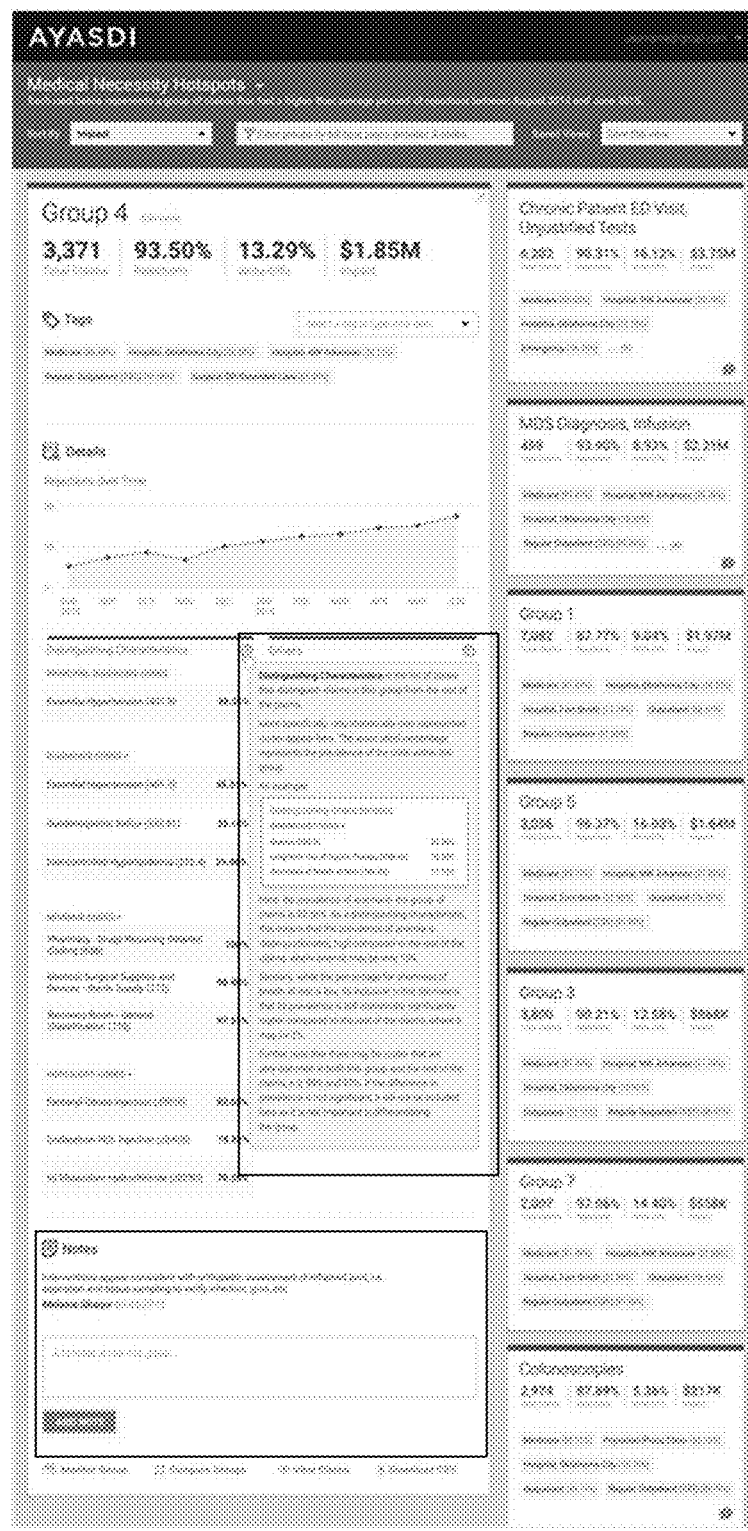
FIG. 38 depicts an expanded view of distinguishing characteristics of a driver of group 4 in the denials application user interface in some embodiments.

FIG. 38 depicts an expanded view of distinguishing characteristics of a driver of group 4 in the denials application user interface in some embodiments. In various embodiments, by interacting with an icon for more information regarding distinguishing characteristics of a driver, more information regarding distinguishing characteristics may be displayed. For example, the denials application user interface may depict an "I" icon indicating more information is available. If the denials application user interface receives an indication of a selection of that icon, the denials application user interface may provide an expanded view of that information. In this case, the distinguishing characteristics is a list of codes that distingue claims in this group from the rest of the claims. In this example, only statistically overrepresented codes may appear. The expanded information of the distinguishing characteristics may be generated by the analysis server 208 and/or provided by a data scientist or expert to highlight differentiating features or dimensions of the group of claim data in comparison with claim data of other groups.

In various embodiments, by interacting with a driver, more information regarding that driver may be displayed. For example, the denials application user interface may depict a collapsed view of a driver (e.g., see FIG. 37 regarding Principal Diagnosis Code I Inflammation of Joint (716.9)). If the denials application user interface receives an indication of a selection of that driver, the denials application user interface may provide an expanded view of that driver.

FIG. 38 also shows that users may leave notes regarding the groups.

Figure 39:
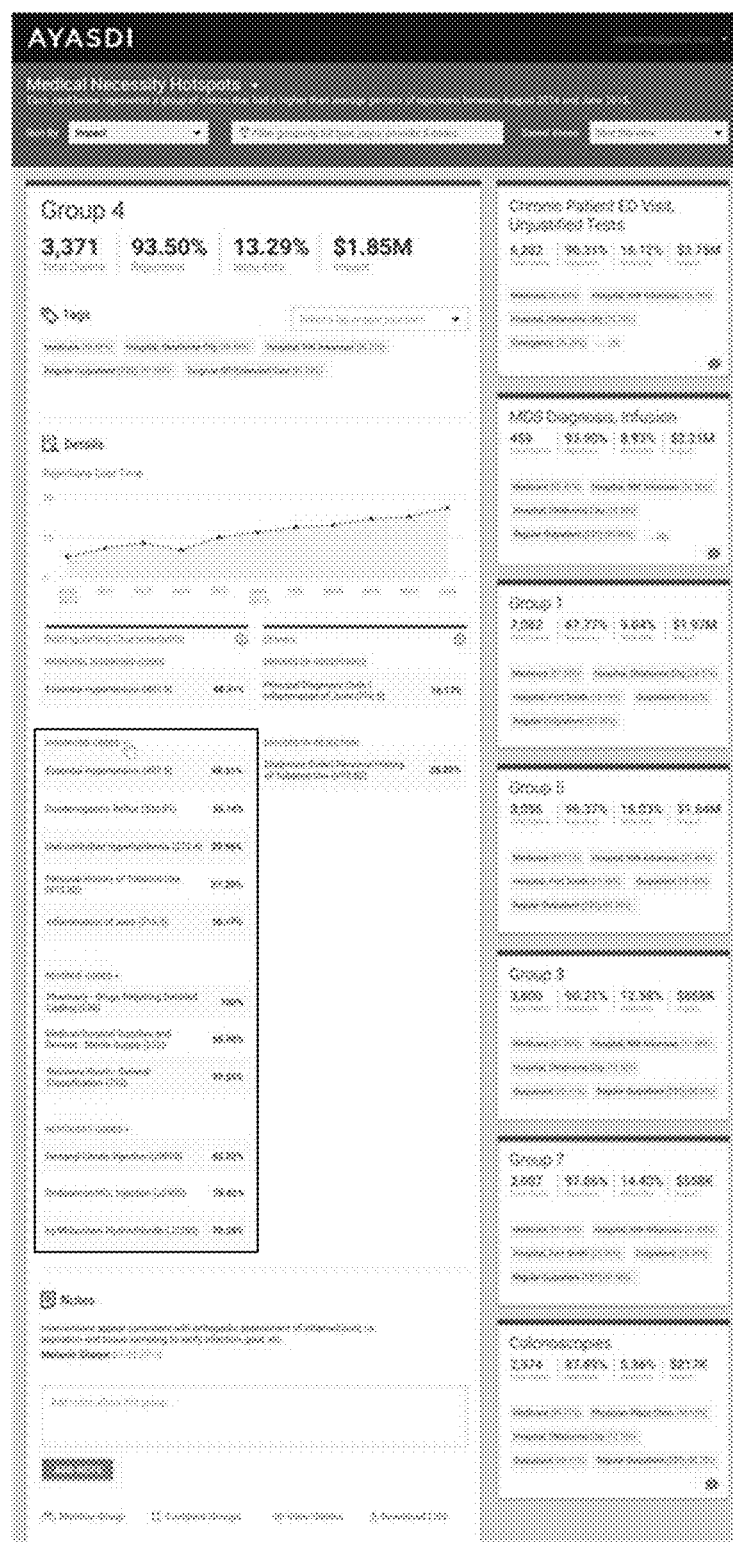
FIG. 39 depicts an expanded view of a distinguishing characteristics of group 4 in the denials application user interface in some embodiments

FIG. 39 depicts an expanded view of a distinguishing characteristics of group 4 in the denials application user interface in some embodiments. In this example, the denials application user interface receives an indication from a user that more information regarding diagnosis codes is desired (e.g., the user selected the diagnosis codes section of the denials application user interface). While previously three statistics were displayed, the denials application user interface displays five (e.g., adding statistics for "Personal History of Tobacco Use" and "Inflammation of Joint"). This may add additional information regarding this particular driver.

In various embodiments, each driver may include a group of statistics associated with that driver. As discussed herein, the analysis server 208 may determine the groups after generating the TDA graph using a query-less system. The analysis server 208 may identify groups of the TDA graph, perform various statistical methods on the groups (e.g., using standard methods, methods selected for the particular data set, and/or methods selected by a user), and then order the statistical measure (e.g., sort) based on largest impact or percentage to the group. In some embodiments, the analysis server 208 sorts the data based on impact or percentage within the group and also relative to other groups to identify differentiators relative to the larger group.

In the collapsed view, the number of statistical measures may be limited. Although the collapsed view shows three measures and the expanded view shows five. It will be appreciated that any number of measures may be determined and depicted. In various embodiments, the denials application user interface allows a user to select the number of statistical measures to show in the collapsed view and/or the expanded view.

Figure 40:
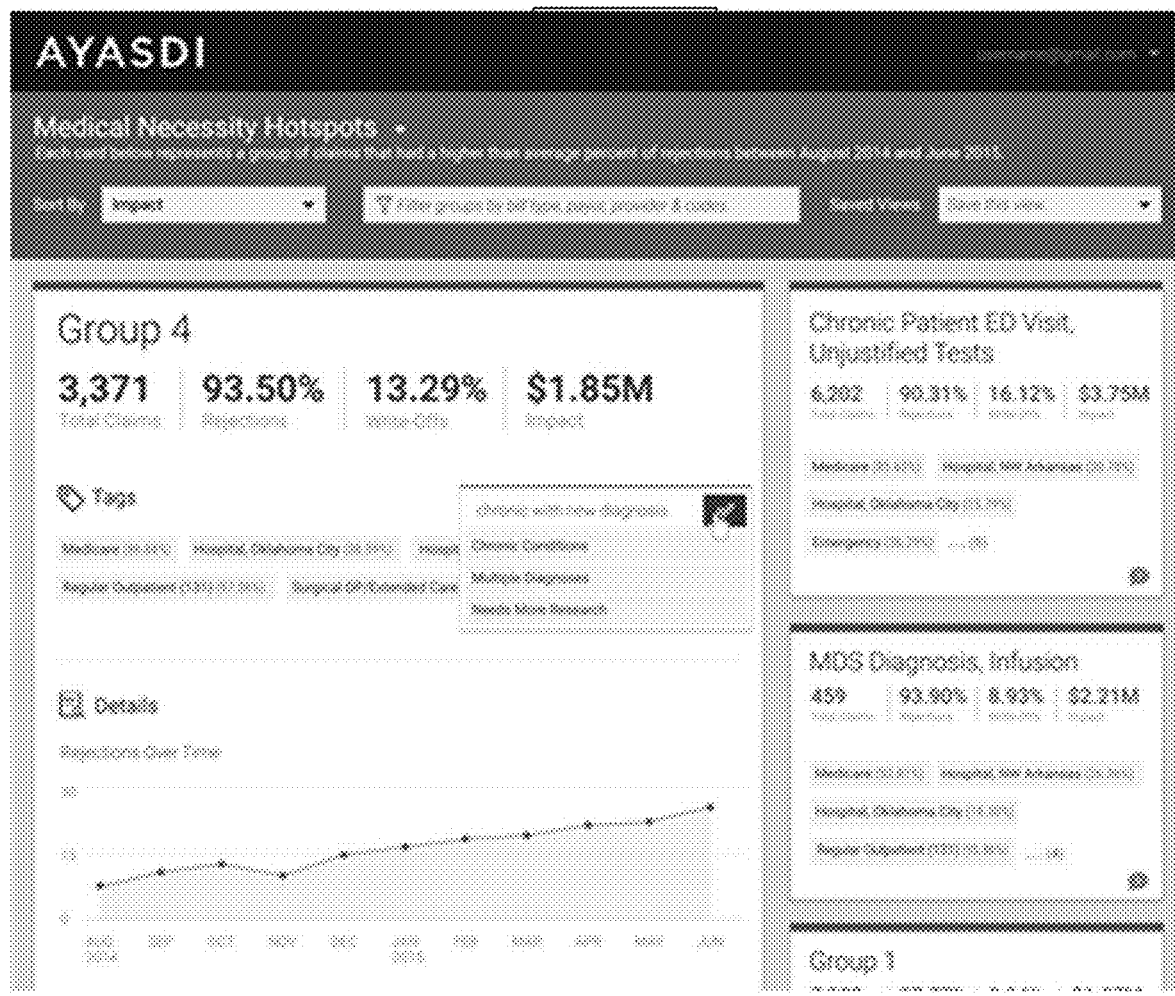
FIG. 40 depicts adding user defined tags to group 4 in the denials application user interface in some embodiments.

FIG. 40 depicts adding user defined tags to group 4 in the denials application user interface in some embodiments. As discussed herein, a user may enter their own tags better organize the interface and categorize data for comparison and contrast. In various embodiments, a hospital or other medical facility may use an assigned tag system. Such a list may be included within the denials application user interface (e.g., as a pull down menu or a menu in which the correct tag may be identified in a search).

In various embodiments, custom tags generated by user may appear in a different color in the denials application user interface to assist in distinguishing these tags.

Figure 41:
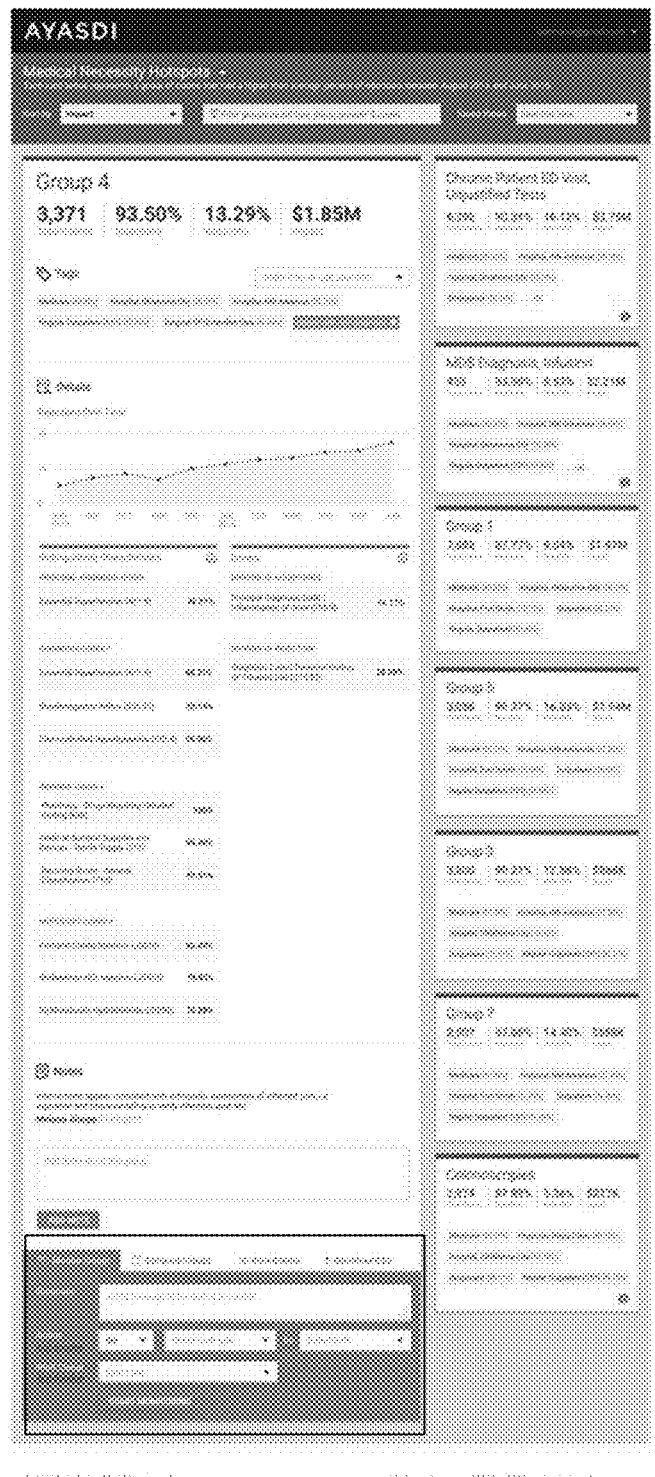
FIG. 41 depicts monitoring groups in the denials application user interface in some embodiments.

FIG. 41 depicts monitoring groups in the denials application user interface in some embodiments. The denials application user interface depicts an icon at the bottom of the interface to enable a user monitor the group (e.g., the group of the selected card). The user may mark the group for manual or automatic monitoring.

In this example, comments may be added as well as a specific action. Specific action may include set an action such as adding or replacing a code with another code. Further, an instruction or characterization may be entered in the pull down menu of the work queue. In this example, the user set monitoring to on, replaced one code with another automatically for future claims, and has added a characterization regarding acceptance or denial (i.e., "medical necessity").

In some embodiments, the specific action may include an audible noise, email, text, or any other alert. In various embodiments, the user may select one or more codes and if new claim data (not previously received) are added to the group, and the news claim data added to the group also includes one or more codes indicated by the user, actions may be taken (e.g., an email sent to a specific email address and/or an alert provided).

Figure 42:
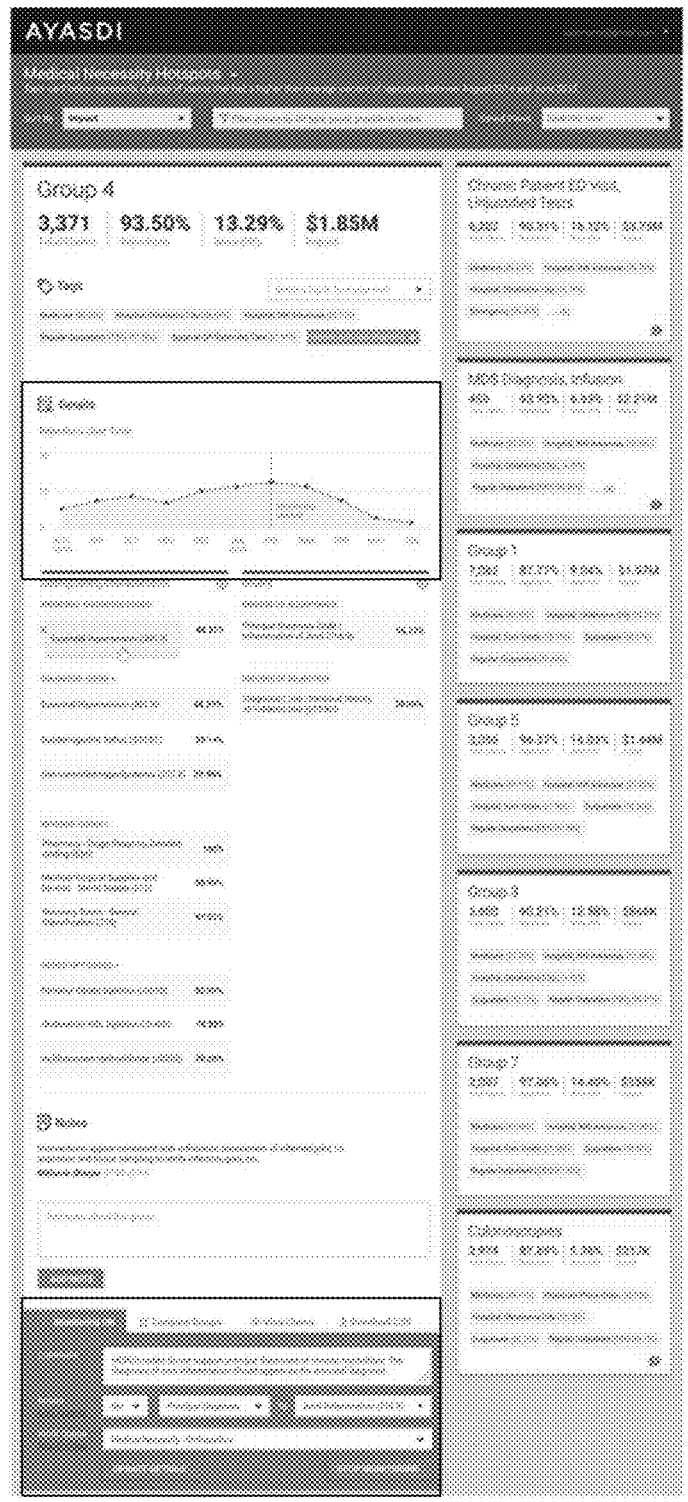
FIG. 42 depicts graphs in the denials application user interface in some embodiments.

FIG. 42 depicts graphs in the denials application user interface in some embodiments. As discussed herein, the denials application user interface may generate one or more graphs based on the information generated and/or received regarding the claims data. In this example, rejections over time are graphed. The graph shows when monitoring started and how adjustments to business reduces rejections over time.

Further, in this example, in the monitoring groups dialogue window of the denials application user interface, the user sets the principal diagnosis to "joint inflammation" for this group which allows the high rejection trend to decrease over time.

Figure 43:
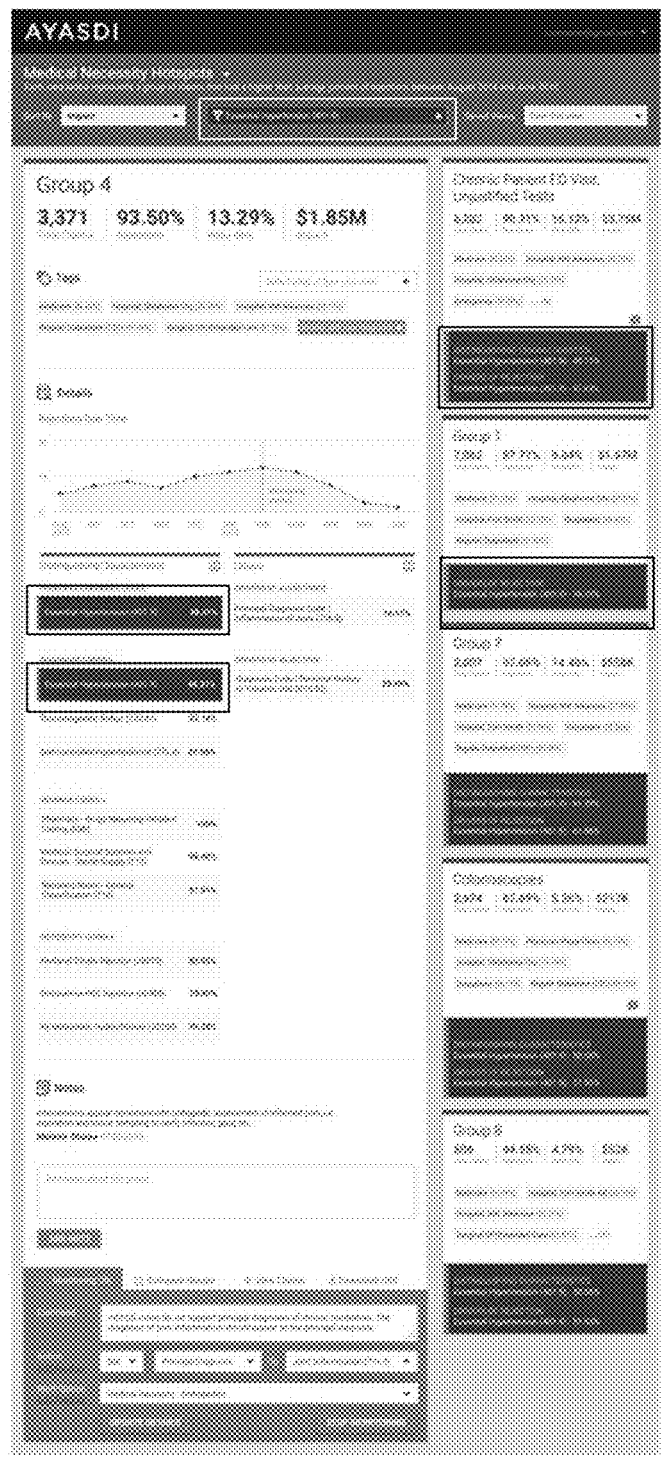
FIG. 43 depicts filtering in the denials application user interface in some embodiments.

FIG. 43 depicts filtering in the denials application user interface in some embodiments. It will be appreciated that by engaging filtering, the denials application user interface may further assist users in organizing information. For example, by filtering "essential hypertension" medical code in the field at the top of the denials application user interface, the denials application user interface may display and highlight groups where this code exists (e.g., see group 2, group 3, group 4, and group 5).

Figure 44:
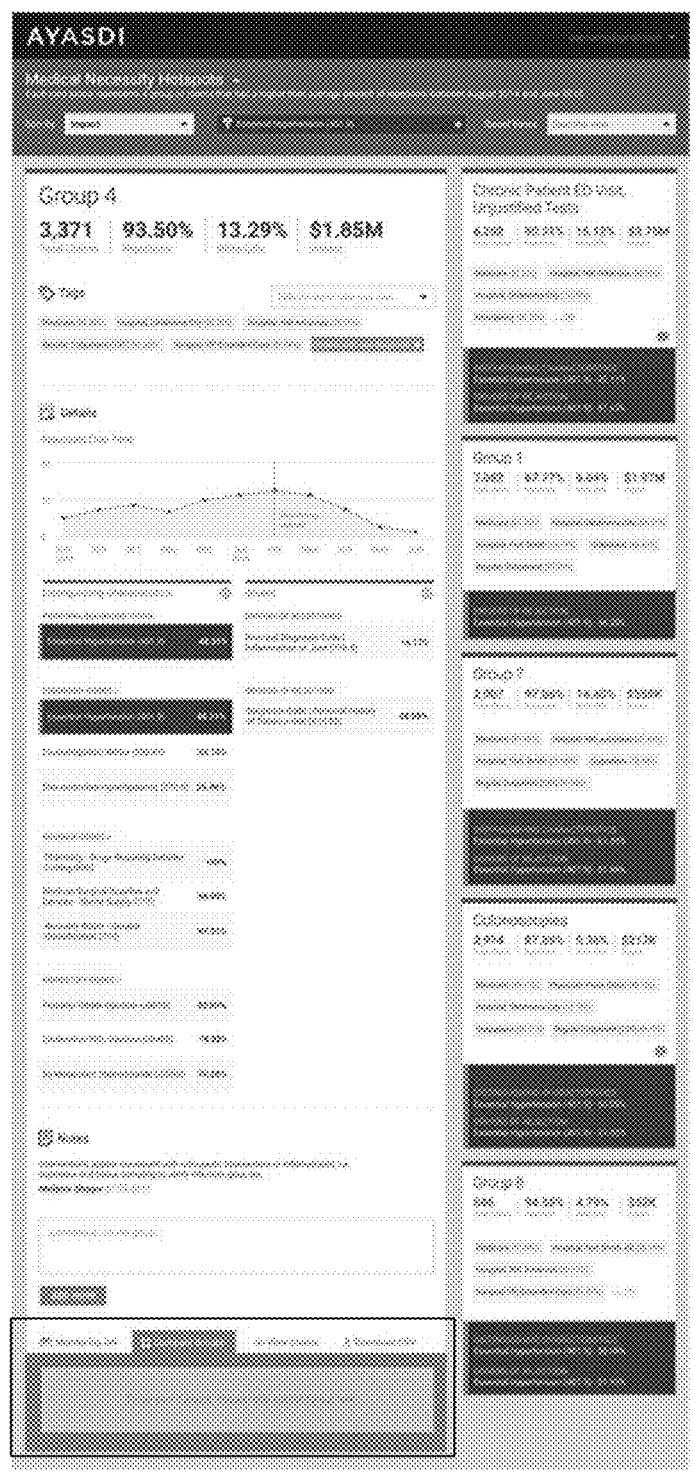
FIG. 44 depicts comparing groups in the denials application user interface in some embodiments.

FIG. 44 depicts comparing groups in the denials application user interface in some embodiments. in various embodiments, the denials application user interface enables the selection of two groups (e.g., two cards in the denials application user interface). And comparing them. In one example, this may be done by selecting and dragging each card in the denials application user interface to a comparison field (here at the bottom of the interface). The analysis system 208 and/or a user may compare and contrast the groups to indicate points of similarity and/or dissimilarity.

Figure 45:
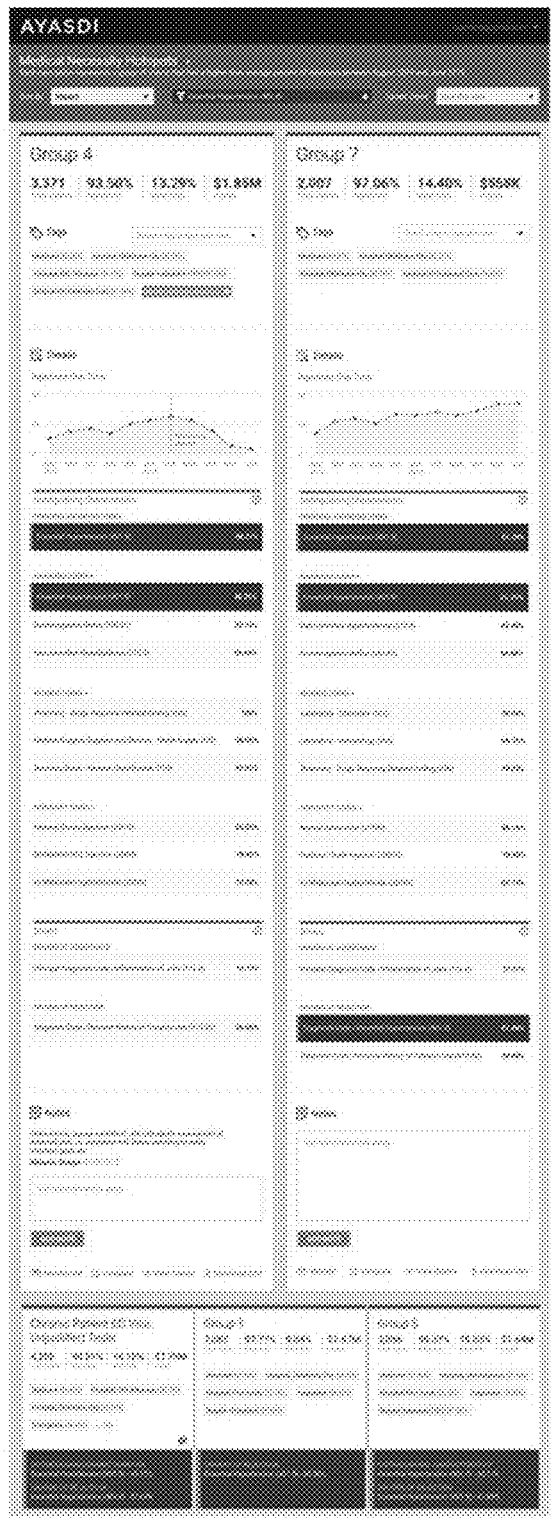
FIG. 45 depicts the selection of two groups that are side by side in the denials application user interface in some embodiments.

FIG. 45 depicts the selection of two groups that are side by side in the denials application user interface in some embodiments. In this case, the two groups are group 4 and 7. An expanded card of each section is displayed side-by-side. In various embodiments, notes may be added below for each of the groups. in some embodiments, the other, unselected cards may appear at the bottom of the interface.

It will be appreciated that the interface may be used with any multidimensional data that is separated into groups using TDA. In other words, the denials application user interface may be used in other contexts and solve other problems unrelated to claims or health care.

In some embodiments, the framework groups entities based on information from one or more health care systems. The framework may improve detection within these groups by, for example, prioritizing information that characterizes entity behavior. The framework may also allow for integration of new information associated with one or more entities that allow new groupings of entities and/or re-weightings (e.g., updated assessment).

In various embodiments, the analysis server 208 may receive credit card data for fraud detection and/or remediation. Credit card data may be multidimensional data including any number of features. For example, credit card data may include transactions for any number of accounts, size of purchase, notifications of fraud, time between fraudulent purchase(s) and notifications of fraud, indicia of fraud detection, amount lost, amount recovered, and/or the like. In various embodiments, credit card data may include a combination of non-fraudulent transactions and fraudulent transactions. The credit card data may include foreign and domestic transactions, or only foreign, or only domestic.

In various embodiments, the input module 314 may receive credit card data and/or any other financial data regarding any number of customers and accounts. Each row of data in the credit card data may be associated with a variety of features (or characteristics) which may be structured into columns. Features may include those identified above, but also any codes or other costs associated with successful transactions and/or fraudulent transactions.

The input module 314 may receive data from any number of sources (e.g., from any number of financial institutions such as banks, credit card companies, insurers, credit unions, credit scoring agencies, collections agencies, and/or the like). The data may be structured or unstructured.

The input module 314, the normalization module, or other financial entity may structure the data for analysis based on the documents, records, and/or any other information. In some embodiments, the input module 314, the normalization module, or other entity may generate new features based on existing features (e.g., by creating a new column based on previously provided information that may be within other columns).

The input module 314 and/or the normalization module may select a subset of columns for analysis (e.g., based on user selections). For example, the input module 314 and/or the normalization module may select any number of newly created columns and/or features and not select one or more previously created or received columns and/or features for analysis.

In various embodiments, the analysis server 208 includes a fraud grouping module which may identify groups of fraud in many different ways. In some embodiments, the fraud grouping module identifies users, similar features, and/or conditions (e.g., transactions) that are similar to known cases of fraud (e.g., utilizing TDA analysis as described herein). In another example, the fraud grouping module may identify transactions (e.g., by a string of transactions in time series data) as being extreme or significantly different from other transactions and/or features (e.g., based on centrality), other user's credit card information, groupings of healthy credit, groupings of fraudulent transactions, and/or that particular user's past behavior.

The following is a discussing regarding identifying groups of fraudulent transactions and/or groups of features associated with fraudulent transactions. In various embodiments, the input module 314 may receive credit card data including known fraudulent transactions. Analysis data may include data to be analyzed and TDA performed on the fraudulent transactions (the process of TDA being discussed herein). Transactions and/or other data identified in the analysis data may not have been previously investigated and/or it is unknown if the transaction is linked to information indicating or suggesting fraud. Known fraud data may be associated with cases of identified as being associated (e.g., as a result for further analysis or investigation) with fraud.

In various embodiments, the filter module 316 may receive one or more metric selection(s), one or more lens selection(s), a resolution and a gain as described herein. In this example, the filter module 316 may receive a section for variance normalized Euclidean (VME) with neighborhood lenses. It will be appreciated that the filter module 316 may apply any metric or combination of metrics. Similarly, the filter module 316 may apply any lens or combination of lenses.

After grouping the transactions based on similarity (e.g., using distances between features in the multidimensional data and a cover of the reference space), the fraud grouping module may be configured to identify (e.g., color) nodes based on known fraudulent outcomes.

As discussed herein, the analysis module 320 and/or the GUI engine 322 may generate a TDA graph using the analysis data and the known fraud information to generate a TDA graph with nodes and edges. Each node may have membership of one or more transactions. Nodes that are connected share at least one transaction as a member.

The fraud grouping module may identify users, behaviors, and/or transactions from the credit card data including those transactions that may be not have been previously identified as fraudulent. The fraud grouping module may identify transactions that may be not have been previously identified as fraudulent based on similarities with transactions, features, and/or the like that are known to be fraudulent and/or the identified groups of fraudulent behaviors.

In some embodiments, the fraud grouping module may also identify transactions and/or users or other information from the analysis data that are in nodes that are linked (i.e., with an edge) to a node containing at least one transaction from the known fraud or abuse data, to a node containing a number of transactions from the known fraud data that is equal to or greater than a predetermined number, or to a node containing a number of transactions from the known fraud data that is greater or equal to a threshold value when compared to a total number of members of the node (e.g., equal to or greater than a percentage).

In some embodiments, the fraud grouping module may receive node or transaction selections from a user or another digital device based on the TDA graph. For example, the GUI engine 322 may generate a visualization of the TDA graph for the user or the digital device. The user or digital device may identify one or more transactions for a report based on proximity, linking, node membership, or any other information. The transactions identified in the report may be identified for further investigation for possible fraud.

In one example, a user or a digital device may provide commands to the analysis server 208 to perform an additional function(s) on the features of the transactions (e.g., a Euclidean function and/or L1) and color the visualization by the result (based on the result of the function(s)). In this example, the function(s) may be performed for a set of features of a transaction. For each feature, the function(s) may be performed relative to that feature for that particular transaction(s) relative to the features of the other transactions (e.g., all transactions or those transactions from the credit card data). The user may select any number of transactions from the analysis data based on shared-membership of nodes (e.g., being a member of node that has members of one or more transactions from the known data) and/or color of the visualization (e.g., based on the result of the function(s)).

A reporting module may, in some embodiments, generate a report listing those transactions identified by the fraud grouping module. In some embodiments, nodes may be colored or otherwise identified by outcome, feature, or any combination of features (e.g., colored based on whether the node contains fraudulent transactions or a greater number of fraudulent transactions than a threshold). A user or the autogrouping module may group nodes into groups.

While, as previously discussed, examples of claims denials and financial fraud are used herein, it will be appreciated that systems and methods herein may be applied to any industry or field. For example, in some embodiments, systems and methods described herein may be applied to determining if entities are utilizing resources or systems without authorization, money laundering, laboratory mistakes or abuse, or the like.

In another example of the TDA process, the input module 314 may receive credit card data from any number of financial institutions. For example, rows of data may be associated with different transactions or sets of transactions. The analysis server 208 may perform TDA on all or selected columns (e.g., dimensions or features) of the credit card data. The analysis server 208 (e.g., the filter module 316) may receive metric and lens selections from a user or another digital device. The metric selection(s) may include any number of metrics from a set of metrics or pseudo-metrics (e.g., does not satisfy the triangle inequality) from a set of metrics. The lens function may project the data into the reference space as discussed herein. In one example, the metric and lens may be or include Variance Normalized Euclidean (VNE) with Neighborhood Lenses. The analysis server 208 (e.g., the resolution module) receives a resolution selection (e.g., resolution parameters) and possibly gain for analysis. The resolution parameters may be received from users or another digital device. In some embodiments, the resolution module 320 may determine one or more possible resolutions based on one or both sets of health care information. The resolution parameters and gain may be utilized to create a covering in the reference space to assist in clustering and/or for node membership. Subsequently, the analysis server 208 (e.g., the analysis module 320) performs metric and lens functions on the credit card data (e.g., or on the selected columns of the first and second set of health care information) to map financial information to a reference space. As similarly discussed, the analysis server 208 generates a cover in the reference space using the selected resolution and clusters the mapped financial information. The analysis server 208 (e.g., the processing module 212) generates a topological graph using at least some of the metric-lens(es) combinations from the subset of metric-lens combinations and at least one of the resolutions from subset of resolutions. The topological graph may be displayed (i.e., a visualization) or may be generated in memory. Nodes may be colored or otherwise identified by outcome, feature, or any combination of features (e.g., colored based on whether the node contains fraudulent transactions or a greater number of fraudulent transactions than a threshold). A user or the autogrouping module may group nodes into groups.

Figure 46:
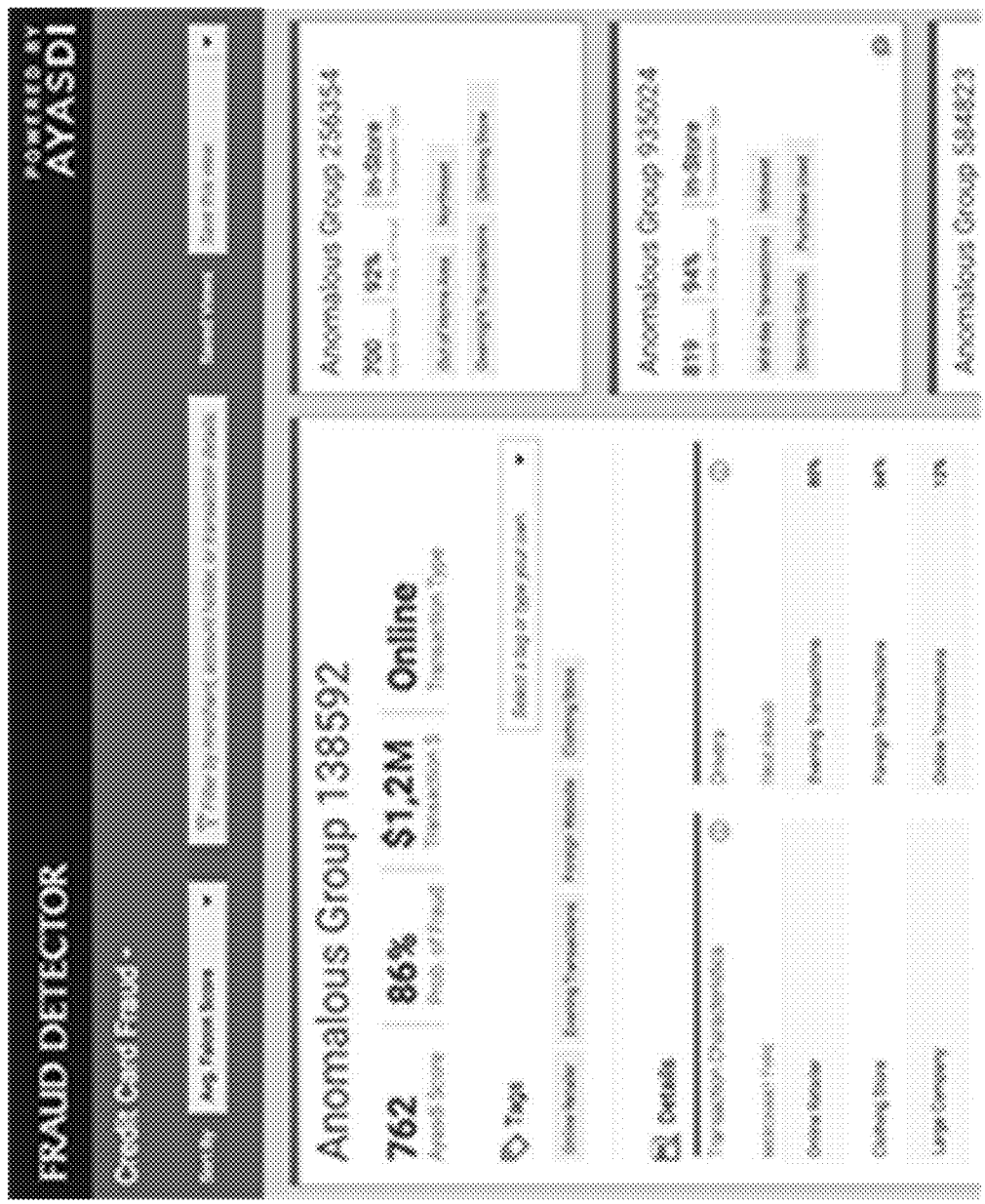
FIG. 46 depicts an expanded card for anomalous group 138592 in a financial application user interface for credit card fraud after a user interacts with the collapsed card for the group in some embodiments

FIG. 46 depicts an expanded card for anomalous group 138592 in a financial application user interface for credit card fraud after a user interacts with the collapsed card for the group in some embodiments. The financial application user interface functions similarly to the denials application user interface. By engaging (e.g., clicking) on a collapsed card for anomalous group 138592, the GCUI module 2708 causes the card to expand. In various embodiments, the remaining cards stack up on the side of the financial application user interface (e.g., please see the other, unselected collapsed cards moved to the right of the window in the de financial application user interface in FIG. 46).

In the expanded card, there is more information regarding this group. In various embodiments, the same summary statistics of this group of claims remains at the top of the expanded card. In this case, the card indicates a score of 762 indicating a measure of the group for fraud (e.g., significance relative to other groups), a probability of fraud (86%), an amount of transactions of the group ($1.2 m), and a transaction type (online). Just below the summary are a set of tags that provide additional statistics on the group. It will be appreciate that the financial application user interface may generate any number of summary statistics. In some embodiments, a user may select which statistics to be displayed in the summary statistics.

Tags may be defined by labels on different statistical measures and/or users may create the tags to ease categorization and sorting (e.g., by utilizing field labeled "select a tag or type your own" in the denials application user interface of FIG. 46).

In various embodiments, the user may select from the financial application user interface a selection of statistics to generate and depict in the expanded card. In some embodiments, the financial application user interface enables the user to select statistics to generate and choose where those statistics should be depicted (e.g., in the collapsed or expanded card). In some embodiments, the financial application user interface enables the user to change statistics to be generated, or move statistics between views (e.g., from the collapsed view of the card to the expanded view, from the expanded view to the collapsed view, or on both the collapsed view and the expanded view).

It will be appreciated that a user may not be limited to statistical measures, but the user may select one or more function graphs to be depicted in the expanded view. Below the graph, the financial application user interface may depict group insights. The details section of the financial application user interface may describe the profile of transactions in this group in contrast to the rest of the credit card data in other groups (or relative to the other groups).

There may be drivers section to the right of the details section indicating primary drivers or differentiators from other groups. These drivers may be ascertained by looking at fraudulent transactions or claims in comparison with expected non-fraudulent transactions or claims within the hotspot of similar claims.

Figure 47:
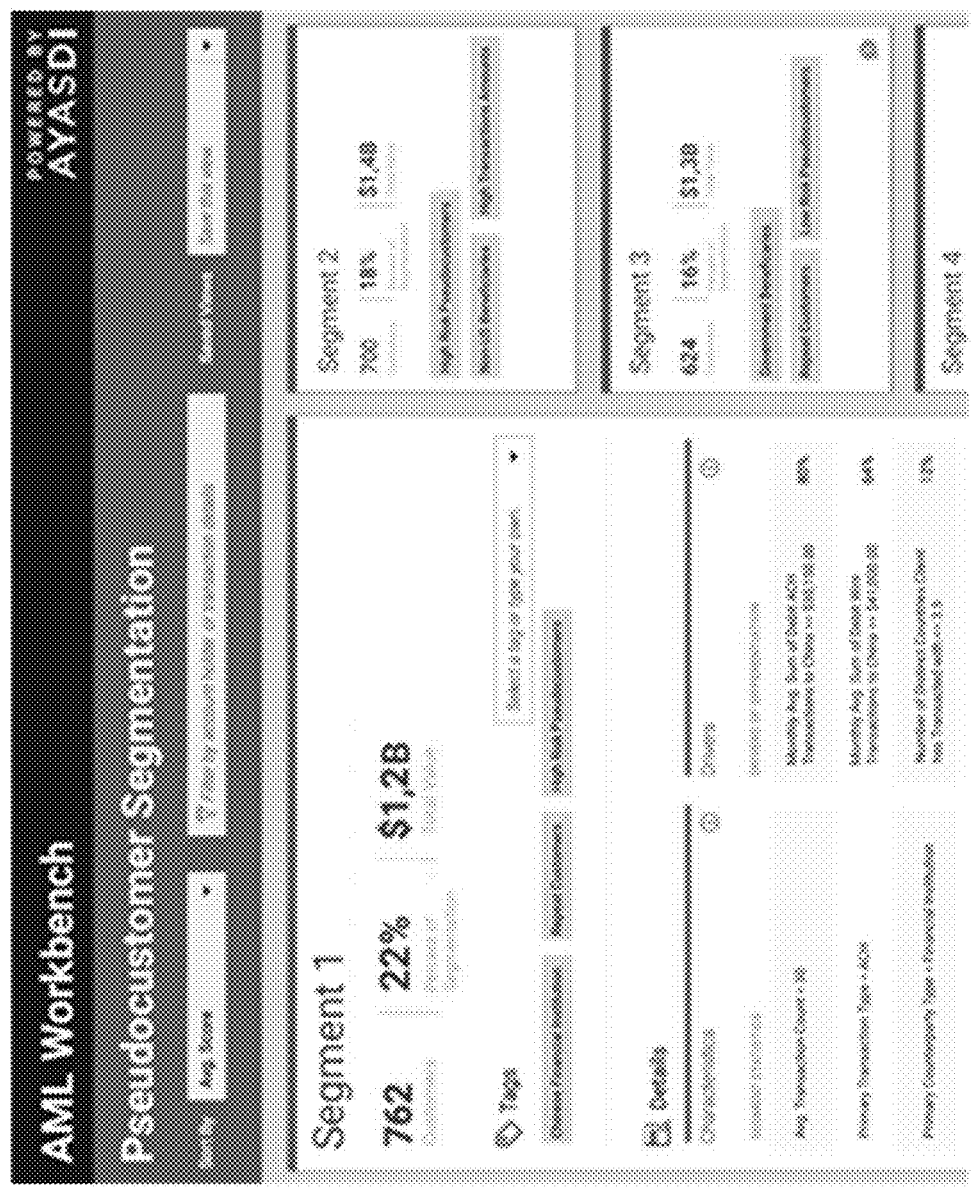
FIG. 47 depicts an expanded card for anomalous pseudo-customer segmentation in an anti-money laundering (AML) user interface for AML after a user interacts with the collapsed card for the group in some embodiments.

FIG. 47 depicts an expanded card for anomalous pseudo-customer segmentation in an anti-money laundering (AML) user interface for AML after a user interacts with the collapsed card for the group in some embodiments. The AML user interface functions similarly to the denials application user interface and the financial application user interface. By engaging (e.g., clicking) on a collapsed card for pseudocustomer segmentation, the GCUI module 2708 causes the card to expand. In various embodiments, the remaining cards stack up on the side of the AML user interface (e.g., please see the other, unselected collapsed cards moved to the right of the window in the AML user interface in FIG. 47).

In the expanded card, there is more information regarding this group. In various embodiments, the same summary statistics of this group of claims remains at the top of the expanded card. In this case, the card indicates 762 customers, 22% segmentation and a $1.2B in total value. It will be appreciate that the AML user interface may generate any number of summary statistics. In some embodiments, a user may select which statistics to be displayed in the summary statistics.

Just below the summary are a set of tags that provide additional statistics on the group. Tags may be defined by labels on different statistical measures and/or users may create the tags to ease categorization and sorting (e.g., by utilizing field labeled "select a tag or type your own" in the denials application user interface of FIG. 47).

In various embodiments, the user may select from the AML user interface of statistics to generate and depict in the expanded card. In some embodiments, the financial application user interface enables the user to select statistics to generate and choose where those statistics should be depicted (e.g., in the collapsed or expanded card). In some embodiments, the AML user interface enables the user to change statistics to be generated, or move statistics between views (e.g., from the collapsed view of the card to the expanded view, from the expanded view to the collapsed view, or on both the collapsed view and the expanded view).

It will be appreciated that a user may not be limited to statistical measures, but the user may select one or more function graphs to be depicted in the expanded view. Below the graph, the AML user interface may depict group insights. The details section of the AML user interface may describe the profile of transactions in this group in contrast to the rest of the credit card data in other groups (or relative to the other groups).

There may be drivers section to the right of the details section indicating primary drivers or differentiators from other groups. These drivers may be ascertained by looking at fraudulent transactions or claims in comparison with expected non-fraudulent transactions or claims within the hotspot of similar claims.

The above-described functions and components can be comprised of instructions that are stored on a storage medium (e.g., a computer readable storage medium). The instructions can be retrieved and executed by a processor. Some examples of instructions are software, program code, and firmware. Some examples of storage medium are memory devices, tape, disks, integrated circuits, and servers. The instructions are operational when executed by the processor (e.g., a data processing device) to direct the processor to operate in accord with embodiments of the present invention. Those skilled in the art are familiar with instructions, processor(s), and storage medium.

The present invention has been described above with reference to example embodiments. It will be apparent to those skilled in the art that various modifications may be made and other embodiments can be used without departing from the broader scope of the invention. Therefore, these and other variations upon the example embodiments are intended to be covered by the present invention.

The invention claimed is:

1. A non-transitory computer readable medium including executable instructions, the instructions being executable by at least one processor to perform a method, the method comprising:
  performing a topological data analysis process on multidimensional adjudicated claims data, the performing the topological data analysis process including:
    receiving the multidimensional adjudicated claims data, the multidimensional adjudicated claims data including information regarding claim denials for health services, the multidimensional adjudicated claims data further including a first set of claims that have been identified as improperly denied as well as a second set of other claims, the first set of claims having been improperly denied based on at least one incorrect health billing code, each of the at least one incorrect health billing code being for a particular medical procedure, the multidimensional adjudicated claims data further including indications of why a claim of the first set of claims was previously improperly denied, the claims of the first set of claims being previously improperly denied for a variety of different reasons;
    receiving at least one metric function and at least one lens function selection;
    performing the at least one metric function and the at least one lens function on a set of dimensions of the multidimensional adjudicated claims data to map the claims of the first set of claims, the claims of the second set of claims, and the indications to a reference space, wherein receiving the multidimensional adjudicated claims data including the first set of claims, the second set of claims, and the indications occurs before performing the at least one metric function and the at least one lens function;
    generating a cover of overlapping sets of the reference space based on a resolution;
    clustering the mapped claims in the reference space using the cover to identify nodes in a topological data analysis graph, each node including one or more claims of the first set of claims as well as one or more claims of the second set of claims as members, each node being connected to another node if they share at least one common claim as members;
    generating a topological data analysis graph of the nodes and edges;
    identifying groups of nodes in the topological data analysis graph based on claims of the first sets of claims that are members of the nodes;
    for each group, identifying differentiating drivers that led to the denial of the claims of the first set of claims in the nodes of that group, the identification of differentiating drivers being based on dimensions of the claims in the nodes of that group, the differentiating drivers being particular to that group relative to other groups in the topological data analysis graph, the identification of differentiating drivers being further based on comparison of claims of the first set of claims with claims of the second set of claims in the nodes of that group, at least one of the claims of the first set of claims in the nodes of that group for a patient different from patients for claims of the second set of claims in the nodes of that group; and
  generating a denials application user interface depicting a card for each of at least a subset of the identified groups in the topological data analysis graph that includes the claims of the first set of claims that are the members of the nodes, each card indicating a set of primary statistics based on at least one dimension of each of the claims in the nodes of that group, for each card, the denials application user interface further depicting the differentiating drivers that led to the denial of claims based on the dimensions of the claims in the nodes of that group.

2. The non-transitory computer readable medium of claim 1, wherein the multidimensional adjudicated claims data includes at least one claim for precertification for medical services.

3. The non-transitory computer readable medium of claim 1, wherein the multidimensional adjudicated claims data includes at least one claim for medical services already rendered.

4. The non-transitory computer readable medium of claim 1, wherein the set of dimensions of the multidimensional adjudicated claims data is filtered to a reduced set of dimensions prior to performing the at least one metric function and the at least one lens function on the set of dimensions.

5. The non-transitory computer readable medium of claim 1, wherein identifying the groups of nodes in the topological data analysis graph based on claims of the first sets of claims that are the members of the nodes includes identifying nodes containing claims with similar dimensions and similar claim denials.

6. The non-transitory computer readable medium of claim 1, wherein the multidimensional adjudicated claims data includes at least one dimension regarding reasons for claim denial.

7. The non-transitory computer readable medium of claim 1, wherein the method further comprises ranking the groups of the nodes in the topological data analysis graph based on cost of claim denials relative to the other groups of the nodes in the topological data analysis graph.

8. The non-transitory computer readable medium of claim 7, wherein the denials application user interface is configured to display on each depicted card the cost of claim denials.

9. The non-transitory computer readable medium of claim 7, wherein the denials application user interface is configured to order the cost based on the cost of claim denials.

10. The non-transitory computer readable medium of claim 1, wherein the method further comprises receiving a new adjudicated claim, comparing dimensions of the new adjudicated claim to the groups and predicting a likelihood that the new adjudicated claim is improperly denied.

11. The non-transitory computer readable medium of claim 10, wherein comparing the dimensions of the new adjudicated claim to the groups includes comparing the dimensions of the new adjudicated claim to the differentiating drivers of each group.

12. A system comprising:
at least one processor; and
memory containing instructions to configure the at least one processor to:
perform a topological data analysis process on multidimensional adjudicated claims data, the performing the topological data analysis process including:
receive the multidimensional adjudicated claims data, the multidimensional adjudicated claims data including information regarding claim denials for health services, the multidimensional adjudicated claims data further including a first set of claims that have been identified as improperly denied as well as a second set of other claims, the first set of claims having been improperly denied based on at least one incorrect health billing code, each of the at least one incorrect health billing code being for a particular medical procedure, the multidimensional adjudicated claims data further including indications of why a claim of the first set of claims was previously improperly denied, the claims of the first set of claims being previously improperly denied for a variety of different reasons;
receive at least one metric function and at least one lens function selection;
perform the at least one metric function and the at least one lens function on a set of dimensions of the multidimensional adjudicated claims data to map the claims of the first set of claims, the claims of the second set of claims, and the indications to a reference space, wherein receiving the multidimensional adjudicated claims data including the first set of claims, the second set of claims, and the indications occurs before performing the at least one metric function and the at least one lens function;
generate a cover of overlapping sets of the reference space based on a resolution;
cluster the mapped claims in the reference space using the cover to identify nodes in a topological data analysis graph, each node including one or more claims of the first set of claims as well as one or more claims of the second set of claims as members, each node being connected to another node if they share at least one common claim as members;
generate a topological data analysis graph of the nodes and edges;
identify groups of nodes in the topological data analysis graph based on claims of the first sets of claims that are members of the nodes;
for each group, identify differentiating drivers that led to the denial of the claims of the first set of claims in the nodes of that group, the identification of differentiating drivers being based on dimensions of the claims in the nodes of that group, the differentiating drivers being particular to that group relative to other groups in the topological data analysis graph, the identification of differentiating drivers being further based on comparison of claims of the first set of claims with claims of the second set of claims in the nodes of that group, at least one of the claims of the first set of claims in the nodes of that group for a patient different from patients for claims of the second set of claims in the nodes of that group; and
generate a denials application user interface depicting a card for each of at least a subset of the identified groups in the topological data analysis graph that includes the claims of the first set of claims that are the members of the nodes, each card indicating a set of primary statistics based on at least one dimension of each of the claims in the nodes of that group, for each card, the denials application user interface further depicting the differentiating drivers that led to the denial of claims based on the dimensions of the claims in the nodes of that group.

13. The system of claim 12, wherein the multidimensional adjudicated claims data includes at least one claim for precertification for medical services.

14. The system of claim 12, wherein the multidimensional adjudicated claims data includes at least one claim for medical services already rendered.

15. The system of claim 12, wherein the set of dimensions of the multidimensional adjudicated claims data is filtered to a reduced set of dimensions prior to performing the at least one metric function and the at least one lens function on the set of dimensions.

16. The system of claim 12, wherein identifying the groups of nodes in the topological data analysis graph based on the claims of the first sets of claims that are the members of the nodes includes identifying nodes containing claims with similar dimensions and similar claim denials.

17. The system of claim 12, wherein the multidimensional adjudicated claims data includes at least one dimension regarding reasons for claim denial.

18. The system of claim 12, wherein the instructions further configure the at least one processor to rank the groups of the nodes in the topological data analysis graph based on cost of claim denials relative to the other groups of the nodes in the topological data analysis graph.

19. The system of claim 18, wherein the denials application user interface is configured to display on each depicted card the cost of claim denials.

20. The system of claim 18, wherein the denials application user interface is configured to order the cost based on the cost of claim denials.

21. The system of claim 12, wherein the instructions further configure the at least one processor to receive a new adjudicated claim, compare dimensions of the new adjudicated claim to the groups and predict a likelihood that the new adjudicated claim is improperly denied.

22. The system of claim 21, wherein the instructions further configure the at least one processor to compare the dimensions of the new adjudicated claim to the groups by comparing the dimensions of the new adjudicated claim to the differentiating drivers of each group.

* * * * *